(12) United States Patent
Koga et al.

(10) Patent No.: US 8,133,882 B2
(45) Date of Patent: Mar. 13, 2012

(54) QUINOLONE DERIVATIVE OR PHARMACEUTICALLY ACCEPTABLE SALT THEREOF

(75) Inventors: Yuji Koga, Tokyo (JP); Takao Okuda, Tokyo (JP); Susumu Watanuki, Tokyo (JP); Takashi Kamikubo, Tokyo (JP); Fukushi Hirayama, Tokyo (JP); Hiroyuki Moritomo, Tokyo (JP); Jiro Fujiyasu, Tokyo (JP); Michihito Kageyama, Tokyo (JP); Toshio Uemura, Tokyo (JP); Jun Takasaki, Tokyo (JP)

(73) Assignee: Astellas Pharma Inc, Tokyo (JP)

( * ) Notice: Subject to any disclaimer, the term of this patent is extended or adjusted under 35 U.S.C. 154(b) by 723 days.

(21) Appl. No.: 12/293,055

(22) PCT Filed: Mar. 14, 2007

(86) PCT No.: PCT/JP2007/055040
§ 371 (c)(1),
(2), (4) Date: Sep. 15, 2008

(87) PCT Pub. No.: WO2007/105751
PCT Pub. Date: Sep. 20, 2007

(65) Prior Publication Data
US 2009/0197834 A1    Aug. 6, 2009

(30) Foreign Application Priority Data
Mar. 16, 2006  (JP) .................... 2006-073045

(51) Int. Cl.
*A61K 31/675*  (2006.01)
*A61K 31/47*   (2006.01)
*C07D 215/22*  (2006.01)
*C07F 9/60*    (2006.01)
(52) U.S. Cl. ............. 514/82; 514/312; 546/24; 546/155
(58) Field of Classification Search .................... 514/24, 514/155; 546/82, 312
See application file for complete search history.

(56) References Cited

U.S. PATENT DOCUMENTS 7,488,739 B2 * 2/2009 Watanuki et al. ............ 514/312

FOREIGN PATENT DOCUMENTS

| EP | 0 614 664 A1 | 9/1994 |
|---|---|---|
| EP | 0 945 435 A1 | 9/1999 |
| EP | 1 650 192 A1 | 4/2006 |
| WO | 98/23592 A1 | 6/1998 |
| WO | 00/34283 A1 | 6/2000 |
| WO | 02/098856 A2 | 12/2002 |
| WO | 03/022214 A2 | 3/2003 |
| WO | 2005/000281 A2 | 1/2005 |
| WO | 2005/009971 A1 | 2/2005 |
| WO | WO 2005009971 A1 * | 2/2005 |
| WO | 2005/035520 A1 | 4/2005 |
| WO | 2006/077851 A1 | 7/2006 |

OTHER PUBLICATIONS

Office Action dated Dec. 14, 2010, issued in corresponding Indonesian Patent Application No. W-00 2008 02976.
Russian Patent Office, Office Action dated Feb. 17, 2011, issued in corresponding Russian Application No. 2008140946.
Masakiyo Nobuyoshi, et al. "Restenosis After Successful Percutaneous Transluminal Coronary Angioplasty: Serial Angiographic Follow-Up of 229 Patients" JACC 1988, vol. 12, p. 616-623.
Chinese Office Action issued on Jul. 14, 2010 in the corresponding Chinese Patent Application No. 200780009148.X.
Chinese Patent Office, Chinese Office Action issued in corresponding CN Application No. 200780009148.X, dated Aug. 24, 2011.

* cited by examiner

*Primary Examiner* — Yong Chu
(74) *Attorney, Agent, or Firm* — Sughrue Mion, PLLC

(57) ABSTRACT

Provided are quinolone derivatives having a lower alkyl or cycloalkyl at the 1-position; —N(R°)C(O)-lower alkylene-CO$_2$R°, lower alkylene-CO$_2$R°, lower alkenylene-CO$_2$R°, —O-lower alkylene-CO$_2$R°, —O-(lower alkylene which may be substituted with —CO$_2$R°)-aryl or —O-lower alkenylene-CO$_2$R° (wherein R° is H or lower alkyl) at the 3-position; halogen at the 6-position; and amino group substituted with a substituent group having a ring structure at the 7-position, respectively, or pharmaceutically acceptable salts thereof. Pharmaceutical composition containing the quinolone derivatives and methods of using the compositions are provided.

18 Claims, No Drawings

QUINOLONE DERIVATIVE OR PHARMACEUTICALLY ACCEPTABLE SALT THEREOF

TECHNICAL FIELD

The present invention relates to a pharmaceutical, particularly a novel quinolone derivative or a pharmaceutically acceptable salt thereof, which is useful as a platelet aggregation inhibitor or a P2Y12 inhibitor.

BACKGROUND OF THE INVENTION

Since the discovery by Donne et al. in 1842, blood platelets have been regarded for a long time as a component of blood necessary for hemostasis. Nowadays, it has been revealed that platelets not only simply play the leading role in the hemostatic mechanism but also show clinically noteworthy multi-functional properties such as concern in the realization of arteriosclerosis, circulatory organ diseases including thrombotic diseases, metastasis, inflammation, rejection reaction after transplantation and immune reaction.

In general, therapies for blood reperfusion with pharmaceutical agents or physical methods have been carried out for thrombotic diseases and ischemic diseases. However, a phenomenon in which activation, adhesion and aggregation of platelets are accelerated after carrying out revascularization due to breakdown of vascular tissues including endothelial cells, or collapse of fibrinolysis-coagulation balance or the like caused by the drug itself, has recently been found and causing clinical problems. For example, it has been revealed that after recirculation by a thrombolytic therapy using t-PA or the like, fibrinolysis ability and coagulation ability are activated and systemic coagulation-fibrinolysis balance collapses. Clinically, it results in re-obstruction which has been causing a therapeutically large problem (Non-patent reference 1).

On the other hand, a PTCA therapy or a stent indwelling method has been rapidly popularizing and gaining a certain fruit for the treatment of diseases based on angina pectoris, myocardial infarction and the like coronary artery stricture and aorta stricture. However, since these therapeutic methods damage vascular tissues including endothelial cells, acute coronary obstruction, and further re-stricture which occurs at chronic stage, has been causing problems. Platelets are taking an important role in various thrombolytic ill effects (re-obstruction and the like) after such a revascularization. Thus, effectiveness of an anti-platelet agent is expected, but sufficient effects of the conventional anti-platelet agents have not been confirmed.

As preventive or therapeutic agents for such circulatory organ system diseases, aspirin, cilostazol, prostaglandin $I_2$, prostaglandin $E_1$, ticlopidine, clopidogrel, dipyridamole and the like platelet aggregation inhibitors have been used. Also in recent years, a GPIIb/IIIa antagonist which inhibits the final step of platelet aggregation and has strong platelet aggregation inhibition activity has been developed, but its use is limited to the intravenous drip infusion at thrombosis acute phase (Non-patent reference 2).

In recent years, it has been revealed that, regarding ticlopidine and clopidogrel which are used as anti-platelet agents, these are exerting platelet aggregation inhibitory activity through the inhibition of P2Y12 as an ADP receptor by their active metabolites. Thereafter, a triazolo[4,5-D]pyrimidine derivative (Patent reference 1), piperazine and/or homopiperazine derivatives (Patent Reference 2 and Patent Reference 3), a pyrazolidinedione derivative (Patent Reference 4), an isoquinolinone derivative (Patent Reference 5) and the like have been reported as compounds having P2Y12 inhibitory activity.

On the other hand, Patent References 6 and 7 are known as quinolone derivatives.

In Patent Reference 6, a compound represented by a formula (A) having antimicrobial action is known, but possession of platelet aggregation inhibitory activity by these derivatives is not known. In addition, its structure is different from the compound of the present invention in terms that the moiety which corresponds to $R^5$ of the compound of the present invention is a carboxylic acid, ester or carbamoyl.

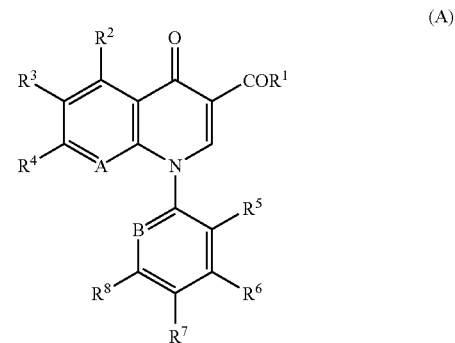

(A)

(In the formula, $R^1$ represents —$OR^9$, amino group or lower alkylamino group, and R9 hydrogen atom or a carboxy-protecting group. See said official gazette for other symbols.)

In Patent Reference 7, it is reported that a compound represented by a formula (B) has P2Y12 inhibitory activity. However, its structure is different from the compound of the present invention in terms that the moiety which corresponds to $R^5$ of the compound of the present invention is carbamoyl.

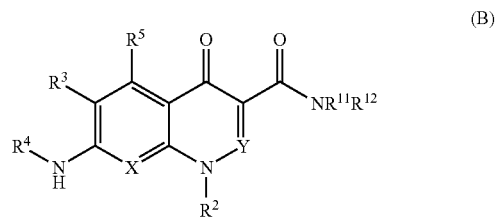

(B)

(See Said Official Gazette for Symbols in the Formula.)

In Patent Reference 8, it is reported that a compound represented by a formula (C) has P2Y12 inhibitory activity. However, its structure is different from the compound of the present invention in terms that the moiety which corresponds to $R^5$ of the compound of the present invention is carbamoyl.

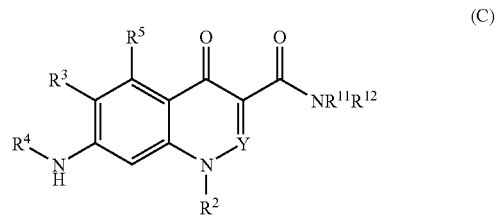

(C)

(See Said Official Gazette for Symbols in the Formula.)

Non-patent reference 1: "Journal of American College of Cardiology", 1988, vol. 12, p. 616-623
Non-patent reference 2: "Sogo Rinsho (Synthetic Clinic)", 2003, vol. 52, p. 1516-1521
Patent Reference 1: International Publication WO 00/34283
Patent Reference 2: International Publication WO 02/098856
Patent Reference 3: International Publication WO 03/022214
Patent Reference 4: International Publication WO 05/000281
Patent Reference 5: International Publication WO 05/035520
Patent Reference 6: International Publication WO 98/23592
Patent Reference 7: International Publication WO 05/009971
Patent Reference 8: International Publication WO 06/077851

DISCLOSURE OF THE INVENTION

Problems that the Invention is to Solve

Under such a situation, it is strongly desired to develop an anti-platelet agent with a high safety profile with a smaller adverse bleeding effect and with distinct pharmaceutical efficacies at not only acute phase but also chronic phase. Thus, it is an object of the invention to develop a platelet aggregation inhibitor or a P2Y12 inhibitor having a high pharmacological effect and a good balance between the pharmacological effect and the safety profile.

Means for Solving the Problems

Accordingly, the present inventors have conducted intensive studies with the aim of overcoming the above-mentioned problems and, as a result, found that a novel quinolone derivative has excellent platelet aggregation inhibitory activity or P2Y12 inhibitory activity and has excellent pharmacokinetics, and thereby accomplished the present invention.

That is, the present invention relates to a quinolone derivative represented by the following general formula (I) or a pharmaceutically acceptable salt thereof

[Symbols in the formula represent the following meanings,
$R^1$: cycloalkyl or lower alkylene-cycloalkyl,
wherein cycloalkyl in $R^1$ may be substituted,
$R^2$: —H or halogen,
$R^3$: —H, halogen, —$OR^0$ or —O-lower alkylene-aryl,
$R^0$: the same or different from each other and each represents —H or lower alkyl,
$R^4$: lower alkyl, halogeno-lower alkyl, lower alkylene-cycloalkyl, cycloalkyl or heterocyclic group,
wherein cycloalkyl and heterocyclic group in $R^4$ may respectively be substituted,
$R^5$: —$NO_2$, —CN, lower alkyl, lower alkenyl, halogeno-lower alkenyl, -L-$R^a$, —C(O)$R^0$, —O—$R^b$, —N($R^6$)$_2$, lower alkylene-N($R^6$)($R^c$), —N($R^6$)C(O)—$R^d$, lower alkylene-N($R^6$)C(O)—$R^d$, lower alkylene-N($R^0$)C(O)O-lower alkyl, —N($R^0$)C(O)N($R^0$)—$R^e$, lower alkylene-N($R^0$)C(O)N($R^0$)—$R^e$, —N($R^0$)S(O)$_2$N($R^0$)C(O)—$R^d$, —CH=NOH, cycloalkyl, heterocyclic group, (2,4-dioxo-1,3-thiazolidin-5-ylidene)methyl or (4-oxo-2-thioxo-1,3-thiazolidin-5-ylidene)methyl,
wherein cycloalkyl and heterocyclic group in $R^5$ may respectively be substituted,
$R^6$: H, lower alkyl, lower alkylene-$CO_2R^0$ or lower alkylene-P(O)(OR$^p$)$_2$,
wherein lower alkylene in $R^6$ may be substituted,
L: lower alkylene or lower alkenylene which may respectively be substituted
$R^a$: —$OR^0$, —CN, —O-lower alkylene-aryl, —O-lower alkylene-$CO_2R^0$, —C(O)$R^0$, —$CO_2R^0$, —C(O)NHOH, —C(O)N($R^6$)$_2$, —C(O)N($R^0$)-aryl, —C(O)N($R^0$)—S(O)$_2$-lower alkyl, —C(O)N($R^0$)—S(O)$_2$-aryl, —C(O)N($R^0$)—S(O)$_2$-heterocyclic group, —$NH_2OH$, —OC(O)$R^0$, —OC(O)-halogeno-lower alkyl, —P(O)(OR$^p$)$_2$, aryl or heterocyclic group,
wherein aryl and heterocyclic group in $R^a$ may be substituted,
$R^p$: $R^0$, lower alkylene-OC(O)-lower alkyl, lower alkylene-OC(O)-cycloalkyl, lower alkylene-OC(O)O-lower alkyl, lower alkylene-OC(O)O-cycloalkyl, or lower alkylene-heterocyclic group,
wherein heterocyclic group in $R^p$ may be substituted,
$R^b$: H, cycloalkyl, aryl, heterocyclic group, lower alkylene-$R^{ba}$ or lower alkenylene-$R^{ba}$, wherein lower alkylene, lower alkenylene, cycloalkyl, aryl and heterocyclic group in $R^b$ may be substituted,
$R^{ba}$: —$OR^0$, —O—Si(lower alkyl)$_3$, —$CO_2R^0$, —C(O)NHOH, —C(O)N($R^0$)$_2$, —C(O)N($R^0$)—S(O)$_2$-lower alkyl, —C(O)N($R^0$)—S(O)$_2$-aryl, —C(NH$_2$)=NOH, —C(NH$_2$)=NO—C(O)$R^0$, —C(NH$_2$)=NO—C(O)-lower alkylene-C(O)$R^0$, —$CO_2$-lower alkylene-aryl, —P(O)(OR$^p$)$_2$, —C(O)$R^0$, —C(O)-aryl, cycloalkyl, aryl or heterocyclic group,
wherein aryl and heterocyclic group in $R^{ba}$ may be substituted,
$R^c$: H, lower alkyl, lower alkylene-$OR^0$, lower alkylene-$CO_2R^0$, lower alkylene-C(O)NHOH, lower alkylene-C(O)N($R^0$)$_2$, lower alkylene-P(O)(OR$^p$)$_2$, lower alkylene-aryl, lower alkylene-heterocyclic group, aryl or heterocyclic group,
wherein lower alkylene, aryl and heterocyclic group in $R^c$ may be substituted,
$R^d$: $C_{1-7}$ alkyl, lower alkenyl, halogeno-lower alkyl, lower alkylene-$R^{da}$, lower alkenylene-$R^{da}$, cycloalkyl, aryl or heterocyclic group,
wherein lower alkylene, lower alkenylene, cycloalkyl, aryl and heterocyclic group in $R^d$ may be substituted,
$R^{da}$: —CN, —$OR^0$, —OC(O)$R^0$, —O-lower alkylene-$CO_2R^0$, —O-aryl, —$CO_2R^0$, —C(O)NHOH, —C(O)N($R^0$)$_2$, —$CO_2$-lower alkylene-N($R^0$)$_2$, —P(O)(OR$^p$)$_2$, —N($R^6$)$_2$, —N($R^0$)C(O)$R^0$, —C(O)N($R^0$)-aryl, —C(O)N($R^0$)-(lower alkylene which may be substituted with —$CO_2R^0$)-aryl, —N($R^0$)C(O)-aryl, —N($R^0$)C(O)—$OR^0$, —N($R^0$)C(O)—O-lower alkylene-aryl, —N($R^0$)S(O)$_2$-aryl, —S-heterocyclic group, —C(O)N($R^0$)-heterocyclic group, —N($R^0$)C(O)-heterocyclic group, cycloalkyl, aryl or heterocyclic group,
wherein cycloalkyl, aryl and heterocyclic group in $R^{da}$ may be substituted,
$R^e$: lower alkylene-$CO_2R^0$, lower alkylene-C(O)NHOH, lower alkylene-C(O)N($R^0$)$_2$, lower alkylene-heterocyclic group, aryl, heterocyclic group, —S(O)$_2$-aryl or —S(O)$_2$-heterocyclic group,
wherein aryl and heterocyclic group in $R^e$ may be substituted,
X: CH or N,
A: C($R^7$) or N,
$R^7$: —H and lower alkyl, or R$^4$ and R$^7$ may together form lower alkylene which may be substituted, with the proviso that 7-(cyclohexylamino)-1-ethyl-6-fluoro-4-oxo-1,4-dihydroquinoline-3-carbonitrile is excluded. The same shall apply hereinafter.]

In addition, this application relates to a pharmaceutical, particularly a P2Y12 receptor inhibitor and/or a platelet aggregation inhibitor, which comprises a quinolone derivative represented by the general formula (I) or a salt thereof as the active ingredient.

Further, this application also relates to the use of a compound represented by the formula (I) or a pharmaceutically acceptable salt thereof for the manufacture of a P2Y12 receptor inhibitor and/or a platelet aggregation inhibitor, and to a method for treating a circulatory organ system disease closely related to the thrombus formation by platelet aggregation, which comprises administering an effective amount of a compound represented by the formula (I) or a pharmaceutically acceptable salt thereof to a patient. That is, (1) a pharmaceutical composition which comprises a compound described in the general formula (I) or a pharmaceutically acceptable salt thereof and a pharmaceutically acceptable carrier.
(2) The pharmaceutical composition of (1) which is a platelet aggregation inhibitor.
(3) The pharmaceutical composition of (1) which is a P2Y12 inhibitor.
(4) Use of a compound described in the general formula (I) or a pharmaceutically acceptable salt thereof for the manufacture of a platelet aggregation inhibitor or a P2Y12 inhibitor.

Effect of the Invention

Since the compound of the present invention has excellent platelet aggregation inhibitory activity or P2Y12 inhibitory activity, it is useful as a pharmaceutical, particularly a platelet aggregation inhibitor or a P2Y12 inhibitor. Accordingly, the compound of the present invention is useful as a preventive and/or therapeutic agent for a circulatory organ system disease closely related to the thrombus formation by platelet aggregation, such as unstable angina, acute myocardial infarction and its secondary prevention, re-obstruction and re-stricture after hepatic coronary artery bypass surgery, PTCA operation or stent indwelling operation, hepatic coronary artery thrombolysis acceleration and re-obstruction prevention and the like ischemic diseases; transient cerebral ischemic attack (TIA) cerebral infarction, subarachnoid hemorrhage (vasospasm) and the like cerebrovascular accidents; chronic arterial occlusive disease and the like peripheral arterial diseases; and the like, and as an auxiliary agent at the time of cardiac surgical operation or vascular surgical operation.

BEST MODE FOR CARRYING OUT THE INVENTION

The following describes the present invention further in detail.

In this description, the "lower alkyl", "lower alkenyl", "lower alkylene" and "lower alkenylene" respectively mean hydrocarbon chains having from 1 to 6 carbon atoms which maybe in the straight chain or branched chain form, unless otherwise noted.

Accordingly, the "lower alkyl" means a $C_{1-6}$ alkyl, and illustrative examples thereof include methyl, ethyl, propyl, butyl, pentyl or hexyl, or structures isomers thereof such as isopropyl, tert-butyl or the like, preferably a $C_{1-5}$ alkyl, more preferably methyl, ethyl, propyl, isopropyl, butyl, isobutyl, tert-butyl or 3-pentyl.

The "lower alkenyl" means a $C_{2-6}$ alkenyl, and it may have two or more double bonds. Illustrative examples thereof include ethenyl, propenyl, butenyl, pentenyl, hexenyl, butadienyl and the like, of which preferred is a $C_{2-3}$ alkenyl and more preferred is ethenyl or propenyl.

The "lower alkylene" means a divalent group in which one hydrogen is removed from an optional position of the "lower alkyl", and is illustratively methylene, methylmethylene, ethylene, propylene, butylene or the like, preferably a $C_{1-4}$ alkylene, more preferably methylene, methylmethylene, ethylene or propylene.

The "lower alkenylene" means a divalent group in which one hydrogen is removed from an optional position of the "lower alkenyl", and is illustratively vinylene, propenylene, butenylene or the like, preferably a $C_{2-3}$ alkenylene, more preferably vinylene, propenylene.

The "halogen" means a monovalent group of halogen atom, and fluoro, chloro, bromo, iodo or the like may be cited illustratively, of which fluoro or chloro is preferred.

The "halogeno-lower alkyl" means a group in which at least one optional hydrogen atom of the aforementioned "lower alkyl" is substituted with the aforementioned "halogen", and illustrative examples thereof include trifluoromethyl, trifluoroethyl or the like, of which trifluoromethyl is preferred.

The "halogeno lower alkenyl" means a group in which at least one optional hydrogen atom of the aforementioned "lower alkenyl" is substituted with the aforementioned "halogen", and illustrative examples thereof include fluorovinyl, chlorovinyl or the like.

The "cycloalkyl" means a $C_{3-10}$ non-aromatic hydrocarbon ring, and it may form a bridged ring or a spiro ring, partially have an unsaturated bond or be condensed with benzene ring. However, when benzene ring is condensed, the linking hand is present on the non-aromatic ring. Illustrative examples thereof include cyclopropyl, cyclobutyl, cyclopentyl, cyclohexyl, cyclooctyl, cyclohexenyl, cyclooctdienyl, adamantly, norbornyl, indanyl having a linking hand at from the 1- to 3-position and the like. Preferred is cyclopropyl, cyclobutyl, cyclopentyl or cyclohexyl and more preferred is cyclopentyl or cyclohexyl.

The "aryl" means a monocyclic to tricyclic $C_{6-14}$ aromatic hydrocarbon ring, and illustrative examples thereof include phenyl, naphthyl or the like, of which phenyl is preferred. In addition, a $C_{5-8}$ cycloalkyl ring may be condensed. However, when a cycloalkyl ring is condensed, the linking hand is present on the aromatic ring. For example, it may form indanyl having a linking hand at from the 4- to 7-positions, or tetrahydronaphthyl having a linking hand at from the 5- to 8-positions.

The "hetero ring" is a general name which includes "aromatic hetero ring" and "non-aromatic hetero ring". The "aromatic hetero ring" means a monocyclic aromatic hetero ring which is a monocyclic 5- to 7-membered aromatic group containing from 1 to 4 of the same or different hetero atoms selected from the group consisting of nitrogen, oxygen and sulfur, a bicyclic aromatic hetero ring in which monocyclic aromatic hetero rings are condensed or a monocyclic aromatic hetero ring is condensed with benzene ring, or a tricyclic aromatic hetero ring in which a bicyclic aromatic hetero ring is condensed with a monocyclic aromatic hetero ring or benzene ring. Illustrative examples thereof include pyrrolyl, furyl, thienyl, imidazolyl, pyrazolyl, triazolyl, oxazolyl, thiazolyl, furazanyl, pyridyl, pyranyl, thiopyranyl, pyridazinyl, pyrimidinyl, pyrazyl, indolyl, isoindolyl, indolizinyl, benzofuryl, benzothienyl, benzoimidazolyl, indazolyl, benzotriazolyl, benzoxazolyl, benzothiazolyl, benzoxadiazonyl, quinolyl, isoquinolyl, chromenyl, benzothiopyranyl, phthalazinyl, naphthyridinyl, quinoxalinyl, quinazolinyl, cinnolinyl, benzodioxolyl, benzodioxinyl, benzodioxepinyl, carbazolyl and the like, and the nitrogen atom and/or sulfur atom constituting these rings may be oxidized. In addition, these rings may be partially saturated. Preferred is pyridyl, furyl, thienyl, indolyl or quinolyl.

The "non-aromatic hetero ring" means a saturated or partially saturated monocyclic 3- to 10-membered, preferably 5- to 7-membered, monocyclic non-aromatic hetero ring which contains from 1 to 4 hetero atoms selected from O, S and N, a bicyclic non-aromatic hetero ring in which monocyclic non-aromatic hetero rings are ring-condensed or a monocyclic non-aromatic hetero ring is ring-condensed with a monocyclic non-aromatic hetero ring, a $C_{5-8}$ cycloalkyl ring, benzene ring or an aromatic hero ring, or a tricyclic non-aromatic hetero ring in which a bicyclic non-aromatic hetero ring is ring-condensed with a $C_{5-8}$ cycloalkyl ring, benzene ring or an aromatic hero ring. These may form oxide or dioxide trough the oxidation of the S or N as the ring atom or may form a bridged ring or a spiro ring. Illustrative examples thereof include hydropyridyl, dihydropyrrolyl, dihydrooxazolyl, dihydrothiazolyl, dihydroimidazolyl, piperidyl, morpholinyl, thiomorpholinyl, piperazinyl, pyrazolidinyl, imidazolidinyl, pyrrolidinyl, oxazolidinyl, thiazolidinyl, azepanyl, homopiperazinyl, tetrahydrofuranyl, tetrahydropyranyl, tetrahydropyrimidinyl, chromanyl, dioxoranyl, homomorpholinyl and the like. Preferred is pyrrolidinyl, piperidinyl, morpholinyl, thiomorpholinyl or piperazinyl.

The term "may be substituted" means "not substituted" or "substituted with the same or different 1 to 5 substituent groups".

In the specification, the substituents acceptable as those for the phrase "which may be substituted" satisfactorily include those for routine use in the art as substituents for the individual groups. In addition, when two or more groups are present like the case of the $R^0$ of —$N(R^0)_2$, respective groups may be the same or different from each other.

As the acceptable substituent group of the "lower alkylene" which may be substituted in $R^6$, halogen may preferably be cited.

Preferably, a group selected from the following group $G^1$ may be cited as the acceptable substituent group of the "lower alkylene" and "lower alkenylene" which may be substituted in L; the "lower alkylene" and "lower alkenylene" which may be substituted in $R^b$; the "lower alkylene" which may be substituted in $R^c$; the "lower alkylene" and "lower alkenylene" which may be substituted in $R^d$; and the "lower alkylene", formed by $R^4$ and $R^7$, which may be substituted.

Group $G^1$: halogen, —$OR^0$, —$CO_2R^0$ and —$CO_2$-lower alkylene-aryl.

Preferably, a group selected from the following group $G^2$ may be cited as the acceptable substituent group of the "cycloalkyl" which may be substituted in $R^1$; the "cycloalkyl" which may be substituted in $R^4$; the "cycloalkyl" which may be substituted in $R^5$; the "cycloalkyl" which may be substituted in $R^b$; the "cycloalkyl", which may be substituted in $R^d$; and the "cycloalkyl", which may be substituted in $R^{da}$.

Group $G^2$: halogen, lower alkyl, —$OR^0$, —$CO_2R^0$ and —C(O)-aryl.

Preferably, a group selected from the following group $G^3$ may be cited as the acceptable substituent group of the "aryl" which may be substituted in $R^a$; the "aryl" which may be substituted in $R^b$; the "aryl" which may be substituted in $R^{ba}$; the "aryl" which may be substituted in $R^c$; the "aryl" which may be substituted in $R^{da}$; and the "aryl" which may be substituted in $R^e$.

Group $G^3$: halogen, —CN, lower alkyl, halogeno-lower alkyl, —$OR^0$, —O-halogeno-lower alkyl, —$CO_2R^0$ and —O-lower alkylene-$CO_2R^0$.

Preferably, a group selected from the following group $G^4$ may be cited as the acceptable substituent group of the "aryl" which may be substituted in $R^d$.

Group $G^4$: halogen, —CN, —$NO^2$, lower alkyl, halogeno-lower alkyl, —$OR^0$, —O-halogeno-lower alkyl, —$C(O)R^0$, —$CO_2R^0$, lower alkylene-$CO_2R^0$, —O-lower alkylene-$CO_2R^0$, —$OC(O)R^0$, —$N(R^0)_2$, —$S(O)_2$-lower alkyl, aryl and heterocyclic group.

However, the aryl and heterocyclic group in group $G^4$ may be substituted with a group selected from a group Q.

Group Q: halogen, lower alkyl, halogeno-lower alkyl, —$OR^0$, —O-halogeno-lower alkyl, oxo and —$CO_2R^0$.

Preferably, a group selected from the following group $G^5$ may be cited as the acceptable substituent group of the "heterocyclic group" which may be substituted in $R^4$; the "heterocyclic group" which may be substituted in $R^5$; the "heterocyclic group" which may be substituted in $R^a$; the "heterocyclic group which may be substituted in $R^b$; the "heterocyclic group" which may be substituted in $R^p$; the "heterocyclic group" which may be substituted in $R^{ba}$; and the "heterocyclic group" which may be substituted in $R^e$.

Group $G^5$: halogen, lower alkyl, halogeno-lower alkyl, —$OR^0$, —O-halogeno-lower alkyl, oxo, —$CO_2R^0$, lower alkylene-$C(O)R^0$, lower alkylene-$CO_2R^0$ and —$S(O)_2$-lower alkyl.

Preferably, a group selected from the following group $G^6$ may be cited as the acceptable substituent group of the "heterocyclic group" which may be substituted in $R^c$; and the "heterocyclic group" which may be substituted in $R^{da}$.

Group $G^6$: halogen, lower alkyl, halogeno-lower alkyl, —$OR^0$, —O-halogeno-lower alkyl, oxo, —$CO_2R^0$, lower alkylene-$C(O)_2R^0$, —$S(O)_2$-lower alkyl, aryl, —S-lower alkylene-aryl and heterocyclic group.

In this regard, the aryl and heterocyclic group in group $G^6$ may be substituted with a group selected from the aforementioned group Q.

Preferably, a group selected from the following group $G^7$ may be cited as the acceptable substituent group of the "heterocyclic group" which may be substituted in $R^d$.

Group $G^7$: halogen, nitro, lower alkyl, halogeno-lower alkyl, —$OR^0$, —O-halogeno-lower alkyl, oxo, —$CO_2R^0$, lower alkylene-$CO_2R^0$, —$N(R^0)_2$, —$S(O)_2$-lower alkyl, —$S(O)_2$-aryl, aryl, lower alkylene-aryl, heterocyclic group, lower alkylene-heterocyclic group and —S-lower alkylene-$CO_2R^0$. In this regard, the aryl and heterocyclic group in group $G^7$ may be substituted with a group selected from the aforementioned group Q.

A preferred embodiment in the present invention is shown in the following.

(a) Preferred as $R^1$ is cyclohexyl or cyclopropylmethyl, more preferably cyclohexyl.
(b) Preferred as $R^2$ is —F.
(c) Preferred as $R^3$ is —H, —OH or —F, more preferred is —H.
(d) Preferred as $R^4$ is lower alkyl or cycloalkyl, more preferably isopropyl, 3-pentyl or cyclopentyl, further preferred is isopropyl, 3-penthyl or cyclopentyl.
(e) Preferred as $R^5$ is —$N(R^0)C(O)$-lower alkylene-$CO_2R^0$, —$N(R^0)C(O)$-lower alkenylene-$CO_2R^0$, lower alkylene-$CO_2R^0$, lower alkenylene-$CO_2R^0$, —O-lower alkenylene-$CO_2R^0$, —O-(lower alkylene which may be substituted with —CO$_2$R$^O$)-aryl, —O-lower alkenylene-CO$_2$R$^O$, —O-(lower alkenylene which may be substituted with —CO$_2$R$^O$)-aryl or —O-lower alkenylene-tetrazolyl, more preferably —N(R$^O$)C(O)-lower alkylene-CO$_2$R$^O$, lower alkylene-CO$_2$R$^O$, lower alkenylene-CO$_2$R$^O$, —O-lower alkylene-CO$_2$R$^O$, —O-(lower alkylene which may be substituted with —CO$_2$R$^O$)-aryl or —O-lower alkenylene-CO$_2$R$^O$, further preferably lower alkenylene-CO$_2$R$^O$ or —O-lower alkylene-CO$_2$R$^O$.
(f) Preferred as X is CH.
(g) Preferred as A is CH.
Further, a compound consisting of a combination of the preferred groups of the above-mentioned (a) to (g) is more preferable.

Also, another preferred embodiment of the compound of the present invention represented by the general formula (I) is shown in the following.
(1) The compound described in the general formula (I), wherein X is CH.
(2) The compound described in (1), wherein R$^3$ is —H, —OH or —F.
(3) The compound described in (2), wherein A is CH.
(4) The compound described in (3), wherein R$^1$ is cyclohexyl or cyclopropylmethyl.
(5) The compound described in (4), wherein R$^2$ is —F.
(6) The compound described in (5), wherein R$^4$ is lower alkyl or cycloalkyl.
(7) The compound described in (6), wherein R$^5$ is —N(R$^O$)C(O)-lower alkylene-CO$_2$R$^O$, lower alkylene-CO$_2$R$^O$, lower alkenylene-CO$_2$R$^O$, —O-lower alkylene-CO$_2$R$^O$, —O-(lower alkylene which may be substituted with —CO$_2$R$^O$)-aryl or —O-lower alkenylene-CO$_2$R$^O$.
(8) A compound described in the general formula (I), which is selected from the group consisting of
4-{[7-(cyclohexylamino)-1-cyclopentyl-6-fluoro-4-oxo-1,4-dihydroquinolin-3-yl]amino}-4-oxobutanoic acid,
5-{[7-(cyclohexylamino)-1-cyclopentyl-6-fluoro-4-oxo-1,4-dihydroquinolin-3-yl]amino}-5-oxopentanoic acid,
(2E)-3-[7-(cyclohexylamino)-1-cyclopentyl-6-fluoro-4-oxo-1,4-dihydroquinolin-3-yl]acrylic acid,
(2S)-2-{[7-(cyclohexylamino)-1-cyclopentyl-6-fluoro-4-oxo-1,4-dihydroquinolin-3-yl]oxy}-3-phenylpropanoic acid,
(2E)-3-[7-(cyclohexylamino)-6-fluoro-1-isopropyl-4-oxo-1,4-dihydroquinolin-3-yl]acrylic acid,
(2S)-2-{[7-(cyclohexylamino)-6-fluoro-1-isopropyl-4-oxo-1,4-dihydroquinolin-3-yl]oxy}-3-phenylpropanoic acid,
(2S)-2-{[7-(cyclohexylamino)-1-cyclopentyl-6-fluoro-4-oxo-1,4-dihydroquinolin-3-yl]oxy}propanoic acid, and
(2S)-2-{[7-(cyclohexylamino)-6-fluoro-1-isopropyl-4-oxo-1,4-dihydroquinolin-3-yl]oxy}propanoic acid,
or a pharmaceutically acceptable salt thereof.

Also, there is a case in which the compounds of the present invention form salts, and such salts are included in the compounds of the present invention as long as they are pharmaceutically acceptable salts. Illustrative examples thereof include acid addition salts with inorganic acids (e.g., hydrochloric acid, hydrobromic acid, hydriodic acid, sulfuric acid, nitric acid, phosphoric acid and the like), or organic acids (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, glutamic acid and the like), salts with inorganic bases including metals (e.g., sodium, potassium, calcium, magnesium and the like) or with organic bases (e.g., methylamine, ethylamine, ethanolamine, lysine, ornithine and the like), ammonium salts and the like.

In addition, the compounds of the present invention may have an asymmetric carbon atom in some cases depending on the kind of substituent groups, and optical isomers based on this may be present. The present invention includes all of the mixtures and isolated forms of these optical isomers. Also, tautomers are present in the compounds of the present invention in some cases, and the present invention includes separated forms of these isomers or mixtures thereof. In addition, a labeled substance, namely a compound in which at least one atom of the compound of the present invention is replaced by a radioisotope or non-radioactive isotope, is also included in the present invention.

In addition, various types of hydrate and solvate and polymorphism of the compound of the present invention or a pharmaceutically acceptable salt thereof are also included. In this connection, as a matter of course, the compounds of the present invention are not limited to the compounds described in the Examples which are described later, and all of the derivatives represented by the formula (I) and pharmaceutically acceptable salts thereof are included therein.

In this connection, all of the compounds which are converted in the living body into the compounds of the present invention represented by the aforementioned general formula (I), so-called prodrugs, are also included in the compounds of the present invention. As the groups which can form prodrugs of the compounds of the present invention, the groups described in *Prog. Med.*, 5: 2157-2161 (1985), and the groups described in "Iyakuhin no Kaihatsu (Development of Medicines)", vol. 7 Bunshi Sekkei (Molecular Design), pp. 163-198, published by Hirokawa Shoten in 1990, may be exemplified.
(Step A)

This step is a step in which a compound (I-a) of the present invention is produced by reducing a compound (1).

As the reduction reaction of this step, a carboxylic acid or ester reduction reaction generally used by those skilled in the art may be employed. For example, this may be carried out under cooling to heating reflux using equimolar to excess amount of a reducing agent such as lithium aluminum hydride, diisobutylaluminum hydride, sodium borohydride or the like, in a reaction inert solvent, for example aromatic hydrocarbons such as benzene, toluene, xylene, ethers such as diethyl ether, tetrahydrofuran (THF), dioxane, halogenated hydrocarbons such as dichloromethane, 1,2-dichloroethane, chloroform, N,N-dimethylformamide (DMF), N,N-dimethylacetamide (DMA), N-methylpyrrolidone (NMP), dimethyl sulfoxide (DMSO), acetonitrile, alcohols such as methanol, ethanol, and water. In addition, when the compound (1) is a carboxylic acid wherein R$^O$ is —H, the carboxylic acid may also be reduced after converting it into a reactive derivative. As the reactive derivative of carboxylic acid, an acylimidazole obtained by reaction with 1,1'-carbonyldiimidazole (CDI), a mixed acid anhydride obtained by reaction with isobutyl chloroformate, etc., and the like may be cited.
(Step B)

This step is a step in which a compound (I-b) of the present invention is produced by oxidizing the compound (I-a) of the present invention.

In the oxidation reaction of this step, an alcohol oxidation reaction generally used by those skilled in the art may be used. For example, this may be carried out under room temperature to heating using equivalent to excess amount of manganese dioxide as an oxidizing agent, in a solvent such as the aforementioned aromatic hydrocarbons, halogenated hydrocarbons or the like.

(Step C)

This step is a step in which a compound (I-c) of the present invention is produced by subjecting the compound (I-b) of the present invention to an oxidation rearrangement reaction (Baeyer-Villiger) and then to hydrolysis.

The oxidation rearrangement reaction of this step may be carried out under room temperature to heating using equivalent to excess amount of m-chloroperbenzoic acid, peracetic acid, aqueous hydrogen peroxide or the like as the oxidizing agent, in a reaction inert solvent such as the aforementioned aromatic hydrocarbons, halogenated hydrocarbons, acetic acid, water or the like.

The hydrolysis reaction of this step may be carried out using an ester hydrolysis reaction generally used by those skilled in the art. For example, it may be carried out under cooling to heating in a reaction inert solvent such as the aforementioned aromatic hydrocarbons, ethers, halogenated hydrocarbons, alcohols, DMF, DMA, NMP, DMSO, pyridine, water or the like in the presence of mineral acid such as sulfuric acid, hydrochloric acid, hydrobromic acid or the like or organic acid such as formic acid, acetic acid or the like, or in the presence of a base such as lithium hydroxide, sodium hydroxide, potassium hydroxide, potassium carbonate, sodium carbonate, cesium carbonate or ammonia or the like.

Depending on the kind of the compounds, the compound (I-c) may be obtained in some cases by advancing to the hydrolysis at a stroke in the oxidation rearrangement reaction.

(Step D)

This step is a step in which a compound (I-d) of the present invention is produced by subjecting the compound (I-c) of the present invention to a nucleophilic substitution reaction.

The nucleophilic substitution reaction of this step may be carried out using an equivalent to excess amount of a compound (2), under room temperature to heating in a solvent such as the aforementioned aromatic hydrocarbons, ethers, halogenated hydrocarbons, DMF, DMA, NMP, DMSO or the like, in the presence of a base such as potassium carbonate, tert-butoxy potassium, sodium hydride, triethylamine or the like.

Second Production Method

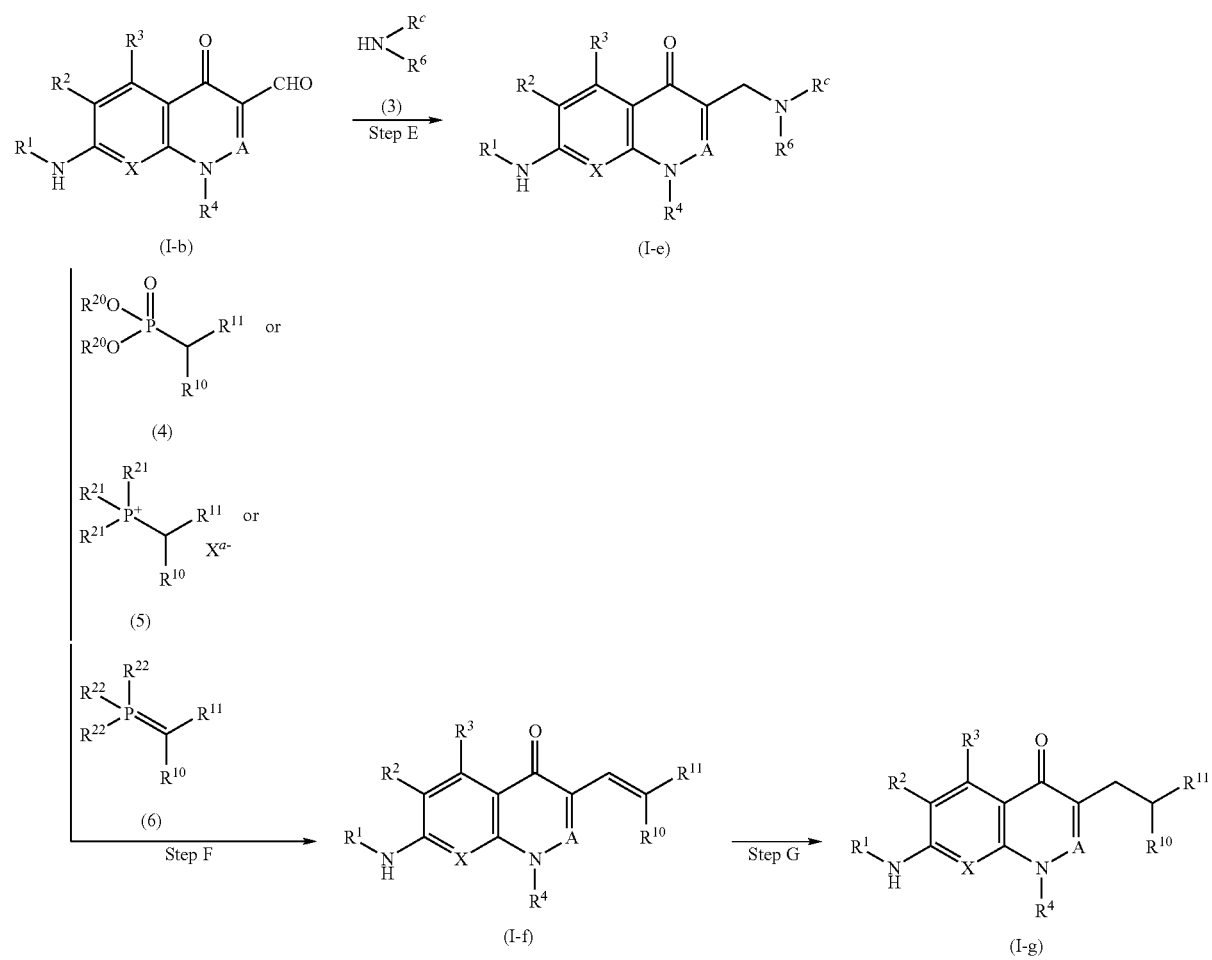

(In the formulae, $R^{10}$ and $R^{11}$ mean —H, halogen, —$CO_2R^0$ or lower alkyl or aryl which may respectively be substituted, and $R^{20}$ mean a residual part of the Horner-Emmons reagent (4), $R^{21}$ mean a residual part of the phosphonium salt (5), $X^{a-}$ mean $Cl^-$, $Br^-$ or the like counter anion, and $R^{22}$ mean a residual part of the ylide compound (6).)

(Step E)

This step is a step in which a compound (I-e) of the present invention is produced by subjecting the compound (I-b) of the present invention to a reductive alkylation reaction.

The reductive alkylation reaction of this step may use a reductive alkylation reaction generally used by those skilled in the art. For example, the method described in "Jikken Kagaku Koza (Experimental Chemistry Course)" edited y The Chemical Society of Japan, Vol. 20 (1992) (Maruzen) or the like may be cited. It is desirable to carry out the reaction under cooling to heating reflux using the reducing agent such as sodium borohydride, sodium triacetoxy borohydride, or the like without solvent or in a reaction inert solvent such as the aforementioned halogenated hydrocarbons, aromatic hydrocarbons, ethers, alcohols, esters including ethyl acetate or the like, acetic acid or the like. Depending on the compounds, it is advantageous in some cases to carry out the reaction in the presence of organic acid such as sulfuric acid, hydrochloric acid, hydrobromic acid or the like mineral acid, formic acid, acetic acid or the like or Lewis acid such as titanium(IV) chloride, tetraisopropyl orthotitanate or the like. In addition, it may also be carried out under room temperature to heating in an atmosphere of hydrogen under ordinary pressure to pressurization using, for example, palladium-carbon, rhodium-carbon, Raney nickel, platinum or the like as the catalyst, in a reaction inert solvent such as the aforementioned aromatic hydrocarbons, esters, ethers, halogenated hydrocarbons, DMF, DMA, NMP, acetonitrile, acetic acid or the like. Depending on the compound, it is advantageous in some case in effecting smooth progress of the reaction to allow it to react with an acid (preferably hydrochloric acid, acetic acid or the like).

(Step F)

This step is a step in which a compound (I-f) of the present invention is produced by subjecting the compound (I-b) of the present invention to the Horner-Emmons or Wittig reaction.

The Horner-Emmons or Wittig reaction of this step may use a method generally used by those skilled in the art. For example, when the Horner-Emmons reagent (4) or phosphonium salt (5) is used, the reaction may be carried out under cooling to heating using potassium carbonate, tert-butoxy potassium, sodium hydride, n-butyl n-butyl lithium or the like alkyl lithium or the like as a base, in a solvent such as the aforementioned aromatic hydrocarbons, ethers, halogenated hydrocarbons, DMF, DMA, NMP, DMSO, acetonitrile or the like. Also, when the ylide compound (6) is used, the reaction may be carried out under cooling to heating in a solvent such as the aforementioned aromatic hydrocarbons, ethers, halogenated hydrocarbons, DMF, DMA, NMP, DMSO, acetonitrile or the like.

(Step G)

This step is a step in which a compound (I-g) of the present invention is produced by reducing the double bond of the compound (I-f) of the present invention.

The reduction reaction of this step may use a method generally used by those skilled in the art. For example, it may also be carried out under room temperature to heating in an atmosphere of hydrogen under ordinary pressure to pressurization using palladium-carbon, Raney nickel, platinum or the like as the catalyst, in a reaction inert solvent such as the aforementioned aromatic hydrocarbons, esters, ethers, halogenated hydrocarbons, DMF, DMA, NMP, acetic acid or the like. Depending on the compound, it is advantageous in some case in effecting smooth progress of the reaction to allow it to react with an acid (preferably hydrochloric acid, acetic acid or the like).

Third Production Method

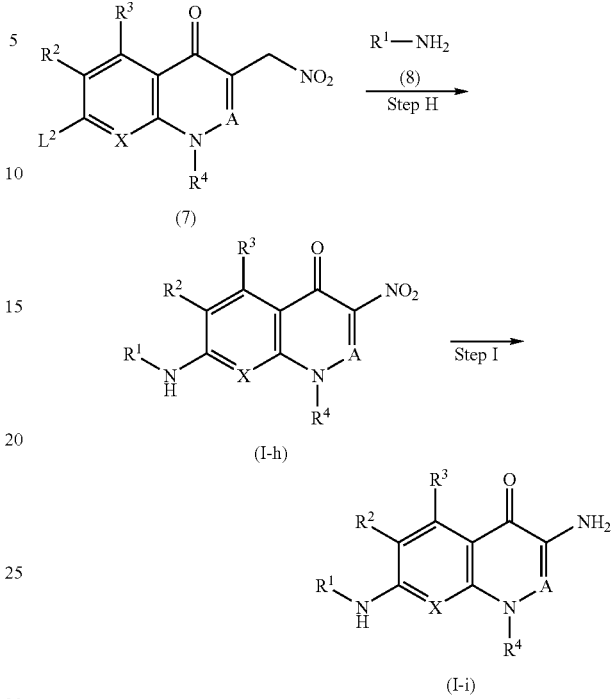

(In the formulae, $L^2$ represents a leaving group such as halogen, —O-methanesulfonyl, —O-p-toluenesulfonyl or the like. The same shall apply hereinafter.)

(Step H)

This step is a step in which a compound (I-h) of the present invention is produced by subjecting a compound (7) to a nucleophilic substitution reaction.

The nucleophilic substitution reaction of this step may be carried out using a compound (7) and compound (8) in equimolar amounts, or one of them in an excess amount, under room temperature to heating without solvent or in a solvent such as the aforementioned aromatic hydrocarbons, ethers, halogenated hydrocarbons, DMF, DMSO, esters including ethyl acetate or the like, acetonitrile, alcohols or the like. Depending on the compounds, it is advantageous in some case to carry out in the presence of an organic base (triethylamine, diisopropylethylamine, N-methylmorpholine, pyridine, 4-(N,N-dimethylamino)pyridine or the like is suitably used) or a metal salt base (potassium carbonate, cesium carbonate, sodium hydroxide, potassium hydroxide, sodium hydride, tert-butoxy potassium or the like is suitably used).

(Step I)

This step is a step in which a compound (I-i) of the present invention is produced by reducing the compound (I-h) of the present invention.

The nitro-reducing reaction of this step may use a method generally used by those skilled in the art. For example, it may also be carried out under room temperature to heating in an atmosphere of hydrogen under ordinary pressure to pressurization using palladium-carbon, Raney nickel, platinum or the like as the catalyst, in a reaction inert solvent such as the aforementioned aromatic hydrocarbons, esters, ethers, halogenated hydrocarbons, DMF, DMA, NMP, acetic acid or the like. Depending on the compound, it is advantageous in some case in effecting smooth progress of the reaction to allow it to react with an acid (preferably hydrochloric acid, acetic acid or the like).

Fourth Production Method

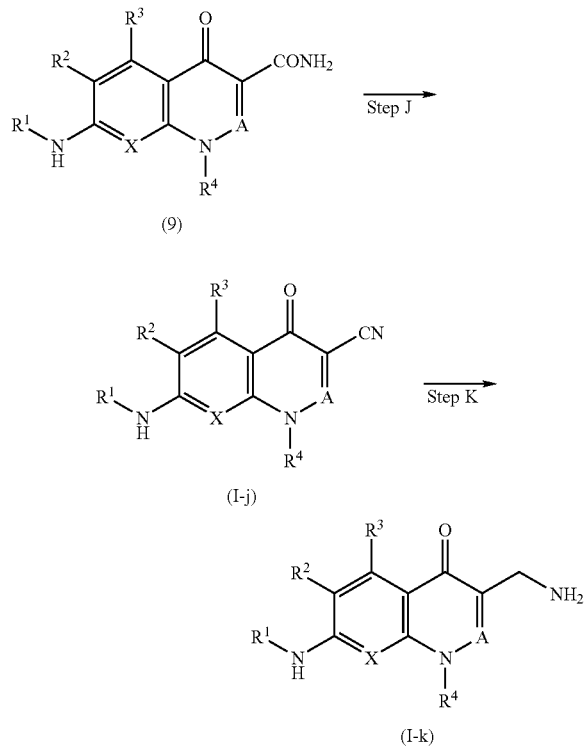

Fifth Production Method

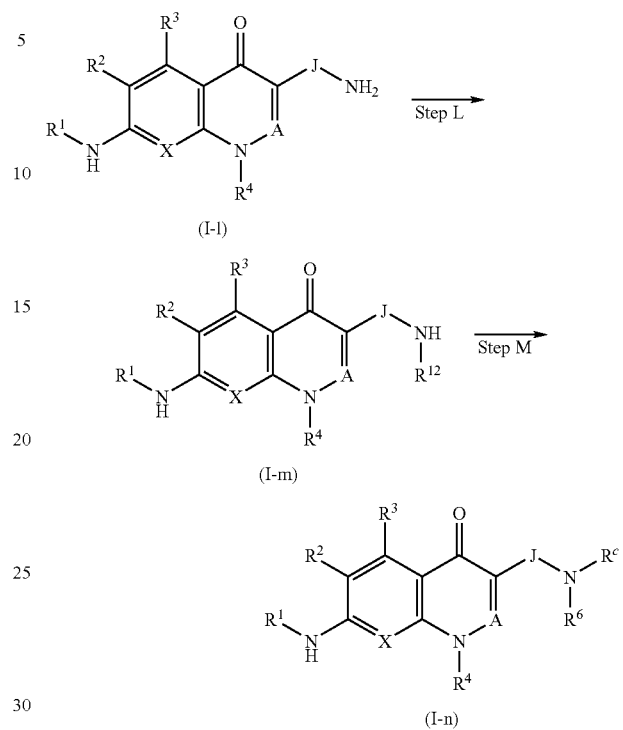

(Step J)

This step is a step in which a compound (I-j) of the present invention is produced by dehydrating a compound (9).

The dehydration reaction of this step may use a method which may be generally used in the amide dehydration reaction by those skilled in the art. For example, it may be carried out under room temperature to heating using diphosphorus pentoxide, phosphorus oxychloride, trifluoroacetic anhydride or the like as a dehydrating agent, without solvent or in a reaction inert solvent such as aromatic hydrocarbons, halogenated hydrocarbons, ethers or the like. However, when trifluoroacetic anhydride is used as the dehydrating agent, the 7-position amino group of quinolone is trifluoroacetylated in some cases depending on the kind of the compound, so that there is a case of requiring hydrolysis for the after-treatment. A method which is generally used in the amide hydrolysis by those skilled in the art may be employed in the hydrolysis.

(Step K)

This step is a step in which a compound (I-k) of the present invention is produced by reducing the compound (I-j) of the present invention.

The nitrile-reducing reaction of this step may also be carried out under room temperature to heating in an atmosphere of hydrogen under ordinary pressure to pressurization using palladium-carbon, Raney nickel, platinum or the like as the catalyst, in a reaction inert solvent such as the aforementioned aromatic hydrocarbons, esters, ethers, halogenated hydrocarbons, DMF, DMA, NMP, acetic acid or the like. Depending on the compound, it is advantageous in some case in effecting smooth progress of the reaction to allow it to react with an acid (preferably hydrochloric acid, acetic acid or the like).

(In the formulae, J represents single bond or lower alkylene, and $R^{12}$ is $R^6$ or $R^c$. The same shall apply hereinafter.)

(Step L)

This step is a step in which a compound (I-m) of the present invention is produced by subjecting the compound (I-l) of the present invention to a nucleophilic substitution reaction or reductive alkylation reaction.

The nucleophilic substitution reaction and reductive alkylation reaction of this step may be carried out respectively in the same manner as in the step D and step E.

(Step M)

This step is a step in which a compound (I-n) of the present invention is produced by subjecting the compound (I-m) of the present invention to a nucleophilic substitution reaction or reductive alkylation reaction.

The nucleophilic substitution reaction and reductive alkylation reaction of this step may be carried out respectively in the same manner as in the step D and step E.

Sixth Production Method

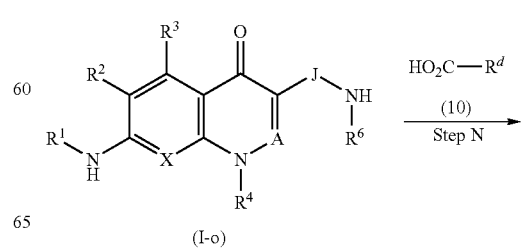

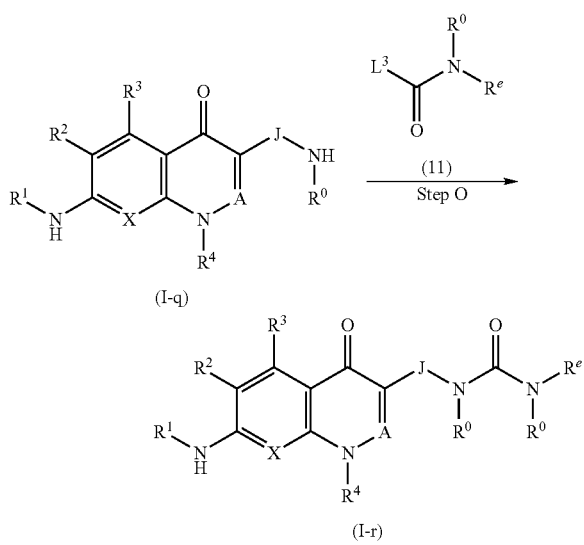

(I-p)

(Step N)

This step is a step in which a compound (I-p) of the present invention is produced by an amidation reaction of a compound (I-o) of the present invention with a compound (10) or a reactive derivative thereof.

The amidation reaction of this step may use an amidation which may be generally used by those skilled in the art. Particularly, a method which uses condensing agent such as carbonyldiimidazole (CDI), 1-ethyl-3-(dimethylaminopropyl)carbodiimide hydrochloride (WSC.HCl), dicyclohexylcarbodiimide, diphenylphosphoryl azide, diethylphosphoryl cyanide or the like, a method which is carried out by way of a mixed acid anhydride using isobutyl chloroformate, ethyl chloroformate and the like, and a method which is carried out by way of an acid halide using thionyl chloride, phosphorus oxychloride or the like are suitable. The reaction conditions may be optionally selected depending on the reactive derivative and condensing agent to be used, and this is generally carried out under cooling, under cooling to room temperature, or under room temperature to heating in a reaction inert solvent such as halogenated hydrocarbons, aromatic hydrocarbons, ethers, DMF, DMSO or the like. Depending on the reaction, it is advantageous in some case to carry out in the presence of an organic base (triethylamine, diisopropylethylamine, N-methylmorpholine, pyridine, 4-(N,N-dimethylamino)pyridine or the like is suitably used) or a metal salt base (potassium carbonate, cesium carbonate or the like is suitably used).

Seventh Production Method

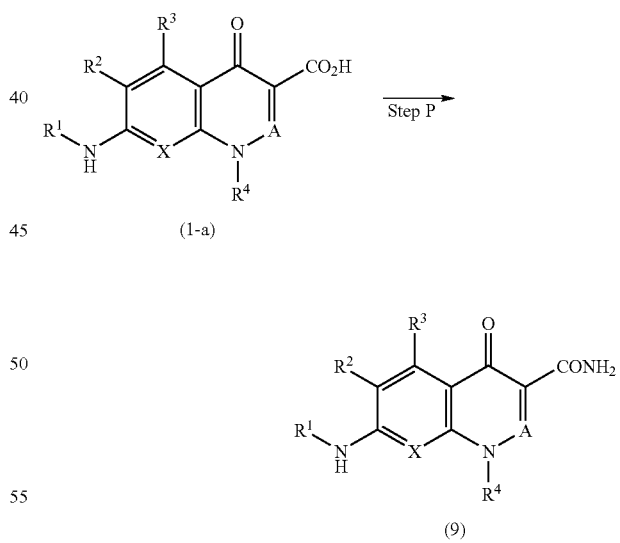

(In the formulae, $L^3$ represents a leaving group such as —O-lower alkyl, —O-p-nitrophenyl or the like.)

(Step O)

This step is a step in which a compound (I-r) of the present invention is produced by urea formation of a compound (I-q) of the present invention.

The urea formation reaction may be carried out under room temperature to heating using equivalent amounts of the compound (I-q) and a compound (11), or one f them in an excess amount, in a reaction inert solvent such as aromatic hydrocarbons, halogenated hydrocarbons, ethers, DMF, DMSO or the like. Depending on the reaction, it is advantageous in some case to carry out in the presence of an organic base (triethylamine, diisopropylethylamine, N-methylmorpholine, pyridine, 4-(N,N-dimethylamino)pyridine, 1,8-diazabicyclo[5.4.0]-7-undecene or the like is suitably used) or a metal salt base (potassium carbonate, cesium carbonate or the like is suitably used).

In addition, several compounds represented by the formula (I) may also be produced from the compounds obtained in the above manner by optionally combining steps such as conventionally known alkylation, acylation, substitution reaction, oxidation, reduction, hydrolysis and the like, which may be generally employed by those skilled in the art. Particularly, the compounds (I-a), (I-b), (I-c), (I-h), (I-i) and (I-j) of the present invention are also useful as the synthesis intermediates of the compounds of the present invention.

(Synthesis of Starting Compounds)

The starting compounds to be used in the production of the compound (I) of the present invention may be synthesized using the following methods, conventionally known methods or modified methods thereof (Starting Material Synthesis 1)

The compound (1-a) may be produced using the method described in the Patent Reference 7 or a modified method thereof (Step P)

This step is a step in which the compound (9) is produced by the amidation of the compound (1-a).

Regarding the amidation reaction of this step, it may be produced for example by the method described in the step N.

(Starting Material Synthesis 2)

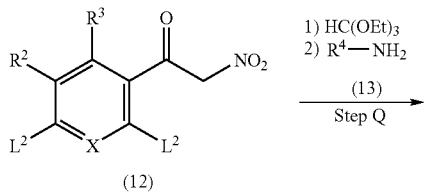

(12)

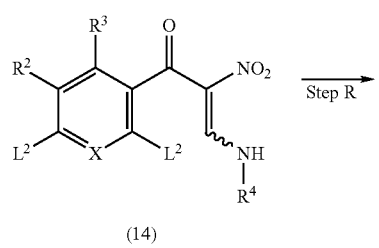

(14)

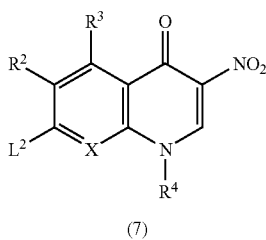

(7)

(Step Q)

This step is a step in which a compound (14) is produced by a condensation reaction of a compound (12) with an orthoformic ester and subsequent addition elimination reaction by a compound (13).

The condensation reaction of this step by an orthoformic ester may be carried out under room temperature to heating by using a reagent which captures alcohols generated from the orthoformic ester as a solvent such as acetic anhydride, or by using a reagent which captures alcohols generated from the orthoformic ester in a reaction inert solvent such as halogenated hydrocarbons, ethers, aromatic hydrocarbons, DMF, DMSO, esters, acetonitrile or the like.

The addition elimination reaction after the above-mentioned condensation reaction may be carried out under cooling, room temperature or heating in a reaction inert solvent such as alcohols, halogenated hydrocarbons, ethers, aromatic hydrocarbons, DMF, DMSO or the like. In this connection, the reaction may also be carried out using excess amount of the compound (13). Depending on the compounds, it is advantageous in some case to carry out in the presence of an organic base (triethylamine, diisopropylethylamine, N-methylmorpholine, pyridine, 4-(N,N-dimethylamino)pyridine or the like is suitably used) or a metal salt base (potassium carbonate, cesium carbonate, sodium hydroxide, potassium hydroxide, sodium hydride, tert-butoxy potassium or the like is suitably used).

(Step R)

This step is a step in which a compound (7) is produced by an intramolecular cyclization reaction of the amino group of the compound (14).

The intramolecular cyclization reaction of this step may be carried out under cooling, room temperature or heating in a reaction inert solvent such as halogenated hydrocarbons, ethers, aromatic hydrocarbons, DMF, DMSO or the like. Depending on the compounds, it is advantageous in some case to carry out in the presence of an organic base (triethylamine, diisopropylethylamine, N-methylmorpholine, pyridine, 4-(N,N-dimethylamino)pyridine, 1,8-diazabicyclo[5.4.0]-7-undecene or the like is suitably used) or a metal salt base (potassium carbonate, cesium carbonate, sodium hydroxide, potassium hydroxide, sodium hydride, tert-butoxy potassium or the like is suitably used).

The compound of the present invention produced in this manner is isolated and purified directly as free or as a salt thereof by applying a salt formation treatment in the usual way. The isolation and purification are carried out by employing general chemical operations such as extraction, concentration, evaporation, crystallization, filtration, recrystallization, various types of chromatography and the like.

Various types of isomers may be isolated in the usual way making use of the difference in the physicochemical properties between isomers. For example, a racemic mixture may be converted into an optically pure isomer by a general racemic resolution method including for example converting to diastereomer salts with optically active acid such as a tartaric acid and subsequent optical resolution. Also, a diastereomer mixture may be separated, for example, by a fractional recrystallization or various types of chromatography. In addition, an optically active compound may also be produced using an appropriate optically active compound as the starting material.

The pharmaceutical composition which contains one or more of the compounds of the present invention or pharmaceutically acceptable salts thereof as the active ingredient is prepared using carriers and fillers and other additive agents generally used in preparing pharmaceuticals.

Its administration may be in the form of either oral administration by tablets, pills, capsules, granules, powders, solutions and the like, or parenteral administration by intravenous, intramuscular or the like injections, suppositories, percutaneous preparations, transnasal preparations, inhalations and the like. Its dose is optionally decided by taking into consideration symptom, age, sex and the like of the object to be treated in response to each case, but in the case of oral administration, it is generally approximately from 0.001 mg/kg to 100 mg/kg per day per adult, and this is administered in one portion or by dividing into 2 to 4 portions. Also, in the case of intravenous administration, it is administered within the range of from 0.0001 mg/kg to 10 mg/kg per adult, once or two or more times per day. In addition, in the case of transnasal administration, it is administered within the range of from 0.0001 mg/kg to 10 mg/kg per adult, once or two or more times per day.

As the solid composition for oral administration by the present invention, tablets, powders, granules and the like are used. In such a solid composition, one or more active substances are mixed with at least one inert diluent such as lactose, mannitol, glucose, hydroxypropylcellulose, microcrystalline cellulose, starch, polyvinyl pyrrolidone, aluminum magnesium silicate or the like. In accordance with the usual way, the composition may contain additive agents other than the inert diluent, such as lubricant (e.g., magnesium stearate or the like), disintegrating agent (e.g., calcium cellulose glycolate or the like), a stabilizing agent, solubilizing agent and the like. When necessary, tablets or pills may be coated with a sugar coating or film of a gastric or enteric substance, such as of sucrose, gelatin, hydroxypropylcellulose, hydroxypropylmethylcellulose phthalate or the like.

The liquid composition for oral administration includes pharmaceutically acceptable emulsions, solutions, suspensions, syrups, elixirs and the like and contains a generally used inert diluent such as purified water or ethanol EtOH). In addition to the inert diluent, this composition may contain a moistening agent, a suspending agent and the like auxiliary agents, as well as sweeteners, flavors, aromatics and antiseptics.

As the injections for parenteral administration, aseptic aqueous or non-aqueous solutions, suspensions and emulsions are included. As the aqueous solutions and suspensions, for example, distilled water for injection and physiological saline are included. As the non-aqueous solutions and suspensions, for example, there are propylene glycol, polyethylene glycol, olive oil or the like plant oil, EtOH or the like alcohols, polysorbate 80 and the like. Such a composition may further contain auxiliary agents such as an antiseptic, a moistening agent, an emulsifying agent, a dispersing agent, a stabilizing agent, a solubilizing agent or the like. These are sterilized for example by filtration through a bacteria retaining filter, blending of a germicide or irradiation. These may also be used by producing sterile solid compositions and dissolving them in sterile water or a sterile solvent for injection prior to their use.

Pharmacological activities of the compounds of the present invention were verified by the following tests.

Test Method (1) Human Platelet Aggregation Inhibition Activity Measuring Test

A blood sample was collected from a healthy volunteers (male adult) using a syringe containing ¹⁄₁₀th volume of 3.8% sodium citrate solution and centrifuged at 160×g for 10 minutes, thereby separating platelet rich plasma (PRP) of the supernatant. Remaining blood after the collection of PRP was centrifuged at 1,800×g for 10 minutes to separate platelet poor plasma (PPP). The number of platelets in the PRP was measured by an automatic blood cell counter (MEK-6258, Nihon Kohden Corp.), and then the number of platelets was adjusted to $3 \times 10^8$/ml by adding PPP to PRP and used in the following test. The ADP as an inducer of platelet aggregation was purchased from MC Medical. Platelet aggregation was measured using an aggregometer (MCM Hematracer 212; MC Medical). That is, 80 μl of PRP of $3 \times 10^8$ platelets/ml and 10 μl of a test compound solution or a solvent (10% DMSO or 10% DMSO-9% hydroxypropyl-β-cyclodextrin-4.5% d-mannitol) were incubated at 37° C. for 1 minute, and then 10 μl of ADP (50 μM) was added thereto to induce platelet aggregation, and changes in transmitted light were recorded for 5 minutes. The inhibition ratio was calculated using the area under platelet aggregation curve as an index. The results at 10 μM (final concentration) of compounds of the present invention are shown in Table 1.

In this connection, REx represents reference example number, and Ex Example compound number. In addition, Reference Examples 1 and 2 are the Example compounds described in the aforementioned Patent Reference 7, and were produced in accordance with the method described in said patent reference.

Reference Example 1

Example 467 of Patent Reference 7

4-({[7-(cyclohexylamino)-1-cyclopentyl-6-fluoro-4-oxo-1,4-dihydroquinolin-3-yl]carbonyl}amino)butanoic Acid Reference Example 2

Example 6 of Patent Reference 7

({[7-(cyclohexylamino)-1-cyclopentyl-6-fluoro-4-oxo-1,4-dihydroquinolin-3-yl]carbonyl}amino)acetic Acid

TABLE 1

| Compound to be tested | Inhibition % |
|---|---|
| REx 1 | 64 |
| REx 2 | 79 |
| Ex 2 | 93 |
| Ex 76 | 94 |
| Ex 80 | 92 |
| Ex 82 | 89 |
| Ex 87 | 92 |
| Ex 114 | 85 |
| Ex 125 | 91 |
| Ex 146 | 83 |
| Ex 202 | 94 |
| Ex 261 | 97 |
| Ex 271 | 91 |
| Ex 297 | 89 |
| Ex 321 | 93 |
| Ex 354 | 85 |
| Ex 380 | 89 |
| Ex 407 | 84 |

Test Method (2) Substitution Test for the Binding of Human P2Y12 with 2-methylthio-ADP (2-MeS-ADP)

A C6-15 cell was inoculated into a 10 cm petri dish to a density of to $1 \times 10^6$ cells using DMEM medium and cultured for 1 day, and then 8 μg of a plasmid pEF-BOS-dfhr-human P2Y12 and 0.8 μg of pEF-BOS-neo (Nucleic Acid Res., 18, 5322, 1990) were gene-transferred using a transfection reagent (LipofectAMINE 2000; mfd. by GIBCO BRL).

24 hours after the aforementioned gene transfer operation, the gene-transferred cells were recovered, suspended in DMEM medium supplemented with 0.6 mg/ml of G 418 (mfd. by GIBCO BRL) and then serially diluted and inoculated again in a 10 cm petri dish. The colonies appeared after 2 weeks were individually obtained and used in the following test as P2Y12 protein expression $C_{6-15}$ cells (WO 02/36631, Mol. Pharmacol., 60, 432, 2001).

After culturing the P2Y12 protein expression $C_{6-15}$ cells, the cells were recovered. The cells were washed with PBS, and then suspended in 20 mM Tris-HCl (pH 7.4) containing 5 mmol/l of EDTA and a protease inhibitor cocktail set Complete™ (mfd. by Boehringer-Mannheim) and homogenized using Polytron. After carrying out ultracentrifugation, the precipitate was suspended in 50 mM Tris-HCl (pH 7.4) containing 1 mM EDTA, 100 mM NaCl and Complete™, and this was used as a membrane fraction.

A 100 µl portion of the P2Y12 protein expression C6-15 cell membrane fraction (100 µg/ml) obtained in the above was mixed with 1.5 µl of a test compound solution and 50 µl of 0.75 nM [$^3$H]-2-MeS-ADP (80 Ci/mmol, mfd. by Amersham Pharmacia Biotech) or 0.75 nM [$^{33}$P]-2-MeS-ADP (2100 Ci/mmol, mfd. by Perkin Elmer), incubated at room temperature for 1 hour in 50 mM Tris-HCl (pH 7.4) containing 100 mM NaCl and 50 mM MgCl$_2$, and then recovered on a glass filter using a cell harvester. A microscintillator was added to the glass filter, and the radioactivity was measured using a liquid scintillation counter. Those to which the solvent alone was added and 1.5 µl of 250 µM ADP was added in the aforementioned test at the same time were regarded as total binding and nonspecific binding, and their radioactivity was measured. By regarding the total binding and nonspecific binding as inhibition ratio 0% and 100% respectively, inhibition ratio (%) of each compound to be tested was calculated. The results at 30 nM (final concentration) of compounds of the present invention are shown in Table 2.

TABLE 2

| Compound to be tested | Inhibition % |
|---|---|
| REx 1 | 76 |
| REx 2 | 86 |
| Ex 2 | 89 |
| Ex 80 | 89 |
| Ex 82 | 65 |
| Ex 87 | 87 |
| Ex 114 | 92 |
| Ex 125 | 83 |
| Ex 146 | 92 |
| Ex 196 | 86 |
| Ex 202 | 82 |
| Ex 261 | 67 |
| Ex 271 | 80 |
| Ex 321 | 73 |
| Ex 324 | 92 |
| Ex 380 | 96 |
| Ex 407 | 72 |
| Ex 488 | 35 |

Test Method (3) Rat Platelet Aggregation Inhibition Test and Measurement of Test Compound Concentration in Plasma By adding sodium hydroxide aqueous solution to the compound of the present invention, 0.5% methyl cellulose aqueous solution or suspension was prepared. The thus prepared liquid was orally administered using a sonde to a male SD rat (5 to 7 weeks of age) of after 12 hours or more of fasting. After 2 hours of the compound administration, blood was collected using a syringe containing 1/10th volume of 3.8% sodium citrate solution. In the same manner as in Test method (1), PPP and PRP of 3×10$^8$ platelets/ml were prepared. A 90 µl portion of the PRP of 3×10$^8$ platelets/ml was incubated at 37° C. for 1 minute, and then 10 µl of ADP (50 µM) was added thereto to induce platelet aggregation, and changes in transmitted light were recorded for 5 minutes. The inhibition ratio was calculated using the area under platelet aggregation curve as an index.

The concentration in plasma was measured using the PPP prepared in the above. In order to prepare a standard curve, a PPP of an SD rat to which the compound was not administered was also separated, and those in which the compound of the present invention was serially diluted with this PPP (from 30 µM to 0.0003 µM in final concentration: optionally selects in response to each compound) were also prepared. A 100 µl portion of the PPP of a rat to which the compound of the present invention was administered and the PPP containing the diluted compound of the present invention was mixed with the same volume of distilled water, and 5% trichloroacetic acid was further added thereto and mixed. After allowing to stand on ice for 10 minutes, a supernatant was recovered by a centrifugation operation. The supernatant was neutralized by adding 3 µl of 2 M Tris base thereto and mixing. A 150 µl portion of the P2Y12 protein expression C6-15 cell membrane fraction (200 µg/ml) was mixed with 50 µl of this trichloroacetic acid-treated PPP (depending on the compound, PPP diluted with 50 mM Tris-HCl (pH 7.4) containing 100 mM NaCl and 50 mM MgCl$_2$ was used). Further, 50 µl of 0.75 nM [$^3$H]-2-MeS-ADP (80 Ci/mmol, mfd. by Amersham Pharmacia Biotech) or 0.75 nM [$^{33}$P]-2-MeS-ADP (2100 Ci/mmol, mfd. by Perkin Elmer) was added thereto and incubated at room temperature for 1 hour in 50 mM Tris-HCl (pH 7.4) containing 100 mM NaCl and 50 mM MgCl$_2$, followed by recovery on a glass filter using a cell harvester. A microscintillator was added to the glass filter, and the radioactivity was measured using a liquid scintillation counter. Using the binding inhibition curve calculated from the measured results derived from PPP containing the serially diluted compound of the present invention as a standard curve, concentration of the compound of the present invention in PPP was converted from the measured results derived from the rat to which the compound of the present invention was administered.

The results are shown in Table 3. As a result of the evaluation by the above-mentioned method, it was revealed that the compound of the present invention shows good platelet aggregation inhibition activity by oral administration and also shows good pharmacokinetics.

TABLE 3

| Compound to be tested | Dose mg/kg | Inhibition % |
|---|---|---|
| REx 1 | 30 | 11 |
| REx 2 | 30 | −7 |
| Ex 82 | 10 | 75 |
| Ex 87 | 10 | 72 |
| Ex 114 | 3 | 66 |
| Ex 125 | 30 | 89 |
| Ex 146 | 30 | 72 |
| Ex 271 | 30 | 89 |
| Ex 297 | 30 | 48 |
| Ex 380 | 30 | 74 |
| Ex 407 | 30 | 54 |

EXAMPLES

The present invention is illustratively described based on examples, but the present invention is not restricted by these examples. In this connection, since novel substances are included in the starting compounds to be used in the Examples, production methods from such starting compounds are described as production examples.

In this connection, symbols in the production examples and Examples represent the following meanings (the same shall apply hereinafter).

Rf: production example number, Ex: Example number, No: compound number, Data: physical data (Sal: salt (No description means free form, and the numeral before the acid component shows compositional ratio. For example, when 2HCl is described, it shows that the compound is dihydrochloride. Oxa: oxalate, TFA: trifluoroacetate)), NMR: δ (ppm) of characteristic peak in $^1$H-NMR, EI: EI-MS (M$^+$ unless otherwise noted), FAB: FAB-MS (Pos) (M$^+$+1 unless otherwise noted), ESI: ESI-MS (Pos) (M$^+$+1 unless otherwise noted), ACPI: ACPI-MS (Pos) (M$^+$+1 unless otherwise noted), ESI(Neg):

ESI-MS (Neg) (M−−1 unless otherwise noted), FAB(Neg): FAB-MS (Neg) (M−−1 unless otherwise noted), Me: methyl, Et: ethyl, nPr, normal propyl, iPr: isopropyl, cPr: cyclopropyl, nBu: normal butyl, iBu: isobutyl, tBu: tert-butyl, cBu: cyclobutyl, cPen: cyclopentyl; cHex: cyclohexyl, Ph: phenyl, Bn: benzyl, Boc: tert-butoxycarbonyl, Ac: acetyl, Bz: benzoyl, TBDMS: tert-butyldimethylsilyl. Syn: production method (The numeral shows that, similar to the Example compound having the number as its Example number, it was produced using the corresponding starting material. When Rf is added before the numeral, it shows that, similar to the production example compound having the number as its production example number, it was produced using the corresponding starting material. When two or more numerals are written, it shows that it was produced by carrying out corresponding production methods starting from the first numeral.), RSyn: production method (The numeral shows that, similar to the production example compound having the number as its production example number, it was produced using the corresponding starting material. When E is added before the numeral, it shows that, similar to the Example compound having the number as its Example number, it was produced using the corresponding starting material.).

Production Example 1

2.6 g of 1,1'-carbonyldiimidazole was added to a 30 ml DMF suspension of 4.0 g 7-(cyclohexylamino)-1-cyclopentyl-6-fluoro-4-oxo-1,4-dihydroquinoline-3-carboxylic acid, followed by stirring at 100° C. for 13.5 hours. 10 ml of 28% aqueous ammonia was added thereto under ice-cooling, followed by stirring under ice-cooling for 75 minutes and at room temperature for 5 hours. After evaporation of the solvent under a reduced pressure, ethanol was added, and heating under reflux was carried out. After cooling to room temperature, the insoluble materials were collected by filtration and dried to obtain 3.7 g of 7-(cyclohexylamino)-1-cyclopentyl-6-fluoro-4-oxo-1,4-dihydroquinoline-3-carboxamide.

Production Example 2

0.87 ml of triethylamine and 0.4 ml of isobutyl chloroformate were added to a 20 ml of dichloromethane solution of 1.0 g of 7-(cyclohexylamino)-1-cyclopentyl-6-fluoro-4-oxo-1,4-dihydroquinoline-3-carboxylic acid at 0° C., followed by stirring at 0° C. for 30 minutes. Then, 315 mg of N,O-dimethylhydroxylamine hydrochloride was added thereto, followed by stirring at room temperature for 1 hour. Chloroform and aqueous saturated ammonium chloride were added to the reaction mixture, the layers were separated, and the organic layer was washed with aqueous saturated so iumchloride. After drying over anhydrous sodium sulfate and subsequent filtration, the solvent was evaporated under a reduced pressure. By purifying the resulting residue by silica gel column chromatography, 950 mg of 7-(cyclohexylamino)-1-cyclopentyl-6-fluoro-N-methoxy-N-methyl-4-oxo-1,4-dihydroquinoline-3-carboxamide was obtained.

Production Example 3

5 g of 2-nitro-1-(2,4,5-trifluorophenyl)ethanone was dissolved in 100 ml of acetic anhydride, and 4.0 ml of triethyl orthoformate was added thereto at room temperature, followed by stirring at 130° C. for 3 hours and concentration under a reduced pressure. The resulting residue was dissolved in 100 ml of dichloromethane, and a 50 ml dichloromethane solution of 2.5 ml of cyclopentylamine was added under ice-cooling, followed by stirring at room temperature for 3 hours. Then, water was added, followed by extraction with chloroform. The organic layer was dried over anhydrous sodium sulfate and then concentrated under a reduced pressure. The resulting residue was dissolved in 80 ml of 1,4-dioxane, and a 20 ml dioxane solution of 3.6 ml 1,8-diazabicyclo[5.4.0]-7-undecene was added at room temperature, followed by stirring at room temperature for 3 hours. By pouring the resulting reaction mixture into ice-cooled water and collecting the insoluble materials by filtration, 1.8 g of 1-cyclopentyl-6,7-difluoro-3-nitroquinoline-4(1H)-one was obtained.

Production Example 4

Under ice-cooling, 11.5 g of sodium triacetoxyborohydride was added in small portions to a solution of 4.0 g of 3,4,5-trifluoroaniline and 3.6 ml cyclopentanone in 150 ml dichloroethane and 3.1 ml acetic acid, and, after rising to room temperature, stirred for 3.5 hours. Aqueous saturated sodium hydrogen carbonate was added thereto, followed by extraction with chloroform and subsequent drying over anhydrous sodium sulfate. After filtration, the solvent was evaporated under a reduced pressure, and the resulting residue was purified by silica gel column chromatography to obtain 5.4 g of N-cyclopentyl-3,4,5-trifluoroaniline.

Production Example 5

3.2 ml of diethyl(ethoxymethylene)malonate was added to 3.3 g of N-cyclopentyl-3,4,5-trifluoroaniline, followed by stirring at 130° C. for 4 hours. By purifying by silica gel column chromatography, 2.2 g of diethyl {[cyclopentyl(3,4,5-trifluorophenyl)amino]methylene}malonate was obtained.

Production Example 6

5.7 g of polyphosphoric acid was added to 2.2 g of diethyl {[cyclopentyl(3,4,5-trifluorophenyl)amino]methylene}malonate, followed by stirring at 140° C. for 40 minutes. The reaction mixture was poured into ice water, and the insoluble materials were collected by filtration. This was dissolved in chloroform, washed with water and aqueous saturated sodium chloride and dried over anhydrous sodium sulfate. After filtration, the solvent was evaporated to obtain 1.4 g of ethyl 1-cyclopentyl-5,6,7-trifluoro-4-oxo-1,4-dihydro quinoline-3-carboxylate.

Production Example 7

42% hydrofluoboric acid was added to 1.1 g of ethyl 1-cyclopentyl-5,6,7-trifluoro-4-oxo-1,4-dihydroquinoline-3-carboxylate, followed by heating at 90° C. for 20 hours. Water was added to the reaction mixture, and the thus formed insoluble materials were collected by filtration and dried to obtain 1.4 g of a boron compound. To 1.4 g of this boron compound were added 15 ml of DMSO and 0.97 ml of cyclohexylamine, followed by stirring at room temperature for 30 minutes. Water was added to the reaction mixture, and the insoluble materials were collected by filtration. After drying, 30 ml of ethanol and 15 ml of aqueous 1 M sodium hydroxide solution were added thereto, followed by stirring at 80° C. for 1.5 hours. After completion of the reaction, the insoluble materials were removed by filtration, water and diethyl ether were added to the filtrate to carry out separation of layers, and 1 M hydrochloric acid was added to the aqueous layer. The precipitate formed was collected by filtration and dried to obtain 1.0 g of 7-(cyclohexylamino)-1-cyclopentyl-5,6-difluoro-4-oxo-1,4-dihydroquinoline-3-carboxylic acid.

Production Example 8

Under ice-cooling, 3.2 ml of n-butyl lithium (1.60 M hexane solution) was added to a 2.4 ml THF solution of 0.58 ml benzyl alcohol, followed by stirring for 1 hour. The solvent was evaporated under a reduced pressure, followed by the addition of 8.0 ml of toluene for suspension. The suspension prepared was added to a toluene suspension of 400 mg of 7-(cyclohexylamino)-1-cyclopentyl-5,6-difluoro-4-oxo-1,4-dihydroquinoline-3-carboxylic acid, which was prepared in a separate container, followed by stirring at room temperature for 6 hours. Then, 1 M hydrochloric acid was added to the reaction mixture, followed by extraction with chloroform and washing with aqueous saturated sodium chloride. After drying over anhydrous sodium sulfate and subsequent filtration, the solvent was evaporated under a reduced pressure. By recrystallizing the resulting residue using ethyl acetate, 400 mg of 5-(benzyloxy)-7-(cyclohexylamino)-1-cyclopentyl-6-fluoro-4-oxo-1,4-dihydroquinoline-3-carboxylic acid was obtained.

Production Example 9

900 mg of ethyl 1-cyclopentyl-7-fluoro-4-oxo-1,4-dihydroquinoline-3-carboxylate was dissolved in 6.4 ml of acetic acid, and 0.8 ml of 6 M hydrochloric acid was added, followed by overnight stirring at 120° C. The resulting reaction mixture was cooled to room temperature, and the insoluble materials were collected by filtration and washed with water to obtain 710 mg of 1-cyclopentyl-7-fluoro-4-oxo-1,4-dihydroquinoline-3-carboxylic acid.

Production Example 10

1.02 g of 1-cyclobutylethylamine hydrochloride and 1.05 ml of triethylamine were added under ice-cooling to a 15 ml THF solution of 2.0 g of ethyl 2-(2-chloro-4,5-difluorobenzoyl)-3-ethoxyacrylate, followed by overnight stirring at room temperature. Water was added to the resulting reaction mixture, followed by extraction with ether and washing with water and aqueous saturated sodium chloride. After drying over anhydrous magnesium sulfate, concentration under a reduced pressure was carried out. 315 mg of 55% sodium hydride was added under ice-cooling to a 30 ml dioxane solution of the resulting residue, followed by overnight stirring at 80° C. The reaction mixture was poured into 1 M hydrochloric acid, followed by extraction with chloroform and washing with water and aqueous saturated sodium chloride. After drying over anhydrous sodium sulfate and subsequent concentration under a reduced pressure, the resulting residue was purified by silica gel column chromatography to obtain 1.13 g of ethyl 1-(1-cyclobutylethyl)-6,7-difluoro-4-oxo-1,4-dihydroquinoline-3-carboxylate.

In the same manner as in the Production Examples 1 to 10, Production Example compounds 11 to 27 shown in Tables 4 to 9 were produced using corresponding starting materials, respectively. Structures and physicochemical date of Production Example compounds are shown in Tables 4 to 9.

Example 1

250 mg of 3-amino-7-(cyclohexylamino)-1-cyclopentyl-6-fluoroquinoline-4(1H)-one and 127 mg of 4-ethoxy-4-oxobutanoic acid were dissolved in 20 ml of DMF, and 170 mg of N-[3-(dimethylamino)propyl]-N'-ethylcarbodiimide hydrochloride and 160 mg of 1-hydroxybenzotriazole were added, followed by overnight stirring at room temperature. By adding water to the reaction mixture and collecting the insoluble materials by filtration, 220 mg of ethyl 4-{[7-(cyclohexylamino)-1-cyclopentyl-6-fluoro-4-oxo-1,4-dihydroquinolin-3-yl]amino}-4-oxobutanoate was obtained.

Example 2

200 mg of ethyl 4-{[7-(cyclohexylamino)-1-cyclopentyl-6-fluoro-4-oxo-1,4-dihydroquinolin-3-yl]amino}-4-oxobutanoate was dissolved in 2.0 ml of THF and 2.0 ml of ethanol, and 1.3 ml of aqueous 1M sodium hydroxide solution was added, followed by stirring at room temperature for 4 hours. After adding 1 M hydrochloric acid and water thereto, the insoluble materials were collected by filtration to obtain 180 mg of 4-{[7-(cyclohexylamino)-1-cyclopentyl-6-fluoro-4-oxo-1,4-dihydroquinolin-3-yl]amino}-4-oxobutanoic acid.

Example 3

200 mg of diethyl {(E)-2-[7-(cyclohexylamino)-1-(1-ethylpropyl)-6-fluoro-4-oxo-1,4-dihydroquinolin-3-yl]vinyl}phosphonate was dissolved in 2.0 ml of chloroform, and 0.4 ml of bromotrimethylsilane was added, followed by overnight stirring at room temperature. Ethanol was added to the reaction mixture, followed by concentration under a reduced pressure. Ethyl acetate was added to the resulting residue, and the insoluble materials were collected by filtration to obtain 120 mg of {(E)-2-[7-(cyclohexylamino)-1-(1-ethylpropyl)-6-fluoro-4-oxo-1,4-dihydroquinolin-3-yl]vinyl}phosphonic acid hydrobromide.

Example 4

169 mg of sodium triacetoxyborohydride was added to a mixed solution 10 ml of 1,2-dichloroethane and 0.05 ml of acetic acid of 142 mg 7-(cyclohexylamino)-1-cyclopentyl-6-fluoro-4-oxo-1,4-dihydroquinoline-3-carbaldehyde and 66 mg of 4-aminophenol, followed by stirring for 24 hours. Aqueous saturated sodium hydrogen carbonate was added thereto, followed by extraction with chloroform. After drying over anhydrous sodium sulfate and subsequent filtration, concentration under a reduced pressure was carried out. The resulting residue was purified by silica gel column chromatography and then crystallized from ethyl acetate to obtain 46 mg of [7-(cyclohexylamino)-1-cyclopentyl-6-fluoro-3-{[(4-hydroxyphenyl)amino]methyl}quinolin-4(1H)-one.

Example 5

250 mg of 3-(aminomethyl)-7-(cyclohexylamino)-1-(1-ethylpropyl)-6-fluoroquinolin-4(1H)-one hydrochloride was dissolved in 25 ml of THF, and 0.11 ml of diethyl (2-oxopropyl)phosphonate and 123 mg of sodium triacetoxyborohydride, 0.16 ml of triethylamine and 1.25 ml of acetic acid were added in that order, followed by overnight stirring at room temperature. Water was added, and the insoluble materials were collected by filtration and then purified by silica gel column chromatography to obtain 135 mg of diethyl[2-({[7-(cyclohexylamino)-1-(1-ethylpropyl)-6-fluoro-4-oxo-1,4-dihydroquinolin-3-yl]methyl}amino)propyl]phosphonate.

Example 6

170 mg of ethyl 4-({[7-(cyclohexylamino)-1-(1-ethylpropyl)-6-fluoro-4-oxo-1,4-dihydroquinolin-3-yl]

methyl}amino)butanoate was dissolved in 2.0 ml of pyridine, and 0.040 ml of acetic anhydride was added, followed by overnight stirring at room temperature. After concentrating the reaction mixture under a reduced pressure, water was added to the resulting residue, followed by extraction with chloroform. The organic layer was dried over anhydrous sodium sulfate and then filtered and concentrated under a reduced pressure. By purifying the resulting residue by silica gel column chromatography, 165 mg of ethyl 4-(acetyl{[7-(cyclohexylamino)-1-(1-ethylpropyl)-6-fluoro-4-oxo-1,4-dihydroquinolin-3-yl]methyl}amino)butanoate was obtained.

Example 7

180 mg of 4-nitrophenyl chloroformate was dissolved in 3.0 ml of dichloromethane, and 140 mg of ethyl 3-aminopropanoate hydrochloride and 0.15 ml of pyridine were added, followed by overnight stirring at room temperature. Water was added to the reaction mixture, followed by extraction with chloroform. The organic layer was washed with aqueous saturated sodium chloride, dried over anhydrous sodium sulfate, filtered and then concentrated under a reduced pressure. By purifying the resulting residue by silica gel column chromatography, 180 mg of ethyl 3-{[(4-nitrophenoxy)carbonyl]amino}propanoate was obtained. 180 mg of ethyl 3-{[(4-nitrophenoxy)carbonyl]amino}propanoate was dissolved in 2.0 ml of dichloromethane, and 220 mg of 3-amino-7-(cyclohexylamino)-1-(1-ethylpropyl)-6-fluoroquinolin-4(1H)-one and 0.15 ml of pyridine were added, followed by overnight stirring at room temperature. Water was added, followed by extraction with chloroform. The organic layer was washed with aqueous saturated sodium chloride, dried over anhydrous sodium sulfate and then filtered and concentrated under a reduced pressure. By purifying the resulting residue by silica gel column chromatography, 120 mg of ethyl 3-[({[7-(cyclohexylamino)-1-(1-ethylpropyl)-6-fluoro-4-oxo-1,4-dihydroquinolin-3-yl]amino}carbonyl)amino]propanoate was obtained.

Example 8

287 mg of ethyl[(5-chloro-2-thienyl)sulfonyl]carbamate was dissolved in 5.0 ml of toluene, and 250 mg of 3-amino-7-(cyclohexylamino)-6-fluoro-1-isopropylquinolin-4(1H)-one was added, followed by overnight stirring at 110° C. The reaction mixture was cooled to room temperature and concentrated under a reduced pressure. Then, ethyl acetate was added and the insoluble materials were collected by filtration, thereby obtaining 280 mg of 5-chloro-N-({[7-(cyclohexylamino)-6-fluoro-1-isopropyl-4-oxo-1,4-dihydroquinolin-3-yl]amino}carbonyl)thiophene-2-sulfonamide.

Example 9

224 mg of 2-amino-N-[7-(cyclohexylamino)-1-(1-ethylpropyl)-6-fluoro-4-oxo-1,4-dihydroquinolin-3-yl]acetamide hydrochloride was dissolved in 5.0 ml of DMF, and 228 mg of potassium carbonate and 0.18 ml of ethyl bromoacetate were added, followed by overnight stirring at 60° C. The reaction mixture was cooled to room temperature, water was added, and the insoluble materials were collected by filtration to obtain 35 mg of diethyl 2,2'-[(2-{[7-(cyclohexylamino)-1-(1-ethylpropyl)-6-fluoro-4-oxo-1,4-dihydroquinolin-3-yl]amino}-2-oxoethyl)imino]diacetate.

Example 10

150 mg of ethyl {[7-(cyclohexylamino)-1-(1-ethylpropyl)-6-fluoro-4-oxo-1,4-dihydroquinolin-3-yl]amino}acetate was dissolved in 3.0 ml of THF, and 0.060 ml of triethylamine and 0.060 ml of ethyl 5-chloro-5-oxopentanoate were added, followed by overnight stirring at room temperature. Water was added to the reaction mixture, followed by extraction with chloroform. The resulting organic layer was washed with aqueous saturated sodium chloride, dried over anhydrous sodium sulfate and then concentrated under a reduced pressure. By purifying the resulting residue by silica gel column chromatography, 199 mg of ethyl 5-[[7-(cyclohexylamino)-1-(1-ethylpropyl)-6-fluoro-4-oxo-1,4-dihydroquinolin-3-yl](2-ethoxy-2-oxoethyl)amino]-5-oxopentanoate was obtained.

Example 11

200 mg of ethyl (2E)-3-[7-(cyclohexylamino)-1-cyclopentyl-6-fluoro-4-oxo-1,4-dihydroquinolin-3-yl]acrylate was dissolved in 4.0 ml of ethanol, and 50 mg of palladium-carbon was added, followed by overnight stirring at room temperature in an atmosphere of hydrogen. The reaction mixture was filtered using celite and concentrated under a reduced pressure to obtain 200 mg of ethyl (3-[7-(cyclohexylamino)-1-cyclopentyl-6-fluoro-4-oxo-1,4-dihydroquinolin-3-yl]propanoate.

Example 12

213 µl of diisopropyl azodicarboxylate was added to a 5.0 ml dichloromethane solution of 263 mg of benzyl (2R)-2-hydroxy-3-phenylpropanoate and 270 mg of triphenylphosphine at 0° C., followed by stirring for 15 minutes. Then, 177 mg of 7-(cyclohexylamino)-1-cyclopentyl-6-fluoro-3-(hydroxymethyl)quinolin-4(1H)-one was added thereto, followed by stirring at room temperature for 4 hours. Water was added to the reaction mixture, followed by extraction with EtOAc and washing with aqueous saturated sodium chloride. After drying over anhydrous sodium sulfate and subsequent evaporation under a reduced pressure, the residue was purified by silica gel column chromatography to obtain 160 mg of benzyl (2S)-2-{[7-(cyclohexylamino)-1-cyclopentyl-6-fluoro-4-oxo-1,4-dihydroquinolin-3-yl]oxy}-3-phenylpropanoate.

Example 13

690 mg of potassium carbonate and 363 mg of 4-fluorobenzonitrile were added to a 10 ml DMF solution of 344 mg of 7-(cyclohexylamino)-1-cyclopentyl-6-fluoro-3-hydroxyquinolin-4(1H)-one, followed by overnight stirring at 80° C. After completion of the reaction and subsequent cooling to room temperature, aqueous saturated ammonium chloride was added to the reaction mixture, followed by extraction with ethyl acetate. After drying over anhydrous sodium sulfate and subsequent evaporation under a reduced pressure, the residue was purified by silica gel column chromatography to obtain 100 mg of 4-{[7-(cyclohexylamino)-1-cyclopentyl-6-fluoro-4-oxo-1,4-dihydroquinolin-3-yl]oxy}benzonitrile.

Example 14

5.0 ml of ethanol and 1.5 ml of aqueous 6 M sodium hydroxide solution were added to 93 mg of 4-{[7-(cyclohexylamino)-1-cyclopentyl-6-fluoro-4-oxo-1,4-dihydroquinolin-3-yl]oxy}benzonitrile, followed by heating under reflux for 2 days. After cooling, the reaction system was neutralized with 1 M hydrochloric acid. Water was added and the solid precipitated was collected by filtration. By crystallizing the resulting solid from ethyl acetate-hexane, 65 mg of 4-{[7-(cyclohexylamino)-1-cyclopentyl-6-fluoro-4-oxo-1,4-dihydroquinolin-3-yl]oxy}benzoic acid was obtained.

Example 15

840 mg of 7-(cyclohexylamino)-1-cyclopentyl-6-fluoro-4-oxo-1,4-dihydroquinoline-3-carbaldehyde was dissolved in 40 ml of chloroform, and 0.47 ml of trimethylsilyl cyanide and 0.05 ml of triethylamine was added under ice-cooling, followed by stirring at room temperature for 5.5 hours. After stirring at room temperature for 1.5 hours after further adding 0.06 ml of trimethylsilyl cyanide, 0.06 ml of trimethylsilyl cyanide was further added thereto, followed by stirring at room temperature for 2 days. The resulting precipitate was filtered and washed with chloroform to obtain a solid. The resulting solid was dissolved in 13 ml of concentrated hydrochloric acid, followed by stirring at 100° C. for 2.5 hours. After cooling to room temperature, water was added, followed by extraction with chloroform, drying over anhydrous sodium sulfate and then concentration under a reduced pressure. The resulting residue was purified by silica gel column chromatography to obtain crude product of [7-(cyclohexylamino)-1-cyclopentyl-6-fluoro-4-oxo-1,4-dihydroquinolin-3-yl](hydroxy)acetic acid. The resulting crude product was washed with water:methanol (1:2) and ethyl acetate. Ethyl acetate and aqueous saturated sodium hydrogen carbonate were added to the resulting solid to carry out layer separation operation. 1 M hydrochloric acid was added to the aqueous layer, followed by extraction with ethyl acetate and concentration under a reduced pressure. A mixed solvent of THF and water was added to the resulting residue and the insoluble materials were collected by filtration to obtain 149 mg of [7-(cyclohexylamino)-1-cyclopentyl-6-fluoro-4-oxo-1,4-dihydroquinolin-3-yl](hydroxy)acetic acid.

Example 16

52 mg of [7-(cyclohexylamino)-1-cyclopentyl-6-fluoro-4-oxo-1,4-dihydroquinolin-3-yl](hydroxy)acetic acid was dissolved in 10 ml of methanol, and 0.4 ml of concentrated sulfuric acid was added, followed by stirring at room temperature for 1 hour. Aqueous saturated sodium hydrogen carbonate was added to the reaction mixture, followed by extraction with ethyl acetate, washing with aqueous saturated sodium chloride and concentration under a reduced pressure. The resulting residue was recrystallized from aqueous methanol to obtain 53 mg of methyl[7-(cyclohexylamino)-1-cyclopentyl-6-fluoro-4-oxo-1,4-dihydroquinolin-3-yl](hydroxy)acetate.

Example 17

146 mg of methyl[7-(cyclohexylamino)-1-cyclopentyl-6-fluoro-4-oxo-1,4-dihydroquinolin-3-yl](hydroxy)acetate was dissolved in 10 ml of THF, and 46 mg of 60% sodium hydride was added under ice-cooling, followed by stirring at room temperature for 30 minutes. Then, 58 μl of ethyl bromoacetate was added to the reaction mixture, followed by stirring at room temperature for 5 hours. 46 mg of 60% sodium hydride and 10 ml of THF were further added under ice-cooling, followed by stirring at room temperature for 2 hours. Then, 58 μl of ethyl bromoacetate was added thereto, followed by stirring at room temperature for 17 hours. Aqueous saturated sodium hydrogen carbonate was added to the reaction mixture, followed by extraction with ethyl acetate. Then, the organic layer was washed with aqueous saturated sodium chloride. After drying over anhydrous sodium sulfate, concentration was carried out under a reduced pressure. The resulting residue was purified by silica gel column chromatography to obtain 66 mg of methyl[7-(cyclohexylamino)-1-cyclopentyl-6-fluoro-4-oxo-1,4-dihydroquinolin-3-yl](2-ethoxy-2-oxoethoxy)acetate.

Example 18

13 g of diethyl {(E)-2-[7-(cyclohexylamino)-1-(1-ethylpropyl)-6-fluoro-4-oxo-1,4-dihydroquinolin-3-yl]vinyl}phosphonate was dissolved in 150 ml of chloroform, and 27.2 ml of bromotrimethylsilane was added, followed by overnight stirring at room temperature. Ethanol was added to the reaction mixture, followed by concentration under a reduced pressure. Aqueous 1 M sodium hydroxide solution and ether were added to the resulting residue to carry out layer separation operation. Concentrated hydrochloric acid was added to the aqueous layer, followed by stirring at room temperature for 2 hours. Then, the insoluble materials were collected by filtration and washed with water to obtain 10.32 g of {(E)-2-[7-(cyclohexylamino)-1-(1-ethylpropyl)-6-fluoro-4-oxo-1,4-dihydroquinolin-3-yl]vinyl}phosphonic acid.

Example 19

428 mg of (methoxymethyl)triphenylphosphonium chloride was dissolved in 5 ml of THF, and 1.2 ml of 1.6 M n-butyl lithium hexane solution was added under ice-cooling in an atmosphere of argon, followed by stirring at the same temperature for 30 minute. A 5 ml THF solution of 178 mg of 7-(cyclohexylamino)-1-cyclopentyl-6-fluoro-4-oxo-1,4-dihydroquinoline-3-carbaldehyde was added under ice-cooling thereto, followed by stirring at the same temperature for 15 minutes and then stirring at room temperature for 3 hours. The reaction mixture was poured into ice water, followed by extraction with ethyl acetate, drying over anhydrous sodium sulfate and then concentration under a reduced pressure. The resulting residue was dissolved in 10 ml of dioxane, and 5 ml of a 4 M hydrogen chloride dioxane solution was added, followed by stirring at room temperature for 2 hours. The reaction mixture was poured into an ice-cooled aqueous saturated sodium hydrogen carbonate, followed by extraction with ethyl acetate, drying over anhydrous sodium sulfate and then concentration under a reduced pressure. By purifying the resulting residue by silica gel column chromatography, 239 mg of crude product of [7-(cyclohexylamino)-1-cyclopentyl-6-fluoro-4-oxo-1,4-dihydroquinolin-3-yl)acetaldehyde was obtained. The resulting crude product was dissolved in 10 ml of ethanol, and 75 mg of sodium borohydride was added, followed by stirring at room temperature for 1 hour. Water was added to the reaction mixture, followed by extraction with ethyl acetate, drying over anhydrous sodium sulfate and then concentration under a reduced pressure. The resulting residue was purified by silica gel column chromatography and crystallized from ethyl acetate to obtain 18 mg of 7-(cyclohexylamino)-1-cyclopentyl-6-fluoro-3-(2-hydroxyethyl)quinolin-4(1H)-one.

Example 20

856 mg of (methoxymethyl)triphenylphosphonium chloride was dissolved in 10 ml of THF, and 1.8 ml of a 1.6 M n-butyl lithium hexane solution was added under ice-cooling in an atmosphere of argon, followed by stirring at the same temperature for 30 minute. A 10 ml THF solution of 356 mg of 7-(cyclohexylamino)-1-cyclopentyl-6-fluoro-4-oxo-1,4-dihydroquinoline-3-carbaldehyde was added under ice-cooling thereto, followed by stirring at room temperature for 3 hours. The reaction mixture was poured into ice water, followed by extraction with ethyl acetate, drying over anhydrous sodium sulfate and then concentration under a reduced pressure. The resulting residue was purified by column chromatography to obtain 552 mg crude product of 7-(cyclohexylamino)-1-cyclopentyl-6-fluoro-3-[2-methoxyvinyl] quinolin-4(1H)-one. 159 mg of the resulting crude product was dissolved in 14 ml of dioxane, and 7 ml of a 4 M hydrogen chloride dioxane solution was added, followed by stirring at room temperature for 0.5 hour. The reaction mixture was concentrated under a reduced pressure, and the resulting residue was dissolved in 6 ml of 2-methyl-2-propanol, 1 ml of acetonitrile and 2 ml of water. Then, 0.26 ml of 2-methyl-2-butene, 78 mg of sodium dihydrogenphosphate dihydrate and 228 mg of a 79% sodium chlorite aqueous solution were added under ice-cooling, followed by stirring at room temperature for 14 hours. Water was added to the reaction mixture, followed by extraction with chloroform, drying over anhydrous sodium sulfate and then concentration under a reduced pressure. The resulting residue was purified by silica gel column chromatography and crystallized from ethyl acetate to obtain 5 mg of 7-(cyclohexylamino)-1-cyclopentyl-6-fluoro-4-oxo-1,4-dihydroquinolin-3-yl]acetic acid.

Example 21

199 mg of 7-(cyclohexylamino)-1-(1-ethylpropyl)-6-fluoro-3-(4-hydroxybutyl)quinolin-4(1H)-one was dissolved in 11 ml of 1,2-dichloroethane, and 257 mg of triphenylphosphine and 405 mg of carbon tetrabromide were added at room temperature, followed by stirring for 15 minutes. Aqueous saturated sodium hydrogen carbonate was added to the reaction mixture, followed by extraction with chloroform, washing with aqueous saturated sodium chloride, drying over anhydrous sodium sulfate and then concentration under a reduced pressure. The resulting residue was purified by a chromatography to obtain 78 mg of 3-(4-bromobutyl)-7-(cyclohexylamino)-1-(1-ethylpropyl)-6-fluoro quinolin-4(1H)-one.

Example 22

To 557 mg of 3-(4-bromobutyl)-7-(cyclohexylamino)-1-(1-ethylpropyl)-6-fluoroquinolin-4(1H)-one was added 5 ml of triethylphosphite, followed by stirring at 160° C. for 4 hours. The reaction mixture was concentrated under a reduced pressure, and the resulting residue was purified by a column chromatography to obtain 240 mg of diethyl {4-[7-(cyclohexylamino)-1-(1-ethylpropyl)-6-fluoro-4-oxo-1,4-dihydroquinolin-3-yl]butyl}phosphonate.

Example 23

To 2 ml of a 2 M isopropyl magnesium chloride THF solution was added 2 ml of THF and, at −78° C., 0.71 ml of diethyl[bromo(difluoro)methyl]phosphonate, followed by stirring at the same temperature for 5 minutes. A 10 ml THF solution of 358 mg of 7-(cyclohexylamino)-1-(1-ethylpropyl)-6-fluoro-4-oxo-1,4-dihydroquinoline-3-carbaldehyde was added dropwise to the reaction mixture and, after gradual temperature rising to room temperature, this was stirred for 2.5 hours. Aqueous saturated sodium chloride was added to the reaction mixture, followed by extraction with chloroform and ethyl acetate. The organic layer was dried over anhydrous magnesium sulfate and then concentrated under a reduced pressure. Methanol was added to the residue, insoluble materials were filtered, and the resulting filtrate was evaporated under a reduced pressure. By purifying the resulting residue by a column chromatography, 257 mg of diethyl {2-[7-(cyclohexylamino)-1-(1-ethylpropyl)-6-fluoro-4-oxo-1,4-dihydro quinolin-3-yl]-1,1-difluoro-2-hydroxyethyl}phosphonate.

Example 24

1.0 g of 7-(cyclohexylamino)-1-cyclopentyl-6-fluoro-4-oxo-1,4-dihydroquinoline-3-carbaldehyde was dissolved in 20 ml of DMF, and 2.0 g of potassium carbonate and 2.8 ml of ethyl(diethoxyphosphoryl)acetate were added, followed by overnight stirring at 60° C. The resulting reaction mixture was cooled to room temperature, water was added, and then the insoluble materials were collected by filtration to obtain 1.2 g of ethyl (2E)-3-[7-(cyclohexylamino)-1-cyclopentyl-6-fluoro-4-oxo-1,4-dihydroquinolin-3-yl]acrylate.

Example 25 and Example 26

500 mg of {(E)-2-[7-(cyclohexylamino)-1-(1-ethylpropyl)-6-fluoro-4-oxo-1,4-dihydroquinolin-3-yl] vinyl}phosphonic acid was dissolved in 10 ml of acetonitrile, and 86 mg of sodium iodide, 0.51 ml of 1,8-diazabicyclo [5.4.0]-7-undecene, 194 mg of tetrabutylammonium hydrogensulfate and 0.53 ml of chloromethyl pivalate were added in that order, followed by overnight stirring at 80° C. Aqueous saturated ammonium chloride was added to the reaction mixture, followed by extraction with chloroform. The organic layer was washed with aqueous saturated sodium chloride, dried over anhydrous sodium sulfate and then evaporated under a reduced pressure. By purifying the resulting residue by silica gel column chromatography, 400 mg of bis{[(2,2-dimethylpropanoyl)oxy]methyl}{(E)-2-[7-(cyclohexylamino)-1-(1-ethylpropyl)-6-fluoro-4-oxo-1,4-dihydroquinolin-3-yl]vinyl}phosphonate (Example 25) and 190 mg of {[{(E)-2-[7-(cyclohexylamino)-1-(1-ethylpropyl)-6-fluoro-4-oxo-1,4-dihydro-3-quinolinyl]vinyl}(hydroxy) phosphoryl]oxy}methyl pivalate (Example 26) were obtained.

Example 27

To a 5.0 ml DMF solution of 144 mg of 7-(cyclohexylamino)-6-fluoro-3-hydroxy-1-isopropylquinolin-4(1H)-one were added 313 mg of potassium carbonate and 100 μl of ethyl bromoacetate in that order, followed by overnight stirring at room temperature. Aqueous saturated ammonium chloride was added to the reaction mixture, followed by extraction with ethyl acetate. After drying over anhydrous sodium sulfate and subsequent evaporation under a reduced pressure, the residue was purified by silica gel column chromatography to obtain 159 mg of ethyl {[7-(cyclohexylamino)-6-fluoro-1-isopropyl-4-oxo-1,4-dihydroquinolin-3-yl]oxy}acetate.

Example 28

To a 2.9 ml dioxane solution of tert-butyl (2-{[7-(cyclohexylamino)-1-(1-ethylpropyl)-6-fluoro-4-oxo-1,4-dihydroquinolin-3-yl]amino}-2-oxoethyl)carbamate was added 3.0 ml of a 4M hydrogen chloride dioxane solution, followed by overnight stirring at room temperature. The insoluble materials were collected by filtration to obtain 550 mg of 2-amino- N-[7-(cyclohexylamino)-1-(1-ethylpropyl)-6-fluoro-4-oxo-1,4-dihydroquinolin-3-yl]acetamide hydrochloride.

Example 29

To a 90 ml DMF solution of 15.0 g of 7-(cyclohexylamino)-1-cyclopentyl-6-fluoro-4-oxo-1,4-dihydroquinoline-3-carboxylic acid was added 9.9 g of 1,1'-carbonyldiimidazole, followed by stirring at 80° C. for 24 hours. After cooling, the reaction mixture was poured into ice water, and the solid precipitated was collected by filtration. Next, 1.9 g of sodium borohydride was added at 0° C. to a mixed solution of 200 ml THF and 100 ml water of the resulting solid, followed by stirring at the same temperature for 2 hours. Water was added, the solvent was evaporated under a reduced pressure, and the insoluble materials were collected by filtration to obtain 13.8 g of 7-(cyclohexylamino)-1-cyclopentyl-6-fluoro-3-(hydroxymethyl)quinolin-4(1H)-one.

Example 30

After adding 0.32 ml of DMSO to a 7.0 ml dichloromethane solution of 0.20 ml of oxalyl dichloride at −78° C. and stirring for 30 minutes, a dichloromethane solution of 330 mg of N-[7-(cyclohexylamino)-1-(1-ethylpropyl)-6-fluoro-4-oxo-1,4-dihydroquinolin-3-yl]-2-(hydroxymethyl)butanamide was added at −78° C., followed by stirring for 30 minutes. Next, 1.2 ml of triethylamine was added thereto, and the temperature was risen from −78° C. to room temperature spending 2 hours. Aqueous saturated sodium chloride was added to the reaction mixture, followed by extraction with ethyl acetate, drying over anhydrous sodium sulfate, and evaporation under a reduced pressure, thereby obtaining 320 mg of crude product of N-[7-(cyclohexylamino)-1-(1-ethylpropyl)-6-fluoro-4-oxo-1,4-dihydroquinolin-3-yl]-2-formylbutanamide. To a 6.4 ml dichloromethane solution of 320 mg of the resulting crude product was added 290 mg of methyl(triphenylphosphoranilidene)acetate, followed by overnight stirring at room temperature. By evaporating the reaction mixture under a reduced pressure and purifying the resulting mixture by silica gel column chromatography, 220 mg of methyl (2E)-4-({[7-(cyclohexylamino)-1-(1-ethylpropyl)-6-fluoro-4-oxo-1,4-dihydroquinolin-3-yl]amino}carbonyl)hex-2-enoate was obtained.

Example 31

To a 8 ml THF solution of 400 mg of ethyl 3-[7-(cyclohexylamino)-1-cyclopentyl-6-fluoro-4-oxo-1,4-dihydroquinolin-3-yl]propanoate was added 40 mg of lithium aluminum hydride at 0° C., followed by stirring for 2 hours. Water was added to the reaction mixture, followed by and filteraion through celite. After evaporation under a reduced pressure, the resulting residue was purified by silica gel column chromatography to obtain 288 mg of 7-(cyclohexylamino)-1-cyclopentyl-6-fluoro-3-(3-hydroxypropyl)quinolin-4(1H)-one.

Example 32

To a 5 ml 1,4-dioxane solution of 300 mg of {[7-(cyclohexylamino)-1-cyclopentyl-6-fluoro-4-oxo-1,4-dihydroquinolin-3-yl]oxy}acetonitrile was added 0.8 ml of tributyltin azide, followed by heating under reflux for 2 days. After cooling to room temperature, aqueous 1M sodium hydroxide solution and ether were added, followed by layer separation operation. To the aqueous layer was added 1 M hydrochloric acid, followed by extraction with chloroform and washing with aqueous saturated sodium chloride. After drying over anhydrous sodium sulfate, the solvent was evaporated under a reduced pressure. By adding ether to the resulting residue and collecting the insoluble materials by filtration, 70 mg of 7-(cyclohexylamino)-1-cyclopentyl-6-fluoro-3-(1H-tetrazol-5-ylmethoxy)quinolin-4(1H)-one was obtained.

Example 33

To a 30 ml dichloromethane suspension of 3.69 g of 7-(cyclohexylamino)-1-cyclopentyl-6-fluoro-4-oxo-1,4-dihydroquinoline-3-carboxamide were added at −78° C. 7.0 ml of triethylamine and a 10 ml dichloromethane solution of 4.0 ml of trifluoroacetic anhydride. After gradually rising the temperature, it was stirred at room temperature for 2 days. After adding water, it was extracted with chloroform, followed by drying over anhydrous sodium sulfate. After filtration, the solvent was evaporated under a reduced pressure and the resulting residue was purified by silica gel column chromatography. After adding a mixed solvent of 30 ml of THF, 30 ml of methanol and 10 ml of water to the resulting solid, 2.3 g of potassium carbonate was added thereto under ice-cooling. After stirring at room temperature for 15 hours, 1.0 g of potassium carbonate was added thereto, followed by stirring at room temperature for 4 days. After evaporating the solvent under a reduced pressure, water was added, followed by extraction with chloroform. After drying over anhydrous sodium sulfate and subsequent filtration, the solvent was evaporated under a reduced pressure. By washing the resulting residue with ethyl acetate, 2.62 g of 7-(cyclohexylamino)-1-cyclopentyl-6-fluoro-4-oxo-1,4-dihydroquinoline-3-carbonitrile was obtained.

Example 34

10 ml of Raney nickel was washed three times with ethanol. 30 ml of ethanol, 3 ml of aqueous ammonia and 2.5 g of 7-(cyclohexylamino)-1-cyclopentyl-6-fluoro-4-oxo-1,4-dihydroquinoline-3-carbonitrile were added thereto, followed by overnight stirring in an atmosphere of hydrogen. After addition of chloroform and subsequent filtration using celite, the solvent was evaporated under a reduced pressure. The resulting residue was dissolved in 20 ml of THF, a 10 ml THF solution of 1.8 g of di-tert-butyl dicarbonate was added under ice-cooling, followed by overnight stirring at room temperature. A 10 ml THF solution of 1.0 g of di-tert-butyl dicarbonate was added thereto under ice-cooling, followed by stirring at room temperature for 3 days. A 10 ml THF solution of 1.0 g of di-tert-butyl dicarbonate was added thereto under ice-cooling, followed by overnight stirring at room temperature. After evaporation of the solvent under a reduced pressure and subsequent purification by silica gel column chromatography, the resulting solid was recrystallized from hexane-ethyl acetate to obtain 1.22 g of tert-butyl {[7-(cyclohexylamino)-1-cyclopentyl-6-fluoro-4-oxo-1,4-dihydroquinolin-3-yl]methyl}carbamate.

Example 35

To 5.50 g of 7-(cyclohexylamino)-1-(1-ethylpropyl)-6-fluoro-4-oxo-1,4-dihydroquinoline-3-carbonitrile were added 50 ml of ethanol, 3.0 ml of concentrated hydrochloric acid and 0.60 g of platinum oxide, followed by overnight stirring in an atmosphere of hydrogen. After adding water, celite filtration was carried out and the solvent was evaporated under a reduced pressure. The resulting residue was dissolved by adding 30 ml of water and 20 ml of THF, and 4.0 g of sodium hydrogen carbonate and 4.5 g of di-tert-butyl dicarbonate were added under ice-cooling, followed by stirring under ice-cooling for 1 hour and overnight at room temperature. After evaporation of the solvent under a reduced pressure, water was added, followed by extraction with chloroform and drying over anhydrous sodium sulfate. After filtration, the solvent was evaporated under a reduced pressure and the resulting residue was purified by silica gel column chromatography to obtain 5.72 g of tert-butyl {[7-(cyclohexylamino)-1-(1-ethylpropyl)-6-fluoro-4-oxo-1,4-dihydroquinolin-3-yl]methyl}carbamate.

Example 36

To 0.31 g of 7-(cyclohexylamino)-6-fluoro-4-oxo-1-pyrrolidin-3-yl-1,4-dihydroquinoline-3-carbonitrile hydrochloride were added 5 ml of ethanol, 0.2 ml of concentrated hydrochloric acid and 0.10 g of platinum oxide, followed by overnight stirring in an atmosphere of hydrogen. After adding water, celite filtration was carried out and the solvent was evaporated under a reduced pressure. By purifying the resulting residue by an ODS column chromatography, 256 mg of 3-(aminomethyl)-7-(cyclohexylamino)-6-fluoro-1-pyrrolidin-3-ylquinolin-4(1H)-one hydrochloride was obtained.

Example 37

To a 40 ml DMSO solution of 2.0 g of 1-cyclopentyl-6,7-difluoro-3-nitroquinolin-4(1H)-one was added 2.3 ml of cyclohexylamine, followed by overnight stirring at 90° C. The reaction mixture was cooled to room temperature and poured into ice-cooled water, and then the insoluble materials were collected by filtration. By recrystallizing the resulting solid from ethanol, 2.5 g of 7-(cyclohexylamino)-1-cyclopentyl-6-fluoro-3-nitroquinolin-4(1H)-one was obtained.

Example 38

To a 4 ml ethanol solution of 220 mg of 3-amino-7-(cyclohexylamino)-1-(1-ethylpropyl)-6-fluoroquinolin-4(1H)-one was added 105 mg of 1H-1,2,3-benzotriazol-1-ylmethanol, followed by overnight stirring at room temperature. Next, 48 mg of sodium borohydride was added to the reaction mixture, followed by stirring for 3 hours. By adding water to the resulting reaction mixture and collecting the insoluble materials by filtration, 100 mg of 7-(cyclohexylamino)-1-(1-ethylpropyl)-6-fluoro-3-(methylamino)quinolin-4(1H)-one was obtained.

Example 39

To a 100 ml dichloromethane solution of 13.8 g of 7-(cyclohexylamino)-1-cyclopentyl-6-fluoro-3-(hydroxymethyl)quinolin-4(1H)-one was added 67.0 g of manganese dioxide at room temperature, followed by overnight stirring. After completion of the reaction and subsequent filtration using celite, the filtrate was evaporated under a reduced pressure. By crystallizing the resulting solid from ethyl acetate, 13.0 g of 7-(cyclohexylamino)-1-cyclopentyl-6-fluoro-4-oxo-1,4-dihydroquinoline-3-carbaldehyde was obtained.

Example 40

6.1 g of metachloroperbenzoic acid was gradually added to a 100 ml of dichloromethane solution of 8.0 g of 7-(cyclohexylamino)-1-cyclopentyl-6-fluoro-4-oxo-1,4-dihydroquinoline-3-carbaldehyde at room temperature, followed by stirring for 2 hours. Aqueous saturated sodium hydrogen carbonate and aqueous sodium hydrogenthiosulfate were added to the reaction mixture, followed by stirring for 30 minutes and then extraction with chloroform. After drying over anhydrous sodium sulfate and subsequent evaporation under a reduced pressure, the residue was purified (Production Methods)

The compound of the present invention and a pharmaceutically acceptable salt thereof may be produced by employing various conventionally known synthesis methods making use of the characteristics based on its basic skeleton or kind of the substituent groups. Typical production methods are exemplified in the following. In this connection, depending on the kinds of functional group, there is an effective case from the production technology point of view to replace said functional group with an appropriate protecting group, namely a group which may be easily converted into said functional group, at the stage of starting material to intermediate. Thereafter, the desired compound may be obtained by removing the protecting group as occasion demands. Examples of the functional group include hydroxyl group, carboxyl group, amino group and the like, and as their protecting groups, the protecting groups described for example in "Protective Groups in Organic Synthesis (third edition)" edited by Greene and Wuts, may be cited, which may be optionally used in response to the reaction conditions.

First Production Method

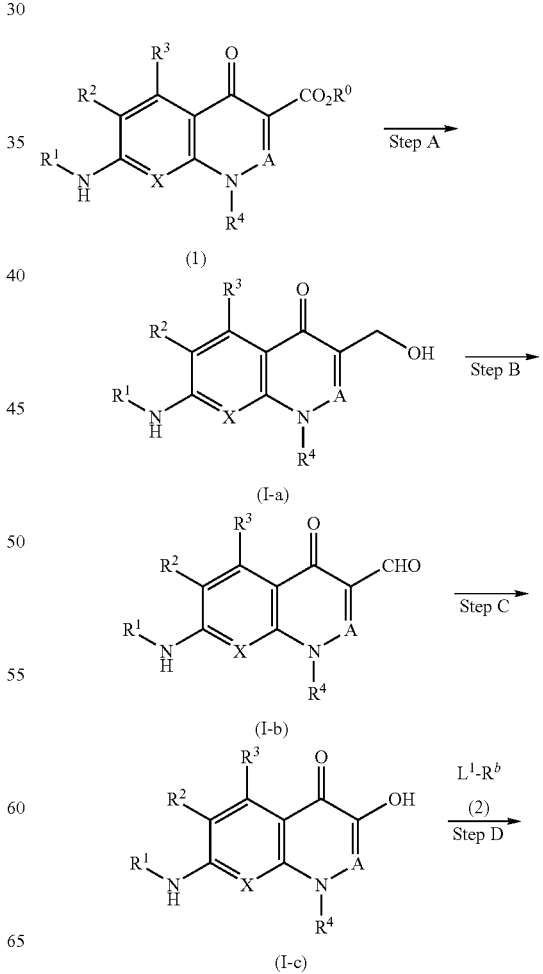

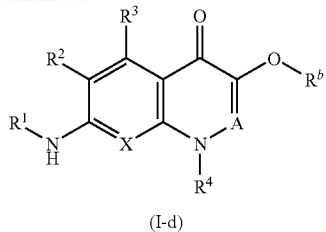

(I-d)

(In the formulae, $L^1$ represents a leaving group such as halogen, —O-methanesulfonyl, —O-p-toluenesulfonyl or the like. The same shall apply hereinafter.) by silica gel column chromatography to obtain 7.7 g of 7-(cyclohexylamino)-1-cyclopentyl-6-fluoro-3-hydroxyquinoline-4(1H)-one.

Example 41

To a 2.0 ml acetic acid solution of 150 mg of 7-(cyclohexylamino)-1-cyclopentyl-6-fluoro-4-oxo-1,4-dihydroquinoline-3-carbaldehyde were added 60 mg of 2-thioxo-1,3-thiazoline-4-one and 40 mg of sodium acetate in that order, followed by overnight stirring at 100° C. The reaction mixture was cooled to room temperature and evaporated under a reduced pressure. Ethyl acetate was added, and the insoluble materials were collected by filtration to obtain 173 mg of 7-(cyclohexylamino)-1-cyclopentyl-6-fluoro-3-[(Z)-(4-oxo-2-thioxo-1,3-thiazolidin-5-ylidene)methyl]quinolin-4(1H)-one.

Example 42

To a 15 ml THF solution of 762 mg of 3-(3-{[tert-butyl(dimethyl)silyl]oxy}propoxy)-7-(cyclohexylamino)-1-cyclopentyl-6-fluoroquinoline-4(1H)-one was added 1.5 ml of a 1 M tetrabutylammonium fluoride THF solution at room temperature, followed by stirring for 2 hours. Water was added to the reaction mixture, followed by extraction with ethyl acetate and washing with aqueous saturated sodium chloride. After drying over anhydrous sodium sulfate, evaporation was carried out under a reduced pressure. By purifying the residue by silica gel column chromatography, 273 mg of 7-(cyclohexylamino)-1-cyclopentyl-6-fluoro-3-(3-hydroxypropoxy)quinolin-4(1H)-one was obtained.

Example 43

To a 10 ml THF solution of 500 mg of 7-(cyclohexylamino)-1-cyclopentyl-6-fluoro-N-methoxy-N-methyl-4-oxo-1,4-dihydroquinoline-3-carboxamide was added 1.2 ml of a 1 M methyl lithium THF solution, followed by stirring at room temperature for 3 days. Water was added to the reaction mixture to carry out celite filtration. After evaporation under a reduced pressure, the resulting residue was purified by silica gel column chromatography to obtain 150 mg of 3-acetyl-7-(cyclohexylamino)-1-cyclopentyl-6-fluoroquinolin-4(1H)-one.

Example 44

To a 5.0 ml dichloromethane solution of 500 mg of 7-(cyclohexylamino)-1-(1-ethylpropyl)-6-fluoro-4-oxo-1,4-dihydroquinoline-3-carbaldehyde were added 0.23 ml of diethyl phosphite and 0.22 ml of 1,8-diazabicyclo[5.4.0]-7-undecene at −40° C., followed by overnight stirring at room temperature. Aqueous saturated ammonium chloride was added to the reaction mixture, followed by extraction with chloroform and then washing with aqueous saturated sodium chloride. After drying over anhydrous sodium sulfate and subsequent evaporation under a reduced pressure, the resulting residue was purified by silica gel column chromatography to obtain 400 mg of diethyl [[7-(cyclohexylamino)-1-(1-ethylpropyl)-6-fluoro-4-oxo-1,4-dihydroquinolin-3-yl](hydroxy)methyl]phosphonate.

Example 45

To a 3.2 ml DMF solution of 160 mg of ethyl {[7-(cyclohexylamino)-1-(1-ethylpropyl)-6-fluoro-4-oxo-1,4-dihydroquinolin-3-yl]amino}acetate were added 0.05 ml of benzyl bromide and 75 mg of potassium carbonate, followed by overnight stirring at room temperature. By adding water to the reaction mixture and collecting the insoluble materials by filtration, 200 mg of ethyl {benzyl[7-(cyclohexylamino)-1-(1-ethylpropyl)-6-fluoro-4-oxo-1,4-dihydro quinolin-3-yl]amino}acetate was obtained.

Example 46

To a 4.2 ml THF solution of 210 mg of (2E)-3-{7-[(cyclopropylmethyl)amino]-6-fluoro-1-isopropyl-4-oxo-1,4-dihydroquinolin-3-yl}acrylic acid was added 120 mg of 1,1'-carbonyldiimidazole, followed by overnight stirring at room temperature. Water was added to the reaction mixture and the insoluble materials were collected by filtration. The resulting solid was dissolved in 4.2 ml of DMF, and 0.11 ml of 1,8-diazabicyclo[5.4.0]-7-undecene and 150 mg of 5-chlorothiophene-2-sulfonamide were added, followed by overnight stirring at 80° C. By adding water to the resulting reaction mixture and collecting the insoluble materials by filtration, 145 mg of (2E)-N-[(5-chloro-2-thienyl)sulfonyl]-3-{7-[(cyclopropylmethyl)amino]-6-fluoro-1-isopropyl-4-oxo-1,4-dihydroquinolin-3-yl}acrylamide was obtained.

Example 47

Under ice-cooling, 2.0 ml of trifluoroacetic acid was added to a 5 ml dichloromethane solution of 0.20 g of tert-butyl {[7-(cyclohexylamino)-6-fluoro-4-oxo-1-(tetrahydrofuran-3-yl)-1,4-dihydroquinolin-3-yl]methyl}carbamate. After stirring under ice-cooling for 1.5 hours and at room temperature overnight, the solvent was evaporated under a reduced pressure. By purifying the resulting residue by an ODS column chromatography, 184 mg of 3-(aminomethyl)-7-(cyclohexylamino)-6-fluoro-1-tetrahydrofuran-3-yl)quinolin-4(1H)-one trifluoroacetate was obtained.

Example 48

To a 4.8 ml DMSO solution of 240 mg of 7-(cyclohexylamino)-1-cyclopentyl-6-fluoro-3-(3-hydroxypropyl)quinolin-4(1H)-one were added 300 mg of a sulfur trioxide pyridine complex and 0.8 ml of triethylamine, followed by overnight stirring at room temperature. Water was added to the reaction mixture, followed by extraction with chloroform and then washing with aqueous saturated sodium chloride. After drying over anhydrous sodium sulfate and subsequent evaporation under a reduced pressure, the resulting residue was purified by silica gel column chromatography to obtain 140 mg of an aldehyde compound. To a 2.8 ml DMF solution of 140 mg of the aldehyde compound were added 141 mg of potassium carbonate and 414 mg of ethyl (diethoxyphosphoryl)acetate, followed by overnight stirring at 60° C. The reaction mixture was cooled to room temperature, water was added, and the insoluble materials were collected by filtration. By purifying the resulting insoluble materials by silica gel column chromatography, 57 mg of ethyl (2E)-5-[7-(cyclohexylamino)-1-cyclopentyl-6-fluoro-4-oxo-1,4-dihydroquinolin-3-yl]pent-2-enoate was obtained.

Example 49

3 ml of ethyl acetate and 0.35 ml of a 1 M hydrogen chloride ethyl acetate solution were added to 0.13 g of ethyl ({[7-(cyclohexylamino)-1-ethyl-6-fluoro-4-oxo-1,4-dihydroquinolin-3-yl]methyl}amino)acetate obtained by the same method of Example 9. After evaporation of the solvent under a reduced pressure and subsequent addition of ether, the insoluble materials were collected by filtration to obtain 97 mg of ethyl({[7-(cyclohexylamino)-1-ethyl-6-fluoro-4-oxo-1,4-dihydroquinolin-3-yl]methyl}amino)acetate hydrochloride.

Example 50

10 ml of ethyl acetate, 45 mg of oxalic acid and 10 ml of ethanol were added to 440 mg of ethyl({[7-(cyclohexylamino)-6-fluoro-4-oxo-1-(tetrahydrofuran-3-yl)-1,4-dihydroquinolin-3-yl]methyl}amino)acetate obtained by the same method of Example 4. After evaporation of the solvent under a reduced pressure and subsequent addition of ethyl acetate, the insoluble materials were collected by filtration to obtain 349 mg of ethyl({[7-(cyclohexylamino)-6-fluoro-4-oxo-1-(tetrahydrofuran-3-yl)-1,4-dihydroquinolin-3-yl]methyl}amino)acetate oxalate.

Example 51

To 0.25 g of ethyl({[7-(cyclohexylamino)-6-fluoro-4-oxo-1-(tetrahydrofuran-3-yl)-1,4-dihydroquinolin-3-yl]methyl}amino)acetate oxalate were added water and potassium carbonate, followed by extraction with chloroform. After drying over anhydrous sodium sulfate and subsequent filtration, the solvent was evaporated under a reduced pressure. To a 10 ml ethanol solution of the resulting residue was added 0.60 ml of aqueous 1 M sodium hydroxide solution under ice-cooling, followed by stirring under ice-cooling for 1 hour and at room temperature overnight. After evaporation of the solvent under a reduced pressure, water and trifluoroacetic acid were added. By purifying by an ODS column chromatography, 251 mg of ({[7-(cyclohexylamino)-6-fluoro-4-oxo-1-(tetrahydro furan-3-yl)-1,4-dihydroquinolin-3-yl]methyl}amino)acetic acid trifluoroacetate was obtained.

Example 52

To a 2.0 ml chloroform solution of 155 mg of diethyl[2-(acetyl{[7-(cyclohexylamino)-1-(1-ethylpropyl)-6-fluoro-4-oxo-1,4-dihydroquinolin-3-yl]methyl}amino)-1,1-difluoroethyl]phosphonate was added 0.27 ml of bromotrimethylsilane, followed by overnight stirring at room temperature. The reaction mixture was evaporated under a reduced pressure, and aqueous 1 M sodium hydroxide solution was added to the resulting residue, followed by purification by an ODS column chromatography and washing with ethyl acetate to obtain 100 mg of disodium [2-(acetyl{[7-(cyclohexylamino)-1-(1-ethylpropyl)-6-fluoro-4-oxo-1,4-dihydroquinolin-3-yl]methyl}amino)-1,1-difluoroethyl] phosphonate.

Example 53

To an 8.0 ml ethanol solution of 280 mg of ethyl (2E)-4-{[7-(cyclohexylamino)-6-fluoro-1-isopropyl-4-oxo-1,4-dihydroquinolin-3-yl]oxy}but-2-enoate was added 28 mg of rhodium-carbon (10%) at room temperature, followed by stirring for 2 hours in an atmosphere of hydrogen. After filtration using celite, the filtrate was evaporated under a reduced pressure, and the residue was purified by silica gel column chromatography to obtain 202 mg of ethyl 4-{[7-(cyclohexylamino)-6-fluoro-1-isopropyl-4-oxo-1,4-dihydroquinolin-3-yl]oxy}butanoate.

Example 54

To a 1.0 ml THF-1.0 ml methanol mixed solution of 130 mg of N-[7-(cyclohexylamino)-1-cyclopentyl-6-fluoro-4-oxo-1,4-dihydroquinolin-3-yl]-2-[(4R)-2,2-dimethyl-5-oxo-1,3-dioxolan-4-yl]acetamide was added 0.3 ml of 1 M hydrochloric acid, followed by overnight stirring at room temperature. Then, 0.8 ml of aqueous 1M sodium hydroxide solution was added, followed by overnight stirring at room temperature. The resulting reaction mixture was neutralized with 1 M hydrochloric acid, and then the insoluble materials were collected by filtration and purified by silica gel column chromatography to obtain 11 mg of (2R)-4-{[7-(cyclohexylamino)-1-cyclopentyl-6-fluoro-4-oxo-1,4-dihydroquinolin-3-yl]amino}-2-hydroxy-4-oxobutanoic acid.

Example 55

To a 2.0 ml THF solution of 100 mg of (2E)-3-[7-(cyclohexylamino)-1-cyclopentyl-6-fluoro-4-oxo-1,4-dihydroquinolin-3-yl]acrylic acid was added 60 mg of 1,1'-carbonyldiimidazole, followed by overnight stirring at room temperature. By adding water to the resulting reaction mixture and collecting the insoluble materials by filtration, an acylimidazole compound was obtained. To a 2.0 ml DMF solution of the resulting acylimidazole compound was added 0.5 ml of aqueous ammonia, followed by overnight stirring at 60° C. The resulting reaction mixture was cooled to room temperature, water was added, and the insoluble materials were collected by filtration to obtain 58 mg of (2E)-3-[7-(cyclohexylamino)-1-cyclopentyl-6-fluoro-4-oxo-1,4-dihydroquinolin-3-yl]acrylamide.

Example 56

To a 5.0 ml ethanol solution of 500 mg of 7-(cyclohexylamino)-1-cyclopentyl-6-fluoro-4-oxo-1,4-dihydroquinoline-3-carbaldehyde was added 215 mg of ethyl aminoacetate hydrochloride, followed by stirring at room temperature for 2 hours. Next, 50 mg of palladium-carbon was added thereto, followed by stirring at room temperature for 4 hours in an atmosphere of hydrogen. The reaction mixture was filtered through celite and then evaporated under a reduced pressure. The resulting residue was purified by silica gel column chromatography. To a 3.6 ml dioxane solution of the resulting compound was added 4.0 ml of a 4 M hydrogen chloride dioxane solution, followed by overnight stirring at room temperature. The insoluble materials were collected by filtration to obtain 320 mg of ethyl({[7-(cyclohexylamino)-1-cyclopentyl-6-fluoro-4-oxo-1,4-dihydroquinolin-3-yl]methyl}amino)acetate hydrochloride.

Example 57

2.0 ml of THF and 0.071 ml of chlorotrimethylsilane were added to 73 mg of zinc, followed by stirring at room temperature for 15 minutes. Then, 200 mg of ethyl (2E)-4-bromobut-2-enoate was added thereto, followed by stirring at room temperature for 30 minutes. To the reaction mixture was added 7-(cyclohexylamino)-1-(1-ethylpropyl)-6-fluoro-4-oxo-1,4-dihydro quinoline-3-carbaldehyde, followed by overnight stirring at room temperature. Water was added to the reaction mixture, followed by extraction with chloroform. The organic layer was washed with aqueous saturated sodium chloride, dried over anhydrous sodium sulfate and then evaporated under a reduced pressure. The resulting residue was purified by silica gel column chromatography to obtain 30 mg of ethyl (2E)-5-[7-(cyclohexylamino)-1-(1-ethylpropyl)-6-fluoro-4-oxo-1,4-dihydroquinolin-3-yl]-5-hydroxypent-2-enoate.

Example 58

To a 5 ml THF solution of 119 mg of 60% sodium hydride was added 598 µl of ethyl(diethoxyphosphoryl)acetate at 0° C., followed by stirring for 30 minutes. A 5 ml THF solution of 400 mg of 7-(cyclohexylamino)-1-cyclopentyl-6-fluoro-3-(2-oxopropoxy)quinolin-4(1H)-one was added thereto at the same temperature, followed by stirring at room temperature for 2 hours. To the reaction mixture was added aqueous saturated ammonium chloride, followed by extraction with ethyl acetate. The organic layer was washed with aqueous saturated sodium chloride, dried over anhydrous sodium sulfate, and concentrated under a reduced pressure. The resulting residue was purified by silica gel column chromatography to obtain 200 mg of ethyl (2E)-4-{[7-(cyclohexylamino)-1-cyclopentyl-6-fluoro-4-oxo-1,4-dihydroquinolin-3-yl]oxy}-3-methylbut-2-enoate.

Example 59

To a 20 ml THF suspension of 1081 mg of (3-benzyloxypropyl)triphenylphosphonium bromide was added 258 mg of potassium, tert-butoxide followed by stirring for 1.5 hours. A 10 ml THF solution of 358 mg of 7-(cyclohexylamino)-1-(1-ethylpropyl)-6-fluoro-4-oxo-1,4-dihydroquinoline-3-carbaldehyde was added thereto, followed by stirring for 1 hour. To the reaction mixture was added aqueous saturated ammonium chloride, followed by extraction with ethyl acetate and washing with aqueous saturated sodium chloride. After drying over anhydrous sodium sulfate and subsequent concentration under a reduced pressure, the residue was purified by silica gel column chromatography to obtain 488 mg of 3-[4-(benzyloxy)but-1-en-1-yl]-7-(cyclohexylamino)-1-(1-ethylpropyl)-6-fluoroquinolin-4(1H)-one.

Example 60

To a 2 ml dichloromethane solution of 100 mg of 5-chlorothiophene-2-carboxylic acid was added 0.55 ml of chlorosulfonyl isocyanate, followed by overnight stirring at 40° C. The solvent was evaporated under a reduced pressure, and the resulting residue was dissolved in 1.5 ml of dichloromethane. Then, 150 mg of 3-amino-7-(cyclohexylamino)-1-cyclopentyl-6-fluoroquinolin-4(1H)-one and 0.91 ml of triethylamine was added, followed by overnight stirring at room temperature. Water was added to the reaction mixture, followed by extraction with chloroform. The organic layer was washed with aqueous saturated sodium chloride. After drying over anhydrous sodium sulfate and subsequent filtration, the solvent was evaporated under a reduced pressure. The resulting residue was purified by silica gel column chromatography to obtain 64 mg of 5-chloro-N-({[7-(cyclohexylamino)-1-cyclopentyl-6-fluoro-4-oxo-1,4-dihydroquinolin-3-yl]amino}sulfonyl)thiophene-2-carboxamide.

Example 61

To a 6 ml DMSO suspension of 200 mg of 60% sodium hydride was added 1.1 g of trimethylsulfoxonium iodide, followed by stirring for 30 minutes. To the reaction mixture was added 242 mg of ethyl (2E)-3-[7-(cyclohexylamino)-1-cyclopentyl-6-fluoro-4-oxo-1,4-dihydroquinolin-3-yl]acrylate, followed by stirring at room temperature for 1 hour and at 60° C. for 1 hour. To the reaction mixture was added water, followed by extraction with diethyl ether. The organic layer was washed with aqueous saturated sodium chloride. After drying over anhydrous sodium sulfate, the solvent was evaporated under a reduced pressure. The resulting residue was purified by silica gel column chromatography to obtain 55 mg of ethyl 2-[7-(cyclohexylamino)-1-cyclopentyl-6-fluoro-4-oxo-1,4-dihydroquinolin-3-yl]cyclopropanecarboxylate.

Example 62

To a 30 ml methanol solution of 1.5 g of {[7-(cyclohexylamino)-1-cyclopentyl-6-fluoro-4-oxo-1,4-dihydroquinolin-3-yl]oxy}acetonitrile were added 1.1 ml of triethylamine and 540 mg of hydroxylamine hydrochloride, followed by heating under reflux for 27 hours. The solvent was evaporated under a reduced pressure, and the resulting residue was purified by silica gel column chromatography to obtain 850 mg of 2-{[7-(cyclohexylamino)-1-cyclopentyl-6-fluoro-4-oxo-1,4-dihydroquinolin-3-yl]oxy}-N'-hydroxyethanimidamide.

Example 63

40 µl of diketene was added dropwise under ice-cooling to a 8 ml chloroform solution of 800 mg of 2-{[7-(cyclohexylamino)-1-cyclopentyl-6-fluoro-4-oxo-1,4-dihydroquinolin-3-yl]oxy}-N'-hydroxyethanimidamide, followed by stirring under ice-cooling for 6 hours. By evaporating the solvent under a reduced pressure, 180 mg of N'-(acetoacetyloxy)-2-{[7-(cyclohexylamino)-1-cyclopentyl-6-fluoro-4-oxo-1,4-dihydroquinolin-3-yl]oxy}ethanimidamide was obtained.

Example 64 and Example 65

5 ml of toluene and 41 mg of 60% sodium hydride were added to 180 mg of N'-(acetoacetyloxy)-2-{[7-(cyclohexylamino)-1-cyclopentyl-6-fluoro-4-oxo-1,4-dihydroquinolin-3yl]oxy}ethanimidamide, followed by heating under reflux for 24 hours. The solvent was evaporated under a reduced pressure, and dilute hydrochloric acid was added to the resulting residue, followed by extraction with ethyl acetate and washing with water and aqueous saturated sodium chloride. After drying over anhydrous sodium sulfate, the solvent was evaporated under a reduced pressure, and the resulting residue was purified by silica gel column chromatography to obtain 10 mg of 7-(cyclohexylamino)-1-cyclopentyl-6-fluoro-3-[(5-oxo-4,5-dihydro-1,2,4-oxadiazol-3-yl)methoxy]quinolin-4(1H)-one (Example 64) and 30 mg of 7-(cyclohexylamino)-1-cyclopentyl-6-fluoro-3-{[5-(2-oxopropyl)-1,2,4-oxadiazol-3-yl]methoxy} quinolin-4(1H)-one (Example 65).

Example 66

0.14 ml of N-(chlorocarbonyl) isocyanate was added dropwise at −50° C. to a 4 ml THF solution of 110 mg of 7-(cyclohexylamino)-1-cyclopentyl-6-fluoro-3-[(hydroxyamino) methyl]quinolin-4(1H)-one, followed by stirring at room temperature for 1 hour. 1 M hydrochloric acid was added to the reaction mixture, followed by extraction with chloroform and washing with aqueous saturated sodium chloride. After drying over anhydrous sodium sulfate, the solvent was evaporated under a reduced pressure, and the resulting residue was purified by silica gel column chromatography to obtain 45 mg of 2-{[7-(cyclohexylamino)-1-cyclopentyl-6-fluoro-4-oxo-1,4-dihydroquinolin-3-yl]methyl}-1,2,4-oxadiazolidine-3,5-dione.

Example 67

To a 4 ml DMSO solution of 310 mg of 7-(cyclohexylamino)-1-cyclopentyl-6-fluoro-3-(4-hydroxybutyl)quinolin-4(1H)-one was added 0.7 ml of triethylamine and 620 mg of a sulfur trioxide pyridine complex, followed by stirring at room temperature for 24 hours. By adding 1 M hydrochloric acid and water, the insoluble materials were collected by filtration to obtain 290 mg of 4-[7-(cyclohexylamino)-1-cyclopentyl-6-fluoro-4-oxo-1,4-dihydroquinolin-3-yl]butanal.

Example 68

To 285 mg of 4-[7-(cyclohexylamino)-1-cyclopentyl-6-fluoro-4-oxo-1,4-dihydroquinolin-3-yl]butanal were added 9 ml of toluene and 250 mg of methyl (triphenylphosphoranilidene)acetate, followed by stirring at 80° C. for 14 hours. The solvent was evaporated under a reduced pressure, and the resulting residue was purified by silica gel column chromatography to obtain 260 mg of methyl (2E)-6-[7-(cyclohexylamino)-1-cyclopentyl-6-fluoro-4-oxo-1,4-dihydroquinolin-3-yl]hex-2-enoate.

Example 69

To 500 mg of 7-(cyclohexylamino)-1-cyclopentyl-6-fluoro-4-oxo-1,4-dihydroquinoline-3-carbaldehyde were added 5 ml of ethanol, 460 mg of sodium acetate and 290 mg of hydroxylamine hydrochloride, followed by stirring at room temperature for 15 hours and at 70° C. for 12 hours. The solvent was evaporated under a reduced pressure, and water was added to the resulting residue, followed by extraction with chloroform and washing with aqueous saturated sodium chloride. After drying over anhydrous sodium sulfate, the solvent was evaporated under a reduced pressure to obtain 300 mg of 7-(cyclohexylamino)-1-cyclopentyl-6-fluoro-4-oxo-1,4-dihydroquinoline-3-carbaldehyde oxime.

Example 70

15 ml of methanol, 15 ml of THF and 250 mg of sodium cyanoborohydride were added to 300 mg of 7-(cyclohexylamino)-1-cyclopentyl-6-fluoro-4-oxo-1,4-dihydroquinoline-3-carbaldehyde oxime. 2 ml of a 4 M hydrogen chloride dioxane solution was added thereto under ice-cooling, followed by stirring at room temperature for 3 hours. Under ice-cooling, aqueous 1 M sodium hydroxide solution was added thereto, followed by extraction with chloroform and subsequent washing with aqueous saturated sodium chloride. After drying over anhydrous sodium sulfate, the solvent was evaporated under a reduced pressure, and the resulting residue was purified by silica gel column chromatography to obtain 130 mg of 7-(cyclohexylamino)-1-cyclopentyl-6-fluoro-3-[(hydroxyamino)methyl]quinolin-4(1H)-one.

Example 71

To a 50 ml THF suspension of 1.02 g of 9-(cyclohexylamino)-8-fluoro-6-oxo-2,3,4,6-tetrahydro-1H-pyrido[1,2-a]quinoline-5-carboxylic acid were added 0.5 ml of triethylamine and 0.4 ml of isobutyl chloroformate under ice-cooling, followed by stirring under ice-cooling for 1 hour. Aqueous solution (4 ml) of 431 mg of sodium borohydride was added dropwise thereto at −78° C., followed by stirring at −15° C. for 15 minutes and under ice-cooling for 30 minute. Aqueous saturated ammonium chloride was added thereto, followed by extraction with ethyl acetate and subsequent drying over anhydrous sodium sulfate. The solvent was evaporated under a reduced pressure, and the resulting residue was purified by silica gel column chromatography to obtain 495 mg of 9-(cyclohexylamino)-8-fluoro-5-(hydroxymethyl)-1,2,3,4-tetrahydro-6H-pyrido[1,2-a]quinolin-6-one.

In the same manner as in the above-mentioned Examples 1 to 71, Example compounds shown in the following Tables 10 to 73 were produced using respectively corresponding starting materials. MS data of the example compounds are shown in the following Tables 10 to 73, and NMR data of several Example compounds in Tables 74 and 75.

Structures of other compounds of the present invention are shown in Tables 76 to 83. These may be easily produced by the use of the above-mentioned production methods, and the methods described in examples or the methods obvious to those skilled in the art, or modified methods thereof.

TABLE 4

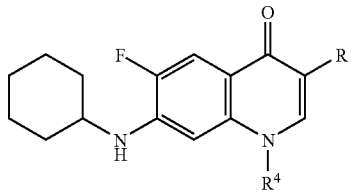

| Rf | RSyn | R⁴ | R | Data |
|----|------|----|----|------|
| 11 | 1 | Et | —C(O)NH₂ | FAB: 332 |
| 12 | 1 | —CH(Et)₂ | —C(O)NH₂ | FAB: 374 |
| 1 | 1 | cPen | —C(O)NH₂ | FAB: 372 |
| 13 | 1 | (tetrahydrofuranyl) | —C(O)NH₂ | FAB: 374 |
| 14 | 1 | (N-Boc-pyrrolidinyl) | —C(O)NH₂ | FAB: 473 |
| 2 | 2 | cPen | —C(O)N(Me)—OMe | FAB: 416 |
| 15 | 9, E37 | —CH(Me)-cyclobutyl | —CO₂H | ESI: 387 |
| 16 | E37, E2 | (3,3-dimethylcyclopentyl-methyl) | —CO₂H | FAB: 401 |

TABLE 5

[Structure: 6,7-difluoro-4-oxo-1-R⁴-quinoline-3-carboxylic acid ethyl ester]

| Rf | RSyn | R⁴ | Data |
|---|---|---|---|
| 10 | 10 | 1-cyclobutylethyl (CH(Me)-cyclobutyl) | ESI: 336 |
| 17 | 10 | 1,1,3-trimethylcyclopentyl | FAB: 350 |

TABLE 6

[Structure: 6,7-difluoro-3-nitro-4-oxo-1-R⁴-quinoline]

| Rf | RSyn | R⁴ | Data |
|---|---|---|---|
| 18 | 3 | iPr | FAB: 269 |
| 19 | 3 | —CH(Et)₂ | ESI: 297 |
| 3 | 3 | cPen | FAB: 295 |
| 20 | 3 | norbornyl (1RS,2RS,4SR) | FAB: 321 |
| 21 | 3 | (2,2,5-trimethyl-1,3-dioxan-5-yl)methyl | FAB: 341 |

TABLE 7

| Rf | RSyn | Structure | Data |
|---|---|---|---|
| 4 | 4 | N-cyclopentyl-3,4,5-trifluoroaniline | EI: 215 |

TABLE 7-continued

| Rf | RSyn | Structure | Data |
|---|---|---|---|
| 5 | 5 | diethyl 2-{[cyclopentyl(3,4,5-trifluorophenyl)amino]methylene}malonate | FAB: 386 |
| 22 | 4 | N-cyclopentyl-3-fluoroaniline | ESI: 180 |

TABLE 8

[Structure: 1-cyclopentyl-4-oxo-1,4-dihydro-naphthyridine/quinoline core with R', R², R³, R substituents and X]

| Rf | RSyn | X | R' | R² | R³ | R | Data |
|---|---|---|---|---|---|---|---|
| 6 | 6 | CH | F | F | F | —CO₂Et | FAB: 340 |
| 23 | 9 | N | Cl | F | H | —CO₂H | FAB: 311 |
| 24 | 5, 6 | CH | F | H | H | —CO₂Et | FAB: 304 |
| 9 | 9 | CH | F | H | H | —CO₂H | FAB: 276 |

TABLE 9

[Structure: 7-cyclohexylamino-1-cyclopentyl-4-oxo-1,4-dihydro core with R², R³ and X]

| Rf | RSyn | X | R² | R³ | Data |
|---|---|---|---|---|---|
| 7 | 7 | CH | F | F | FAB: 391 |
| 8 | 8 | CH | F | —OBn | FAB: 479 |
| 25 | E37 | N | F | H | FAB: 374 |
| 26 | E37 | CH | H | H | FAB: 355 |

TABLE 10

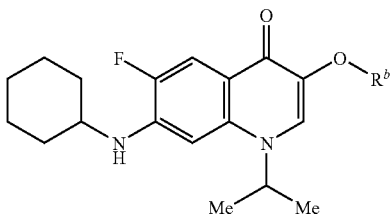

| Ex | Syn | $R^b$ | Data |
|---|---|---|---|
| 72 | 40 | H | FAB: 319 |
| 27 | 27 | —CH$_2$CO$_2$Et | FAB: 405 |
| 73 | 2 | —CH$_2$CO$_2$H | FAB: 377 |
| 74 | 27 | (CH=CH-CH$_2$-)CO$_2$Et | ESI: 431 |
| 75 | 2 | (CH=CH-CH$_2$-)CO$_2$H | FAB: 403 |
| 53 | 53 | —(CH$_2$)$_3$CO$_2$Et | FAB: 433 |
| 76 | 2 | —(CH$_2$)$_3$CO$_2$H | FAB: 405 |
| 77 | 46 | —CH(Me)C(O)NH—S(O)$_2$Me | FAB(Neg): 466 |
| 78 | 46 | —CH(Me)C(O)NH—S(O)$_2$Ph | FAB: 530 |
| 79 | 12 | CH(CO$_2$Me)CH$_2$CH(CO$_2$Me) | FAB: 477 |
| 80 | 2 | CH(CO$_2$H)CH$_2$CH(CO$_2$H) | FAB: 449 |
| 81 | 12 | CH(Me)CO$_2$Me | FAB: 405 |
| 82 | 2 | CH(Me)CO$_2$H | FAB: 391 |
| 83 | Rfl | CH(Me)CONH$_2$ | FAB: 390 |
| 84 | 12 | CH(iBu)CO$_2$Et | ESI: 461 |
| 85 | 2 | CH(iBu)CO$_2$H | FAB: 433 |

TABLE 11

| Ex | Syn | $R^b$ | Data |
|---|---|---|---|
| 86 | 12 | CH(CH$_2$Ph)CO$_2$Bn | FAB: 557 |
| 87 | 2 | CH(CH$_2$Ph)CO$_2$H | ESI: 467 |
| 88 | 27 | 1-methylcyclobutyl-CO$_2$Et | FAB: 445 |
| 89 | 2 | 1-methylcyclobutyl-CO$_2$H | FAB: 417 |

TABLE 12

| Ex | Syn | $R^3$ | $R^b$ | Data |
|---|---|---|---|---|
| 90 | 40 | F | H | FAB: 365 |
| 91 | 27 | | —CH$_2$CO$_2$Et | FAB: 451 |
| 92 | 2 | | —CH$_2$CO$_2$H | FAB: 518 |
| 93 | 40 | H | H | FAB: 347 |
| 94 | 27 | | —CH$_2$CO$_2$Et | FAB: 433 |
| 95 | 2 | | —CH$_2$CO$_2$H | FAB: 405 |
| 96 | 27 | | (CH=CH-CH$_2$-)CO$_2$Et | FAB: 459 |
| 97 | 27 | | —(CH$_2$)$_3$—P(O)(OEt)$_2$ | FAB: 525 |
| 98 | 18 | | —(CH$_2$)$_3$—PO$_3$H$_2$ | FAB: 469 |
| 99 | 12 | | CH(Me)CO$_2$Me | FAB: 433 |
| 100 | 2 | | CH(Me)CO$_2$H | FAB: 419 |

TABLE 13

| Ex | Syn | $R^b$ | Data |
|---|---|---|---|
| 40 | 40 | H | FAB: 345 |
| 101 | 27 | —CH$_2$CO$_2$Et | FAB: 431 |
| 102 | 2 | —CH$_2$CO$_2$H | FAB: 403 |
| 103 | 27 | —C(Me)$_2$CO$_2$Et | FAB: 459 |
| 104 | 2 | —C(Me)$_2$CO$_2$H | FAB: 431 |
| 105 | 11 | —(CH$_2$)$_3$CO$_2$Et | FAB: 459 |
| 106 | 2 | —(CH$_2$)$_3$CO$_2$H | FAB: 431 |

TABLE 13-continued

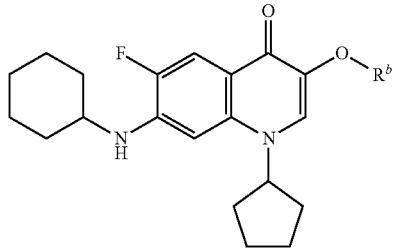

| Ex | Syn | R$^b$ | Data |
|---|---|---|---|
| 107 | 27 | (E)-CH=CHCH(CO2Et)- (crotonate type) | FAB: 457 |
| 108 | 2 | (E)-CH=CHCH-CO2H | FAB: 429 |
| 109 | 24 | C(Ph)=C(Et)CO2Me | FAB: 519 |
| 110 | 11 | —CH$_2$CH(Ph)CH$_2$CO$_2$Me | FAB: 521 |
| 111 | 2 | —CH$_2$CH(Ph)CH$_2$CO$_2$H | FAB: 507 |
| 112 | 12 | CH(CO2Bn)CH2Ph (stereo) | FAB: 583 |
| 113 | 2 | CH(CO2H)CH2Ph (stereo) | FAB: 493 |
| 12 | 12 | CH(CO2Bn)CH2Ph (stereo) | FAB: 583 |
| 114 | 2 | CH(CO2H)CH2Ph (stereo) | FAB: 493 |
| 115 | 12 | CH(Ph)CH2CO2Et (stereo) | FAB: 507 |
| 116 | 2 | CH(Ph)CH2CO2H (stereo) | FAB: 479 |
| 117 | 13 | 2-CN-C6H4-CH2- | FAB: 446 |

TABLE 14

| Ex | Syn | R$^b$ | Data |
|---|---|---|---|
| 118 | 14 | 2-HO2C-C6H4-CH2- | FAB: 465 |
| 14 | 14 | 4-HO2C-C6H4-CH2- | FAB: 465 |
| 13 | 13 | 4-CN-C6H4-CH2- | FAB: 446 |
| 119 | 27 | —CH$_2$C(O)Ph | FAB: 463 |
| 120 | 12 | —(CH$_2$)$_3$—OTBDMS | FAB: 517 |
| 121 | 27 | —(CH$_2$)$_2$—OH | FAB: 389 |
| 42 | 42 | —(CH$_2$)$_3$—OH | ESI: 403 |
| 122 | 12 | CH(CO2Et)CH2CH2Ph (stereo) | FAB: 535 |
| 123 | 2 | CH(CO2H)CH2CH2Ph (stereo) | FAB: 507 |
| 124 | 12 | CH(CO2Me)Me (stereo) | FAB: 431 |
| 125 | 2 | CH(CO2H)Me (stereo) | FAB: 417 |
| 126 | 27 | CH(CO2Et)Et (stereo) | FAB: 459 |
| 127 | 2 | CH(CO2H)Et (stereo) | FAB: 431 |
| 128 | 12 | CH(CO2Me)Me (stereo) | FAB: 431 |
| 129 | 2 | CH(CO2H)Me (stereo) | FAB: 417 |
| 130 | 12 | CH(CO2Et)iBu (stereo) | FAB: 487 |
| 131 | 2 | CH(CO2H)iBu (stereo) | FAB: 459 |
| 132 | 12 | CH(CO2Me)cHex (stereo) | FAB: 499 |
| 133 | 2 | CH(CO2H)cHex (stereo) | FAB: 485 |

TABLE 15

| | | | |
|---|---|---|---|
| 134 | 12 | [CH(Me)-CH=CH-CO2Me] | FAB: 457 |
| 135 | 2 | [CH(Me)-CH=CH-CO2H] | ACPI: 443 |
| 136 | 53 | [CH(Me)-CH2-CH2-CO2Me] | FAB: 459 |
| 137 | 2 | [CH(Me)-CH2-CH2-CO2H] | FAB: 445 |
| 138 | 12 | [CH(CO2Me)-CH2-CH2-CO2Me] | FAB: 503 |
| 139 | 2 | [CH(CO2H)-CH2-CH2-CO2H] | FAB: 475 |
| 140 | 27 | —CH2CN | FAB: 384 |
| 32 | 32 | [ethyl-tetrazole] | FAB: 427 |
| 141 | 2 | [C(Me)(Et)=CH-CO2H] | FAB: 443 |
| 142 | 27 | [C(=O)-Et... Me] | FAB: 401 |
| 58 | 58 | [C(Me)(Et)=CH-CO2Et] | FAB: 471 |
| 143 | 53 | [CH(Me)(Et)-CH2-CO2H] | FAB: 445 |
| 144 | 2 | [CH(iPr)-CO2H] | FAB: 445 |
| 145 | 12 | —(CH2)4—CO2Me | FAB: 459 |
| 146 | 2 | —(CH2)4—CO2H | FAB: 445 |
| 147 | 12 | [C(Me)=CH-Et with CO2Et] | FAB: 471 |
| 148 | 2 | [C(Me)=CH-Et with CO2H] | FAB: 443 |
| 149 | 53 | [CH(Me)(Pr)-CO2H] | FAB: 445 |

TABLE 16

| | | | |
|---|---|---|---|
| 62 | 62 | [C(=NOH)(NH2)-Et] | FAB: 417 |
| 63 | 63 | [C(=N-O-C(=O)CH2C(=O)Me)(NH2)-Et] | FAB: 501 |
| 64 | 64 | [3-ethyl-1,2,4-oxadiazol-5(4H)-one] | FAB: 443 |
| 65 | 65 | [3-ethyl-5-(2-oxopropyl)-1,2,4-oxadiazole] | FAB: 483 |
| 150 | 27 | [3-ethylphenyl-CO2Me] | FAB: 493 |
| 151 | 2 | [3-ethylphenyl-CO2H] | FAB: 479 |

TABLE 17

[Quinolinone core with F, cyclohexylamino, R⁴ on N, O-R^b on 3-position, 4-oxo]

| Ex | Syn | R⁴ | R^b | Data |
|---|---|---|---|---|
| 152 | 40 | [norbornyl (1RS,2RS,4SR)] | H | FAB: 371 |
| 153 | 27 | | —CH2CO2Et | FAB: 457 |
| 154 | 2 | | —CH2CO2H | FAB: 429 |
| 155 | 40 | [CH(Me)-cyclobutyl] | H | FAB: 359 |
| 156 | 27 | | —CH2CO2Et | FAB:: 445 |
| 157 | 2 | | —CH2CO2H | FAB: 417 |
| 158 | 40 | —CH2CF3 | H | FAB: 359 |
| 159 | 27 | | —CH2CO2Et | ESI: 445 |
| 160 | 2 | | —CH2CO2H | FAB: 417 |

TABLE 17-continued

[Structure: 7-cyclohexylamino-6-fluoro-3-OR^b-1-R^4-quinolin-4(1H)-one]

| Ex | Syn | R^4 | R^b | Data |
|---|---|---|---|---|
| 161 | 40 | [3-methylcyclopentyl] | H | FAB: 373 |
| 162 | 27 | [1,3-dimethylcyclopentyl] | —CH₂CO₂Et | FAB:: 459 |
| 163 | 2 | [1,3-dimethylcyclopentyl] | —CH₂CO₂H | FAB: 431 |

TABLE 18

[Structure: 7-cyclohexylamino-5,6-difluoro-1-cyclopentyl-3-OR^b-quinolin-4(1H)-one]

| Ex | Syn | R^b | Data |
|---|---|---|---|
| 164 | 40 | H | FAB: 363 |
| 165 | 12 | (S)-CH(Me)CO₂Me | FAB: 449 |
| 166 | 2 | (S)-CH(Me)CO₂H | FAB: 435 |

TABLE 19

[Structure: 7-cyclohexylamino-1-cyclopentyl-3-OR^b-quinolin-4(1H)-one]

| Ex | Syn | R^b | Data |
|---|---|---|---|
| 167 | 40 | H | ESI: 327 |
| 168 | 2 | (S)-CH(Me)CO₂H | FAB: 399 |
| 169 | 2 | (S)-CH(Et)CO₂H | FAB: 413 |
| 170 | 12 | (S)-CH(Me)CO₂Me | FAB: 413 |
| 171 | 12 | (S)-CH(Et)CO₂Me | ESI: 427 |

TABLE 20

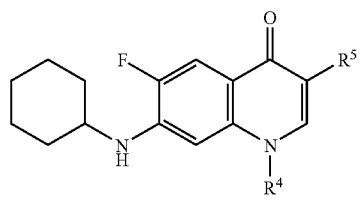

| Ex | Syn | R^4 | R^5 | Data |
|---|---|---|---|---|
| 172 | 37 | iPr | —NO₂ | ESI: 320 |
| 173 | 11 | iPr | —NH₂ | ESI: 290 |
| 174 | 37 | —CH(Et)₂ | —NO₂ | ESI: 348 |
| 175 | 11 | —CH(Et)₂ | —NH₂ | ESI: 318 |
| 176 | 37 | cPen | —NO₂ | FAB: 346 |
| 177 | 11 | cPen | —NH₂ | ESI: 316 |

TABLE 21

[Structure: 7-cyclohexylamino-6-fluoro-3-R^5-1-R^4-quinolin-4(1H)-one]

| Ex | Syn | R^4 | R^5 | Data |
|---|---|---|---|---|
| 178 | 37 | iPr | —NO₂ | ESI: 348 |
| 179 | 11 | iPr | —NH₂ | ESI: 318 |
| 180 | 37 | —CH(Et)₂ | —NO₂ | FAB: 376 |

TABLE 21-continued
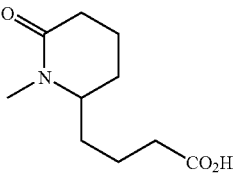
| Ex | Syn | R⁴ | R⁵ | Data |
|---|---|---|---|---|
| 181 | 11 | | —NH₂ | FAB: 346 |
| 38 | 38 | | —NHMe | FAB: 360 |
| 182 | 9 | | —NHCH₂CO₂Et | FAB: 432 |
| 183 | 2 | | —NHCH₂CO₂H | ESI: 404 |
| 45 | 45 | | —N(Bn)CH₂CO₂Et | FAB: 522 |
| 184 | 2 | | —N(Bn)CH₂CO₂H | ESI: 494 |
| 185 | 10 | | —N(Bz)CH₂CO₂Et | FAB: 536 |
| 186 | 2 | | —N(Bz)CH₂CO₂H | FAB: 508 |
| 187 | 5 | | 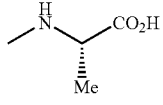 | ESI: 514 |
| 37 | 37 | cPen | —NO₂ | FAB: 374 |
| 188 | 11 | | —NH₂ | FAB: 314 |
| 189 | 9,2 | | 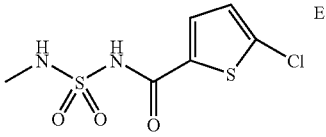 | ESI: 416 |
| 60 | 60 | | 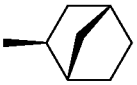 | ESI(neg): 565 |
| 190 | 37 | 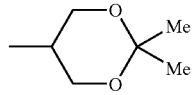<br>(1RS,2RS,4SR) | —NO₂ | FAB: 400 |
| 191 | 11 | | —NH₂ | FAB: 370 |
| 192 | 37 | 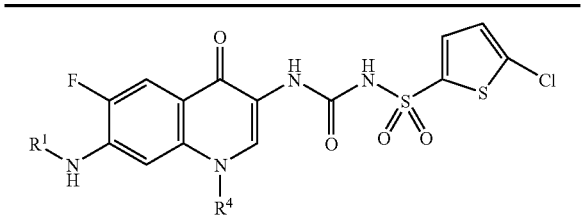 | —NO₂ | FAB: 420 |
| 193 | 11 | | —NH₂ | FAB: 390 |
TABLE 22
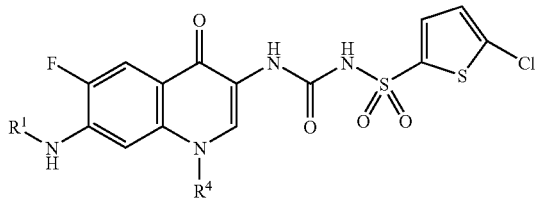
| Ex | Syn | R¹ | R⁴ | Data |
|---|---|---|---|---|
| 194 | 8 | cPr—CH₂— | iPr | FAB: 513 |
| 195 | 8 | | cPen | ESI: 539 |
| 8 | 8 | cHex | iPr | ESI: 541 |
| 196 | 8 | | —CH(Et)₂ | FAB: 569 |
| 197 | 8 | | cPen | FAB: 567 |

TABLE 23

| Ex | Syn | R⁴ | Rᵉ | Data |
|---|---|---|---|---|
| 198 | 8 | iPr | —SO₂—Ph | FAB: 501 |
| 199 | 8 | | —SO₂—Me | FAB: 439 |
| 200 | 8 | | 4-Cl-C₆H₄-SO₂- | FAB: 535 |
| 7 | 7 | —CH(Et)₂ | —(CH₂)₂—CO₂Et | FAB: 489 |
| 201 | 2 | | —(CH₂)₂—CO₂H | ESI: 461 |
| 202 | 7 | cPen | —(CH₂)₂—CO₂H | ESI: 459 |
| 203 | 2 | | —(CH₂)₂—CO₂Et | FAB: 487 |
| 204 | 7 | | 3-CO₂Me-C₆H₄-CH₂- | FAB: 521 |
| 205 | 2 | | 3-CO₂H-C₆H₄-CH₂- | FAB: 507 |
| 206 | 7 | | —CH(Me)CH₂CO₂Et | FAB: 501 |
| 207 | 2 | | —CH(Me)CH₂CO₂H | FAB: 473 |

TABLE 24

| Ex | Syn | R⁶ | Rᵈ | Data |
|---|---|---|---|---|
| 208 | 1 | Me | —(CH₂)₂—CO₂Et | FAB: 488 |
| 209 | 2 | | —(CH₂)₂—CO₂H | FAB: 460 |
| 10 | 10 | —CH₂CO₂Et | —(CH₂)₃—CO₂Et | FAB: 574 |
| 210 | 2 | —CH₂CO₂H | —(CH₂)₃—CO₂H | FAB: 518 |

TABLE 25

| Ex | Syn | R⁴ | Rᵈ | Data |
|---|---|---|---|---|
| 211 | 1 | iPr | —(CH₂)₃—CO₂Et | FAB: 432 |
| 212 | 2 | | —(CH₂)₃—CO₂H | FAB: 404 |
| 213 | 1 | —CH(Et)₂ | —(CH₂)₃—CO₂Et | FAB: 460 |
| 214 | 2 | | —(CH₂)₃—CO₂H | FAB: 432 |
| 215 | 1 | cPen | —(CH₂)₃—CO₂Et | ESI: 458 |
| 216 | 2 | | —(CH₂)₃—CO₂H | FAB: 430 |
| 217 | 1 | | 2-Me-C₆H₄-CH₂-CO₂H | FAB: 478 |
| 218 | 2 | | 2-Me-C₆H₄-CH₂-CO₂Me | FAB: 492 |

TABLE 26

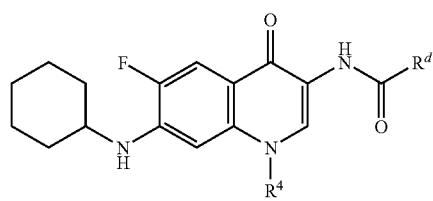

| Ex | Syn | R⁴ | Rᵈ | Data |
|---|---|---|---|---|
| 219 | 1 | iPr | —(CH₂)₂—CO₂Et | FAB: 446 |
| 220 | 2 | | —(CH₂)₂—CO₂H | FAB: 418 |
| 221 | 1 | | —(CH₂)₃—CO₂Et | FAB: 460 |
| 222 | 2 | | —(CH₂)₃—CO₂H | FAB: 432 |
| 223 | 1 | | —(CH₂)₃—CO₂—(CH₂)₂—NMe₂ | FAB: 503 |

TABLE 26-continued

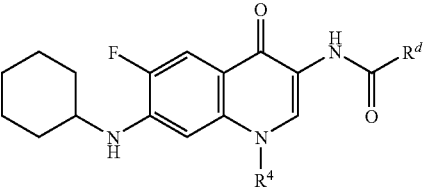

| Ex | Syn | R⁴ | Rᵈ | Data |
|---|---|---|---|---|
| 224 | 2 | | 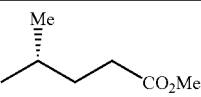 | FAB: 460 |
| 225 | 1 | | 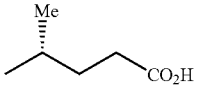 | FAB: 446 |
| 226 | 2 | 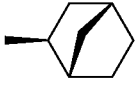 (1RS, 2RS, 4SR) | —(CH₂)₃—CO₂Et | FAB: 512 |
| 227 | 1 | | —(CH₂)₃—CO₂H | FAB: 484 |
| 228 | 2 | 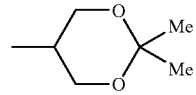 | —(CH₂)₃—CO₂Et | FAB: 532 |
| 229 | 1 | | —(CH₂)₃—CO₂H | FAB: 504 |

TABLE 27

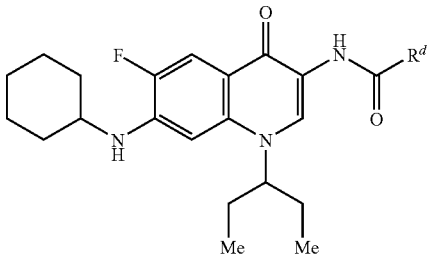

| Ex | Syn | Rᵈ | Data |
|---|---|---|---|
| 230 | 1 | —CH₂CO₂Et | FAB: 460 |
| 231 | 2 | —CH₂CO₂H | FAB: 432 |
| 232 | 1 | —(CH₂)₂CO₂Et | FAB: 474 |
| 233 | 2 | —(CH₂)₂CO₂H | FAB: 446 |
| 234 | 1 | —(CH₂)₃CO₂Et | FAB: 488 |
| 235 | 2 | —(CH₂)₃CO₂H | FAB: 460 |
| 236 | 1,2 | —(CH₂)₄—CO₂H | FAB: 474 |
| 237 | 2 | 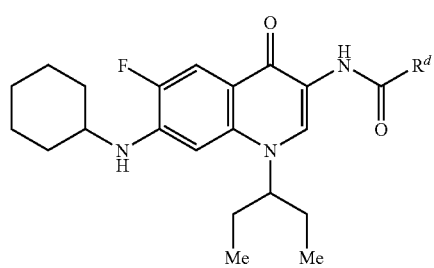 | FAB: 474 |
| 238 | 1 | 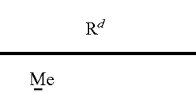 | FAB: 460 |
| 239 | 2 | —CH(Et)CO₂Et | FAB: 488 |
| 240 | 1 | —CH(Et)CO₂H | FAB: 460 |
| 241 | 2 | —C(Me)₂CO₂Et | FAB: 488 |
| 242 | 1 | —C(Me)₂CO₂H | FAB: 460 |
| 243 | 2 | 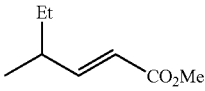 | FAB: 488 |

TABLE 27-continued

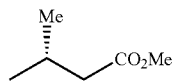

| Ex | Syn | Rᵈ | Data |
|---|---|---|---|
| 244 | 1 | 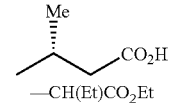 | FAB: 474 |
| 245 | 2 | —CH₂CH(Me)CH₂CO₂Me | FAB: 488 |
| 246 | 1 | —CH₂CH(Me)CH₂CO₂H | FAB: 474 |
| 30 | 30 |  | FAB: 500 |
| 247 | 11 | —CH(Et)—(CH₂)₂—CO₂Me | FAB: 502 |
| 248 | 2 | —CH(Et)—(CH₂)₂—CO₂H | FAB: 488 |
| 249 | 1 | 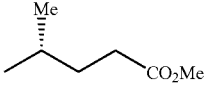 | FAB: 458 |

TABLE 28

| | | | |
|---|---|---|---|
| 250 | 1 | (S)-5-methyl-dihydrofuran-2(3H)-one | FAB: 458 |
| 251 | 2 | (R)-4-hydroxypentanoic acid structure (OH, CO₂H) | FAB: 476 |
| 252 | 2 | (S)-4-hydroxypentanoic acid structure (OH, CO₂H) | FAB: 476 |
| 253 | 1 | —(CH₂)₂—CH(Ph)CO₂Et | ESI: 564 |
| 254 | 2 | —(CH₂)₂—CH(Ph)CO₂H | ESI: 536 |
| 255 | 2 | —CH₂CH(Ph)CH₂CO₂H | FAB: 536 |
| 256 | 1 | —CH₂CH(Ph)CH₂CO₂Et | FAB: 564 |
| 257 | 1 | —CH₂OCH₂CO₂Et | ESI: 490 |
| 258 | 2 | —CH₂OCH₂CO₂H | FAB: 462 |
| 9 | 9 | N(CH₂CO₂Et)(CH₂CO₂Et) with ethyl | ESI: 575 |
| 259 | 2 | N(CH₂CO₂H)(CH₂CO₂H) with ethyl | ESI: 519 |
| 260 | 2 | —(CH₂)₂—P(O)(OEt)₂ | FAB: 538 |
| 261 | 52 | —(CH₂)₂—PO₃Na₂ | FAB: 482 (M⁺ − 2Na + 3) |
| 262 | 1 | —CH₂NHBoc | FAB: 503 |
| 28 | 28 | —CH₂NH₂ | FAB: 403; Sal: 2HCl |
| 263 | 29 | —CH(Et)CH₂OH | FAB: 446 |
| 264 | 2 | trans-6-methylcyclohex-3-ene-1-carboxylic acid | ESI: 498 |
| 265 | 2 | trans-2-methylcyclohexane-1-carboxylic acid | FAB: 500 |
| 266 | 1 | trans-6-methylcyclohex-3-ene-1-carboxylic acid methyl ester | FAB: 512 |

TABLE 29

| | | | |
|---|---|---|---|
| 267 | 11 | cis-2-methylcyclohexane-1-carboxylic acid methyl ester | ESI: 514 |
| 268 | 1 | 3,5-bis(CO₂Et)-toluene | FAB: 594 |
| 269 | 2 | 3,5-bis(CO₂H)-toluene | FAB: 538 |

TABLE 30

Structure: quinolinone with cyclohexylamino, F, cyclopentyl-N, and NHC(O)Rᵈ substituents

| Ex | Syn | Rᵈ | Data |
|---|---|---|---|
| 1 | 1 | —(CH₂)₂—CO₂Et | FAB: 472 |
| 2 | 2 | —(CH₂)₂—CO₂H | FAB: 444 |
| 270 | 1 | —(CH₂)₃—CO₂Et | FAB: 486 |
| 271 | 2 | —(CH₂)₃—CO₂H | FAB: 458 |
| 272 | 1 | —(CH₂)₄—CO₂Et | FAB: 500 |
| 273 | 2 | —(CH₂)₄—CO₂H | FAB: 472 |
| 274 | 1 | (E)-CH=CH-CO₂Et | FAB: 470 |
| 275 | 2 | (E)-CH=CH-CO₂H | FAB: 442 |
| 276 | 1 | (R)-4-methylpentanoic acid methyl ester | APCI: 486 |
| 277 | 2 | (R)-4-methylpentanoic acid | FAB: 472 |
| 278 | 1 | (S)-4-ethyl-2,2-dimethyl-1,3-dioxolan-5-one | FAB: 500 |
| 54 | 54 | (S)-2-hydroxybutanoic acid | FAB: 460 |
| 279 | 1 | —CH₂CH(Ph)CH₂CO₂Et | FAB: 562 |
| 280 | 2 | —CH₂CH(Ph)CH₂CO₂H | FAB: 534 |
| 281 | 1 | —(CH₂)₂—P(O)(OEt)₂ | FAB: 536 |
| 282 | 3 | —(CH₂)₂—PO₃H₂ | FAB: 480 Sal: HBr |

TABLE 30-continued
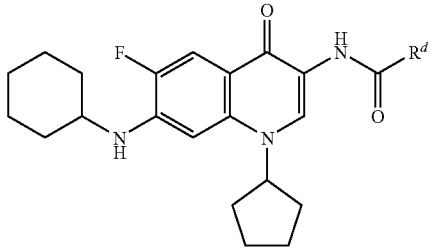
| Ex | Syn | R$^d$ | Data |
|---|---|---|---|
| 283 | 1 | 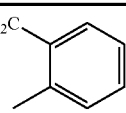 | FAB: 506 |
TABLE 31
| Ex | Syn | R$^d$ | Data |
|---|---|---|---|
| 284 | 2 | 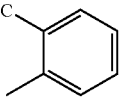 | FAB: 492 |
| 285 | 1 | 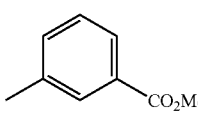 | FAB: 506 |
| 286 | 2 | 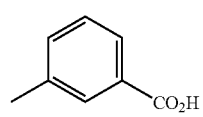 | FAB: 492 |
| 287 | 1 | 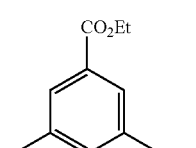 | FAB: 592 |
| 288 | 2 | 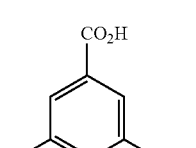 | FAB: 564 |
| 289 | 2 | 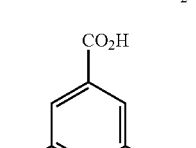 | FAB: 536 |
| 290 | 10 | —CO$_2$Et | FAB: 444 |
| 291 | 2 | —CO$_2$H | ESI: 416 |
| 292 | 2 | 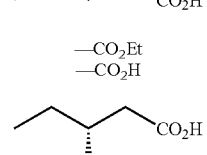 | FAB: 474 |
| 293 | 1 | 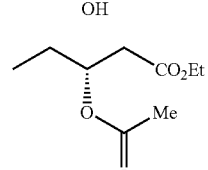 | ESI: 544 |
TABLE 32
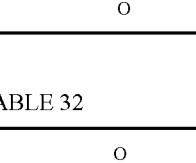
| Ex | Syn | R$^4$ | R$^5$ | Data |
|---|---|---|---|---|
| 294 | 29 | cPen | —CH$_2$OH | FAB: 331 |
| 295 | 39 | | —CHO | FAB: 329 |
| 296 | 24 | | 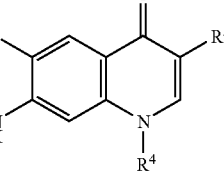 | FAB: 399 |
| 297 | 2 | | 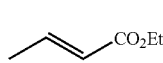 | ESI: 371 |
| 298 | 29 | iPr | —CH$_2$OH | FAB: 305 |
| 299 | 39 | | —CHO | FAB: 303 |
| 300 | 24 | | 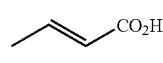 | FAB: 373 |
| 301 | 2 | | 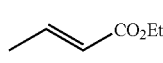 | FAB: 345 |

TABLE 32-continued

Structure: 7-(cyclopropylmethylamino)-6-fluoro-quinolin-4(1H)-one with R⁴ on N1 and R⁵ at C3

| Ex | Syn | R⁴ | R⁵ | Data |
|---|---|---|---|---|
| 46 | 46 | (but-2-enoyl-N-H sulfonyl-5-chlorothiophen-2-yl) | | FAB: 524 |

TABLE 33

Structure: 7-cyclohexylamino-6-fluoro-1-(pentan-3-yl)-quinolin-4(1H)-one with R³ at C5 and R⁵ at C3

| Ex | Syn | R³ | R⁵ | Data |
|---|---|---|---|---|
| 302 | 29 | F | —CH₂OH | FAB: 379 |
| 303 | 39 |   | —CHO | FAB: 377 |
| 304 | 24 |   | CH=CH-CO₂Et (trans) | FAB: 447 |
| 305 | 2 |   | CH=CH-CO₂H (trans) | FAB: 419 |
| 306 | 29 | —OBn | —CH₂OH | ESI: 467 |
| 307 | 11 | —OH | —CH₂OH | ESI: 377 |
| 308 | 39 |   | —CHO | FAB (Ne): 373 |
| 309 | 24 |   | CH=CH-CO₂Et (trans) | FAB: 45 |
| 310 | 2 |   | CH=CH-CO₂H (trans) | FAB: 417 |
| 311 | 2 |   | CH=CH-C(O)N(CH₂CO₂H)₂ | ESI: 532 |
| 312 | 2 |   | CH=CH-C(O)N(CH₂CO₂H)(CH₂CO₂Et) | FAB: 560 |
| 313 | 1 |   | CH=CH-C(O)N(CH₂CO₂Et)₂ | FAB: 58 |
| 314 | 24 |   | CH=CH-P(O)(OEt)₂ | ESI: 509 |
| 315 | 3 |   | CH=CH-PO₃H₂ | ESI: 453 Sal: HBr |

TABLE 34

[Structure: cyclohexyl-NH-substituted fluoroquinolinone core with R⁴ on N and R⁵ at 3-position]

| Ex | Syn | R⁴ | R⁵ | Data |
|---|---|---|---|---|
| 316 | 29 | Et | —CH₂OH | FAB: 319 |
| 317 | 39 | Et | —CHO | FAB: 317 |
| 318 | 29 | iPr | —CH₂OH | FAB: 333 |
| 319 | 39 | iPr | —CHO | FAB: 331 |
| 320 | 24 | Et | ⟋═⟍CO₂Et | FAB: 401 |
| 321 | 2 | Et | ⟋═⟍CO₂H | ESI: 373 |
| 322 | 41 | Et | 5-ethylidene-2-thioxothiazolidin-4-one | FAB: 446 |
| 323 | 46 | Et | ⟋═⟍C(O)NHSO₂Me | FAB: 450 |
| 324 | 46 | Et | ⟋═⟍C(O)NHSO₂Ph | FAB: 512 |
| 325 | 55 | Et | ⟋═⟍C(O)NH-C₆H₄-CO₂Me | ESI: 506 |
| 326 | 29 | 3-methyl-tetrahydrofuran-3-yl | —CH₂OH | FAB: 361 |
| 327 | 29 | (S)-tetrahydrofuran-3-yl | —CH₂OH | FAB: 361 |
| 328 | 39 | (S)-tetrahydrofuran-3-yl | —CHO | FAB: 359 |
| 329 | 24 | (S)-tetrahydrofuran-3-yl | ⟋═⟍CO₂Et | FAB: 429 |
| 330 | 2 | (S)-tetrahydrofuran-3-yl | ⟋═⟍CO₂H | FAB: 401 |
| 331 | 29 | (R)-tetrahydrofuran-3-yl | —CH₂OH | FAB: 361 |
| 332 | 39 | (R)-tetrahydrofuran-3-yl | —CHO | FAB: 359 |
| 333 | 24 | (R)-tetrahydrofuran-3-yl | ⟋═⟍CO₂Et | FAB: 429 |
| 334 | 2 | (R)-tetrahydrofuran-3-yl | ⟋═⟍CO₂H | FAB: 401 |

TABLE 35

| | | | | |
|---|---|---|---|---|
| 335 | 28 | 3-methylpyrrolidine (NH) | —CH$_2$OH | FAB: 360 Sal: 2HCl |
| 336 | 5 | 1-Me-3-methylpyrrolidine | —CH$_2$OH | FAB: 374 |
| 337 | 29 | 1-Boc-3-methylpyrrolidine | —CH$_2$OH | FAB: 460 |
| 338 | 29 | 1-(SO$_2$Me)-3-methylpyrrolidine | —CH$_2$OH | FAB: 438 |
| 339 | 29 | 1-Me-4-methylpiperidine | —CH$_2$OH | FAB: 388 |
| 340 | 29 | —CH(Me)(cBu) | —CH$_2$OH | FAB: 373 |
| 341 | 39 | —CH(Me)(cBu) | —CHO | FAB: 371 |
| 342 | 29 | —CH$_2$CF$_3$ | —CH$_2$OH | FAB: 373 |
| 343 | 39 | —CH$_2$CF$_3$ | —CHO | FAB: 371 |
| 344 | 29 | 3,3-dimethylcyclopentyl | —CH$_2$OH | FAB: 387 |
| 345 | 39 | 3,3-dimethylcyclopentyl | —CHO | FAB: 385 |
| 346 | 29 | norbornyl (1RS, 2RS, 4SR) | —CH$_2$OH | FAB: 385 |
| 347 | 39 | norbornyl (1RS, 2RS, 4SR) | —CHO | FAB: 383 |

TABLE 36

[Structure: 7-(cyclohexylamino)-6-fluoro-1-(pentan-3-yl)-4-oxo-1,4-dihydroquinoline with R$^5$ at 3-position]

| Ex | Syn | R$^5$ | Data |
|---|---|---|---|
| 348 | 29 | —CH$_2$OH | FAB: 361 |
| 349 | 39 | —CHO | FAB: 359 |
| 350 | 11 | —(CH$_2$)$_4$—OH | FAB: 403 |
| 351 | 6 | —CH=CH—CH$_2$—OAc | ESI(Neg): 427 |
| 352 | 29 | —CH=CH—CH$_2$—OH | ESI: 387 |
| 59 | 59 | —CH=CH—(CH$_2$)$_2$—OBn | FAB: 491 |
| 353 | 24 | —CH=CH—CO$_2$Et | FAB: 429 |

TABLE 36-continued

[Same core structure]

| Ex | Syn | R$^5$ | Data |
|---|---|---|---|
| 354 | 2 | —CH=CH—CO$_2$H | FAB: 401 |
| 355 | 11 | —(CH$_2$)$_2$—CO$_2$Et | FAB: 431 |
| 356 | 2 | —(CH$_2$)$_2$—CO$_2$H | FAB: 403 |
| 357 | 24 | —C(F)=C(Me)—CO$_2$Et | ESI(Neg): 445 |
| 358 | 2 | —C(F)=C(Me)—CO$_2$H | FAB: 419 |
| 359 | 24 | —C(Cl)=C(Me)—CO$_2$Et | ESI(Neg): 461 |
| 360 | 2 | —C(Cl)=C(Me)—CO$_2$H | FAB: 435 |
| 57 | 57 | —CH=CH—CH$_2$—CH(OH)—Me, CO$_2$Et | ESI: 473 |
| 361 | 2 | —CH=CH—CH$_2$—CH(OH)—Me, CO$_2$H | FAB: 445 |
| 362 | 1 | —CH=CH—C(O)—NH—CH$_2$—CO$_2$Et | FAB: 486 |
| 363 | 2 | —CH=CH—C(O)—NH—CH$_2$—CO$_2$H | FAB: 458 |

TABLE 37

| 364 | 1 | —CH=CH—C(O)—N(CH$_2$CO$_2$Et)$_2$ | FAB: 572 |

TABLE 37-continued

| | | | |
|---|---|---|---|
| 365 | 2 |  | ESI: 544 |
| 366 | 2 | 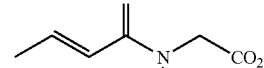 | FAB: 516 |
| 367 | 11 | 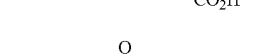 | FAB: 574 |
| 368 | 2 |  | ESI(Neg): 516 |
| 369 | 11 | —(CH$_2$)$_2$—P(O)(OEt)$_2$ | FAB: 495 |
| 370 | 18 | —(CH$_2$)$_2$—PO$_3$H$_2$ | FAB: 439 |
| 21 | 21 | —(CH$_2$)$_4$—Br | FAB: 465 |
| 22 | 22 | —(CH$_2$)$_4$—P(O)(OEt)$_2$ | FAB: 523 |
| 371 | 18 | —(CH$_2$)$_4$—PO$_3$H$_2$ | FAB: 467 Sal: HCl |
| 44 | 44 | —CH(OH)P(O)(OEt)$_2$ | FAB: 497 |
| 372 | 18 | —CH(OH)PO$_3$H$_2$ | FAB: 441 |
| 23 | 23 | —CH(OH)CF$_2$P(O)(OEt)$_2$ | ESI(Neg): 545 |
| 373 | 18 | —CH(OH)CF$_2$PO$_3$H$_2$ | FAB: 491 |
| 374 | 24 |  P(O)(OEt)$_2$ | FAB: 493 |
| 3 | 3 |  PO$_3$H$_2$ | FAB: 437 Sal: HBr |
| 18 | 18 |  PO$_3$H$_2$ | FAB: 437 |

TABLE 38

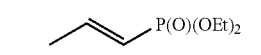

| Ex | Syn | R$^{pa}$ | R$^{pb}$ | Data |
|---|---|---|---|---|
| 375 | 26 | H | —CH$_2$OC(O)OiPr | FAB: 553 |
| 26 | 26 | H | —CH$_2$OC(O)OtBu | FAB(Neg): 549 |
| 25 | 25 | —CH$_2$OC(O)OtBu | —CH$_2$OC(O)OtBu | FAB: 665 |
| 376 | 25 | —CH(Me)OC(O)-cHex | —CH(Me)OC(O)-cHex | ESI: 777 |
| 377 | 25 | —CH(Me)OC(O)-tBu | —CH(Me)OC(O)-tBu | FAB: 693 |

TABLE 39

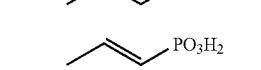

| Ex | Syn | R$^5$ | Data | |
|---|---|---|---|---|
| 29 | 29 | —CH$_2$OH | FAB: | 359 |
| 39 | 39 | —CHO | FAB: | 357 |
| 19 | 19 | —(CH$_2$)$_2$—OH | FAB: | 373 |
| 31 | 31 | —(CH$_2$)$_3$—OH | FAB: | 387 |
| 43 | 43 | Ac | FAB: | 371 |
| 378 | 2 | —(CH$_2$)$_2$—CO$_2$H | FAB: | 401 |
| 16 | 16 | —CH(OH)CO$_2$Me | FAB: | 417 |
| 15 | 15 | —CH(OH)CO$_2$H | FAB: | 403 |
| 17 | 17 | —CH(CO$_2$Me)—OCH$_2$CO$_2$Et | FAB: | 503 |
| 379 | 2 | —CH(CO$_2$H)—OCH$_2$CO$_2$H | FAB: | 461 |
| 20 | 20 | —CH$_2$CO$_2$H | FAB: | 387 |
| 11 | 11 | —(CH$_2$)$_2$—CO$_2$Et | FAB: | 429 |
| 24 | 24 |  CO$_2$Et | FAB: | 427 |
| 380 | 2 |  CO$_2$H | FAB: | 399 |
| 55 | 55 |  CONH$_2$ | FAB: | 398 |
| 381 | 57, 2 | Me–C(=)–CO$_2$H | ESI: | 413 |
| 382 | 24 | CO$_2$Et with Me | FAB: | 441 |
| 383 | 2 | CO$_2$H with Me | FAB: | 413 |

TABLE 39-continued
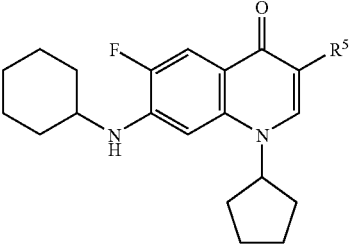
| Ex | Syn | R⁵ | Data |
|---|---|---|---|
| 384 | 24 | 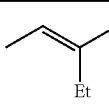 | FAB: 455 |
| 385 | 2 | 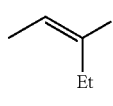 | FAB: 427 |
| 386 | 24 | 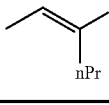 | FAB: 441 |
TABLE 40
| 387 | 2 | 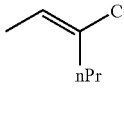 | FAB: 469 |
|---|---|---|---|
| 388 | 24 | 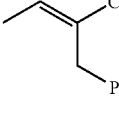 | FAB: 517 |
| 389 | 2 | 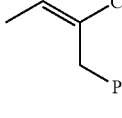 | FAB: 489 |
| 390 | 24 | 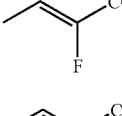 | FAB: 445 |
| 391 | 2 | 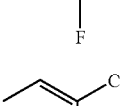 | FAB: 417 |
| 392 | 24 | 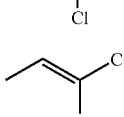 | FAB: 461 |
| 393 | 2 | 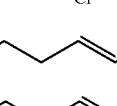 | ESI: 433 |
| 48 | 48 |  | FAB: 455 |
| 394 | 2 |  | ESI: 427 |
TABLE 40-continued
| 395 | 1 | 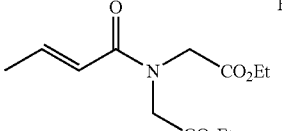 | FAB: 570 |
|---|---|---|---|
| 396 | 2 | 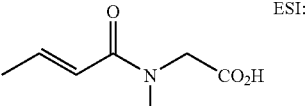 | ESI: 514 |
| 397 | 24 | 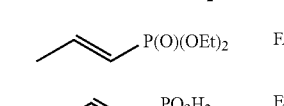 | FAB: 491 |
| 398 | 3 | 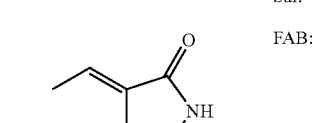 | ESI: 435  Sal: HBr |
| 41 | 41 | 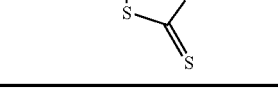 | FAB: 472 |
TABLE 41
| 399 | 1 | 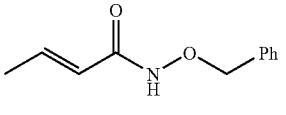 | FAB: 504 |
|---|---|---|---|
| 400 | 11 | 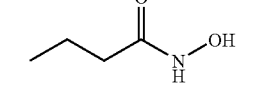 | FAB: 416 |
| 401 | 55 | 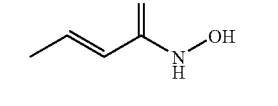 | FAB: 414 |
| 61 | 61 | 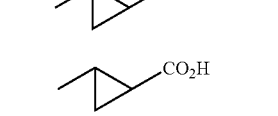 | FAB: 441 |
| 402 | 2 | 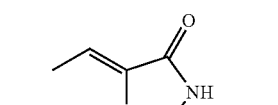 | FAB: 413 |
| 403 | 41 | 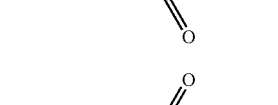 | ESI: 456 |
| 404 | 11 | 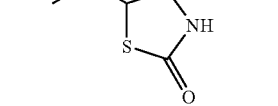 | FAB: 458 |
| 69 | 69 | 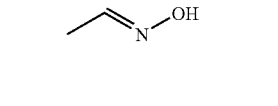 | FAB: 372 |

TABLE 41-continued
| | | | |
|---|---|---|---|
| 70 | 70 | —CH$_2$NH$_2$OH | FAB: 374 |
| 66 | 66 | 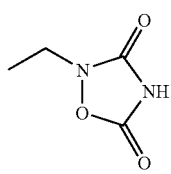 | FAB: 443 |
| 405 | 59 | 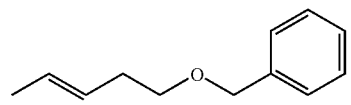 | FAB: 489 |
| 406 | 11 | —(CH$_2$)$_4$—OH | FAB: 401 |
| 67 | 67 | —(CH$_2$)$_3$—CHO | ESI: 399 |
| 68 | 68 | 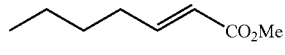 | FAB: 455 |
| 407 | 2 | 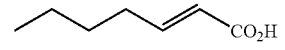 | ESI: 441 |
TABLE 42
| | | | |
|---|---|---|---|
| 408 | 24 | 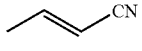 | FAB: 380 |
| 409 | 32 | 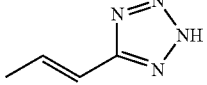 | FAB: 423 |
TABLE 43
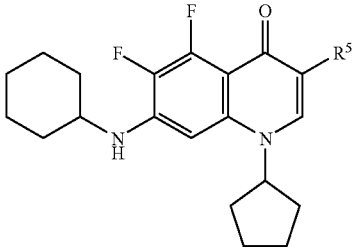
| Ex | Syn | R$^5$ | Data |
|---|---|---|---|
| 410 | 29 | —CH$_2$OH | FAB: 377 |
| 411 | 39 | —CHO | FAB: 375 |
TABLE 43-continued
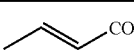
| Ex | Syn | R$^5$ | Data |
|---|---|---|---|
| 412 | 24 | 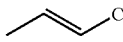 | FAB: 445 |
| 413 | 2 | 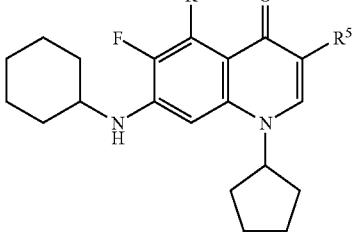 | FAB: 417 |
TABLE 44
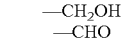
| Ex | Syn | R$^3$ | R$_5$ | Data |
|---|---|---|---|---|
| 414 | 29 | —OBn | —CH$_2$OH | FAB: 465 |
| 415 | 11 | —OH | —CH$_2$OH | FAB: 375 |
| 416 | 39 | —OH | —CHO | FAB: 373 |
| 417 | 24 | —OH | 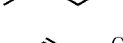 | FAB: 443 |
| 418 | 2 | —OH | 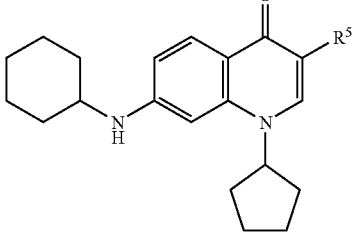 | ESI: 415 |
TABLE 45
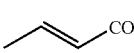
| Ex | Syn | R$^5$ | Data |
|---|---|---|---|
| 419 | 29 | —CH$_2$OH | FAB: 341 |
| 420 | 39 | —CHO | FAB: 339 |
| 421 | 24 | 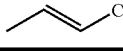 | FAB: 409 |
| 422 | 2 | 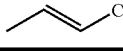 | FAB: 381 |

TABLE 46
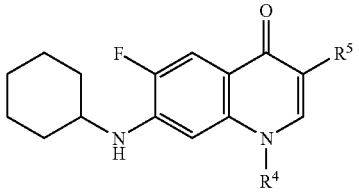
| Ex | Syn | R⁴ | R⁵ | Data |
|---|---|---|---|---|
| 423 | 33 | Et | CN | FAB: 314 |
| 424 | 34 | | —CH₂NHBoc | FAB: 418 |
| 425 | 33 | —CH(Et)₂ | CN | FAB: 356 |
| 35 | 35 | | —CH₂NHBoc | FAB: 460 |
| 426 | 4 | | 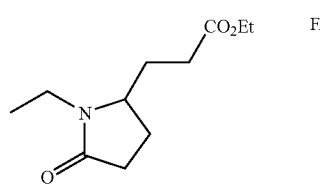 | FAB: 528 |
| 427 | 2 | | 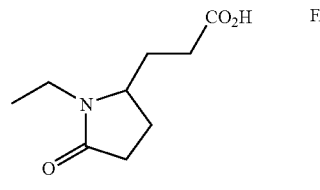 | FAB: 500 |
| 428 | 8 | | 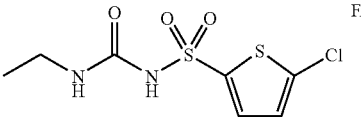 | FAB: 583 |
| 33 | 33 | cPen | CN | FAB: 354 |
| 34 | 34 | | —CH₂NHBoc | FAB: 458 |
| 429 | 1 | | 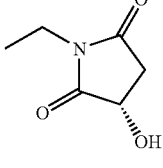 | FAB: 456 |
| 430 | 33 | 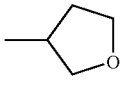 | CN | FAB: 356 |
| 431 | 34 | | —CH₂NHBoc | FAB: 460 |
| 432 | 33 | 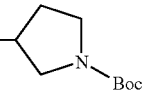 | CN | FAB: 455 |
| 433 | 28 | 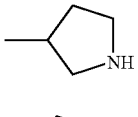 | CN | FAB: 355<br>Sal: 2HCl |
| 434 | 5 | 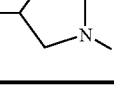 | CN | FAB: 369 |
| 435 | 35 | | —CH₂NHBoc | FAB: 473 |

TABLE 47

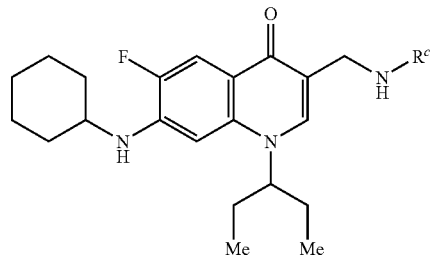

| Ex | Syn | R$^c$ | Data | |
|---|---|---|---|---|
| 436 | 28 | H | FAB: | 360; |
|  |  |  | Sal: | 2HCl |
| 437 | 9 | —CH$_2$CO$_2$Et | FAB: | 446 |
| 438 | 2 | —CH$_2$CO$_2$H | FAB: | 418 |
| 439 | 4 | —(CH$_2$)$_3$—CO$_2$Et | FAB: | 474 |
| 440 | 2 | —(CH$_2$)$_3$—CO$_2$H | ESI (Neg): | 444 |
| 441 | 4 | [CH(CH$_2$CO$_2$Me)CH$_2$CO$_2$Me branched] | FAB: | 518 |
| 442 | 2 | [CH(CH$_2$CO$_2$H)CH$_2$CO$_2$H branched] | FAB: | 490; |
|  |  |  | Sal: | AcOH |
| 5 | 5 | —CH(Me)CH$_2$P(O)(OEt)$_2$ | ESI: | 538 |
| 443 | 3 | —CH(Me)CH$_2$PO$_3$H$_2$ | ESI: | 482; |
|  |  |  | Sal: | 2HBr |
| 444 | 4, 49 | —CH$_2$CF$_2$P(O)(OEt)$_2$ | FAB: | 560; |
|  |  |  | Sal: | HCl |
| 445 | 3 | —CH$_2$CF$_2$PO$_3$H$_2$ | FAB: | 504; |
|  |  |  | Sal: | HBr |

TABLE 48

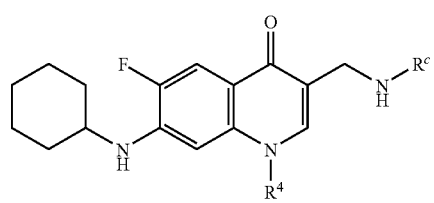

| Ex | Syn | R$^4$ | R$^c$ | Data | |
|---|---|---|---|---|---|
| 446 | 28 | Et | H | FAB: | 318; |
|  |  |  |  | Sal: | 2HCl |
| 49 | 9, 49 |  | —CH$_2$CO$_2$Et | FAB: | 404; |
|  |  |  |  | Sal: | HCl |
| 447 | 2 |  | —CH$_2$CO$_2$H | FAB: | 376; |
|  |  |  |  | Sal: | HCl |

TABLE 48-continued

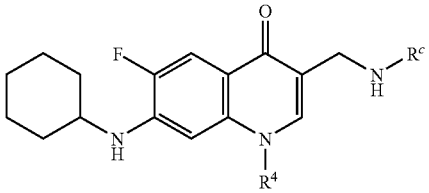

| Ex | Syn | R$^4$ | R$^c$ | Data | |
|---|---|---|---|---|---|
| 448 | 4 | iPr | 3-methylphenyl-CO$_2$Me | FAB: | 466 |
| 449 | 2 |  | 3-methylphenyl-CO$_2$H | FAB: | 452 |
| 450 | 28 | cPen | H | FAB: | 358; |
|  |  |  |  | Sal: | 2HCl |
| 56 | 56 |  | —CH$_2$CO$_2$Et | FAB: | 444; |
|  |  |  |  | Sal: | HCl |
| 4 | 4 |  | 4-hydroxyphenyl-methyl | FAB: | 450 |
| 451 | 4 |  | 2-hydroxyphenyl-methyl | FAB: | 450 |
| 452 | 4 |  | 3-methylphenyl-CO$_2$Me | FAB: | 492 |
| 453 | 2 |  | 3-methylphenyl-CO$_2$H | FAB: | 478 |
| 47 | 47 | tetrahydrofuran-3-yl | H | FAB: | 360; |
|  |  |  |  | Sal: | TFA |
| 454 | 4 |  | —(CH$_2$)$_3$—OH | FAB: | 418 |
| 50 | 4, 50 |  | —CH$_2$CO$_2$Et | FAB: | 418; |
|  |  |  |  | Sal: | Oxa |
| 51 | 51 |  | —CH$_2$CO$_2$H | FAB: | 418; |
|  |  |  |  | Sal: | TFA |
| 36 | 36 | pyrrolidin-3-yl | H | ESI: | 359; |
|  |  |  |  | Sal: | 2HCl |
| 455 | 28 | 1-methylpyrrolidin-3-yl | H | FAB: | 373; |
|  |  |  |  | Sal: | 3HCl |

TABLE 49

| Ex | Syn | R⁴ | R⁶ | Rᶜ | Data |
|---|---|---|---|---|---|
| 456 | 2 | Et | Me | —CH₂CO₂H | FAB: 390 |
| 457 | 4, 49 | | | —CH₂CO₂Et | FAB: 418 Sal: HCl |
| 458 | 5, 49 | —CH(Et)₂ | Me | —CH₂CF₂P(O)(OEt)₂ | FAB: 574 Sal: HCl |
| 459 | 52 | | Me | —CH₂CF₂PO₃Na₂ | ESI: 518 (M⁺ − 2Na + 3) |
| 460 | 9, 49 | | —CH₂CO₂Et | —CH₂CO₂Et | FAB: 532 Sal: HCl |
| 461 | 2 | | —CH₂CO₂H | —CH₂CO₂H | FAB: 476 |

TABLE 50

| Ex | Syn | R⁶ | Rᵈ | Data |
|---|---|---|---|---|
| 462 | 10 | —CH₂CO₂Et | Ph | FAB: 548 |
| 463 | 2 | —CH₂CO₂H | Ph | FAB: 520 |
| 464 | 10 | —CH₂CO₂Et | 4-methylphenol | FAB: 564 |
| 465 | 2 | —CH₂CO₂H | 4-methylphenol | FAB: 536 |
| 466 | 1 | —CH₂CO₂Et | 2-methylphenyl benzyl ether | FAB: 654 |
| 467 | 11 | | 2-methylphenol | FAB: 564 |
| 468 | 2 | —CH₂CO₂H | 2-methylphenol | FAB: 536 |

TABLE 51

| Ex | Syn | R⁶ | Rᵈ | Data |
|---|---|---|---|---|
| 52 | 52 | —CH₂CF₂PO₃Na₂ | Me | ESI: 546 (M⁺ − 2Na + 3) |
| 469 | 6 | —CH₂CF₂P(O)(OEt)₂ | | FAB: 602 |

TABLE 51-continued

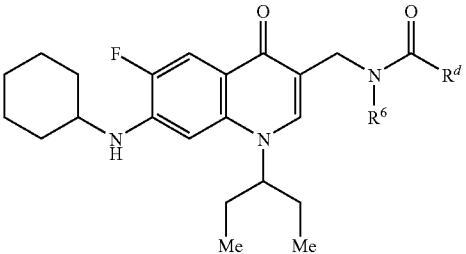

| Ex | Syn | $R^6$ | $R^d$ | Data |
|---|---|---|---|---|
| 6 | 6 | —(CH$_2$)$_3$—CO$_2$Et | | FAB: 516 |
| 470 | 2 | —(CH$_2$)$_3$—CO$_2$H | | FAB: 488 |
| 471 | 10 | —CH$_2$CO$_2$Et | —(CH$_2$)$_2$—CO$_2$Et | ESI: 574 |
| 472 | 2 | —CH$_2$CO$_2$H | —(CH$_2$)$_2$CO$_2$H | FAB: 518 |

TABLE 52

| Ex | Syn | $R^4$ | $R^d$ | Data | |
|---|---|---|---|---|---|
| 473 | 10 | Et | —(CH$_2$)$_2$—CO$_2$Et | FAB: | 446 |
| 474 | 2 | | —(CH$_2$)$_2$—CO$_2$H | FAB: | 418 |
| 475 | 1 | | —CH$_2$P(O)(OEt)$_2$ | FAB: | 496 |
| 476 | 18 | | —CH$_2$PO$_3$H$_2$ | ESI: | 440 |
| 477 | 1 | | (2-ethylpyridine) | FAB: | 437 |
| 478 | 10 | —CH(Et)$_2$ | —(CH$_2$)$_2$—CO$_2$Et | FAB: | 488 |
| 479 | 2 | | —(CH$_2$)$_2$—CO$_2$H | FAB: | 460 |
| 480 | 10, 9 | | N(CH$_2$CO$_2$Et)(CH$_2$CH$_3$)CH$_2$CO$_2$Et | ESI: | 589 |
| 481 | 2 | | N(CH$_2$CO$_2$H)(CH$_2$CH$_3$)CH$_2$CO$_2$H | FAB (Neg): | 531 |
| 482 | 1 | | —CH$_2$P(O)(OEt)$_2$ | FAB: | 538 |
| 483 | 18 | | —CH$_2$PO$_3$H$_2$ | FAB: | 482 |
| 484 | 1 | | —CHFP(O)(OEt)$_2$ | FAB: | 556 |
| 485 | 18 | | —CHFPO$_3$H$_2$ | FAB: | 500 |
| 486 | 10 | | —CF$_2$P(O)(OEt)$_2$ | FAB: | 574 |
| 487 | 18 | | —CF$_2$PO$_3$H$_2$ | FAB: | 518 |
| 488 | 1 | cPen | —CH$_2$OH | FAB: | 416 |
| 489 | 10 | | —(CH$_2$)$_2$—CO$_2$Et | FAB: | 486 |
| 490 | 2 | | —(CH$_2$)$_2$CO$_2$H | FAB: | 458 |
| 491 | 1 | | —CH$_2$P(O)(OEt)$_2$ | FAB: | 536 |
| 492 | 18 | | —CH$_2$PO$_3$H$_2$ | FAB (Neg): | 478 |
| 493 | 10 | (3-tetrahydrofuranyl) | —(CH$_2$)$_2$—CO$_2$Et | FAB: | 488 |
| 494 | 2 | | —(CH$_2$)$_2$—CO$_2$H | FAB: | 460 |

TABLE 52-continued

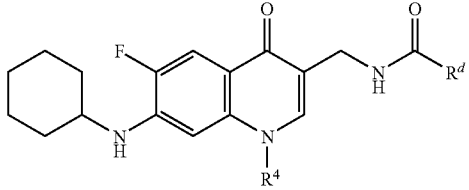

| Ex | Syn | R⁴ | Rᵈ | Data |
|---|---|---|---|---|
| 495 | 10 | | —(CH₂)₂—CO₂Et | FAB: 501 |
| 496 | 2 | 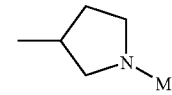 | —(CH₂)₂—CO₂H | FAB: 473 |

TABLE 53

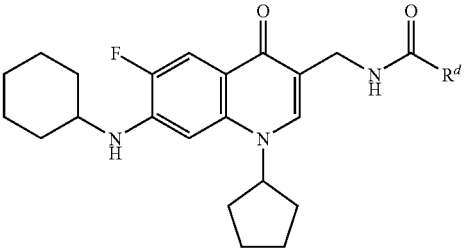

| Ex | Syn | Rᵈ | Data |
|---|---|---|---|
| 497 | 1 | —CH(Me)—nPr | ESI: 456 |
| 498 | 1 | —C(Me)₂—nPr | ESI: 470 |
| 499 | 1 | —C(Me)₂—nBu | ESI: 484 |
| 500 | 1 | 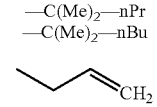 | ESI: 426 |
| 501 | 1 | —CH₂CF₃ | ESI: 468 |
| 502 | 1 | —CH₂CH(Me)CF₃ | ESI: 496 |
| 503 | 1 | —CH₂OH | ESI: 416 |
| 504 | 1 | —CH₂OEt | ESI: 444 |
| 505 | 1 | —CH₂CN | ESI: 425 |
| 506 | 1 | 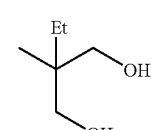 | ESI: 488 |
| 507 | 1, 2 | —(CH₂)₂—CO₂H | ESI: 458 |
| 508 | 1 | —(CH₂)₃—CO₂Et | ESI: 500 |
| 509 | 1, 2 | 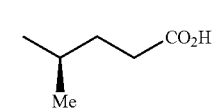 | ESI: 486 |
| 510 | 1, 2 | 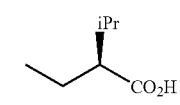 | ESI: 500 |
| 511 | 1, 2 | 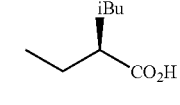 | ESI: 514 |
| 512 | 1, 2 | 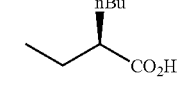 | ESI: 514 |

TABLE 53-continued

| Ex | Syn | Rᵈ | Data |
|---|---|---|---|
| 513 | 1, 2 | (crotonic acid) | ESI: 456 |
| 514 | 1, 2 | (polyhydroxy acid) | ESI: 550 |

TABLE 54

| Ex | Syn | Rᵈ | Data |
|---|---|---|---|
| 515 | 1,2 | (Cbz-protected amino acid, Me) | ESI: 621 |
| 516 | 1,2 | (Cbz-protected amino acid, Me) | ESI: 607 |
| 517 | 1,2 | (benzamide amino acid, Et) | ESI: 577 |

TABLE 54-continued

| # | | Structure | ESI |
|---|---|---|---|
| 518 | 1,2 | (S)-2-(Cbz-amino)butanoic acid derivative | ESI: 607 |
| 519 | 1,2 | (R)-4-(Cbz-amino)pentanoic acid derivative | ESI: 621 |
| 520 | 1,2 | (S)-2-(Cbz-amino)pentanoic acid derivative | ESI: 621 |
| 521 | 1,2 | (R)-2-(Cbz-amino)pentanoic acid derivative | ESI: 621 |
| 522 | 1,2 | (S)-2-(cyclohexylmethyl)butanoic acid | ESI: 540 |
| 523 | 1,2 | (R)-2-(cyclohexylmethyl)butanoic acid | ESI: 540 |
| 524 | 1,2 | 2-ethyl-3-cyclohexylpropanoic acid | ESI: 554 |

TABLE 55

| # | | Structure | ESI |
|---|---|---|---|
| 525 | 1,2 | (S)-2-ethyl-3-cyclohexylpropanoic acid | ESI: 554 |
| 526 | 1,2 | (S)-2-benzylbutanoic acid | ESI: 548 |
| 527 | 1,2 | (R)-2-benzylbutanoic acid | ESI: 548 |
| 528 | 1,2 | —CH(Ph)CH$_2$CO$_2$H | ESI: 534 |
| 529 | 1 | 4-(butyrylamino)benzoic acid | ESI: 577 |
| 530 | 1,2 | 1-pentanoyl-pyridine-4-carboxylic acid | ESI: 569 |
| 531 | 1,2 | (S)-2-(butyrylamino)-3-phenylpropanoic acid | ESI: 605 |
| 532 | 1 | 2-methylcyclopropyl (Me) | ESI: 410 |
| 533 | 1 | cBu | ESI: 440 |
| 534 | 1 | cPen | ESI: 454 |
| 535 | 1 | cHex | ESI: 468 |
| 536 | 1 | 2-methylcyclopent-2-enyl | ESI: 452 |
| 537 | 1 | 4-methylcyclohex-3-enyl | ESI: 466 |
| 538 | 1 | 6-methyl-1,2,3,4-tetrahydronaphthalene | ESI: 516 |
| 539 | 1,2 | trans-2-methylcyclopentane-1-carboxylic acid | ESI: 498 |

TABLE 56

| # | | Structure | ESI |
|---|---|---|---|
| 540 | 1 | trans-2-methyl-1-benzoylcyclohexane | ESI: 572 |
| 541 | 1,2 | trans-2-methylcyclohexane-1-carboxylic acid | ESI: 512 |
| 542 | 1,2 | trans-4-methylcyclohexane-1-carboxylic acid | ESI: 512 |
| 543 | 1,2 | trans-2-methylcyclohexane-1-carboxylic acid | ESI: 512 |
| 544 | 1,2 | trans-2-methylcyclohex-3-ene-1-carboxylic acid | ESI: 510 |

TABLE 56-continued
| 545 | 1 | —CH₂-cPen | ESI: 468 |
| 546 | 1 | 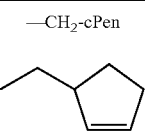 | ESI: 466 |
| 547 | 1,2 | 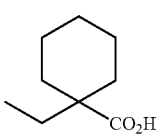 | ESI: 526 |
| 548 | 1 | 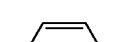 | ESI: 476 |
| 549 | 1 | 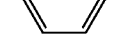 | ESI: 480 |
| 550 | 1 | 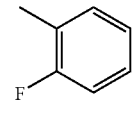 | ESI: 480 |
| 551 | 1 | 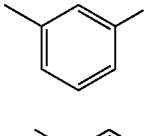 | ESI: 478 |
| 552 | 1 | 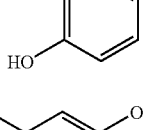 | ESI: 478 |
| 553 | 1 | 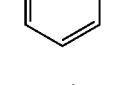 | ESI: 494 |
TABLE 57
| 554 | 1 | 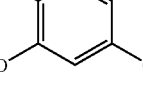 | ESI: 494 |
| 555 | 1 | 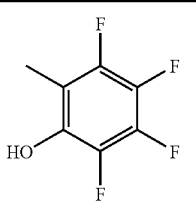 | ESI: 508 |
| 556 | 1 | 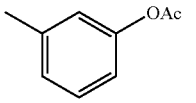 | ESI: 512 |
| 557 | 1 | 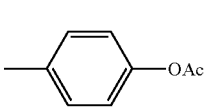 | ESI: 604 |
TABLE 57-continued
| 558 | 1 | 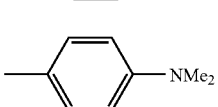 | ESI: 550 |
| 559 | 1 | 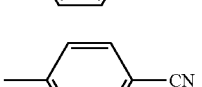 | ESI: 520 |
| 560 | 1 | 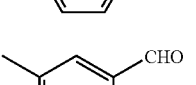 | ESI: 520 |
| 561 | 1 | 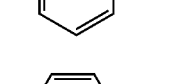 | ESI: 505 |
| 562 | 1 | 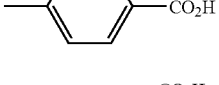 | ESI: 487 |
| 563 | 1 | 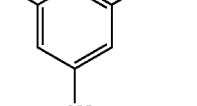 | ESI: 490 |
| 564 | 1,2 | 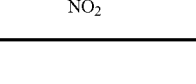 | ESI: 506 |
| 565 | 1,2 | 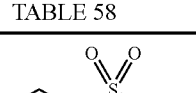 | ESI: 551 |
TABLE 58
| 566 | 1 | 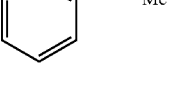 | ESI: 540 |
| 567 | 1 | 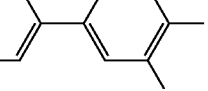 | ESI: 574 |
| 568 | 1 |  | ESI: 574 |

TABLE 58-continued
| | | | |
|---|---|---|---|
| 569 | 1 | 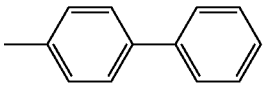 | ESI: 538 |
| 570 | 1 | 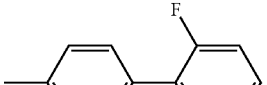 | ESI: 556 |
| 571 | 1,2 | 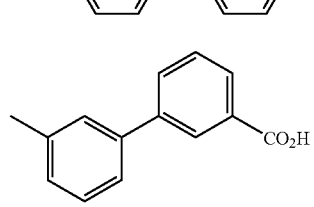 | ESI: 582 |
| 572 | 1 | 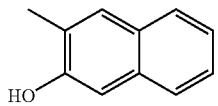 | ESI: 528 |
| 573 | 1 | 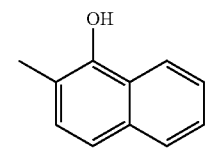 | ESI: 528 |
| 574 | 1 | 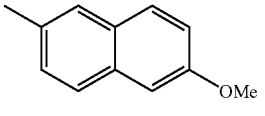 | ESI: 542 |
| 575 | 1 | 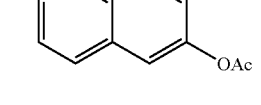 | ESI: 570 |
| 576 | 1 | 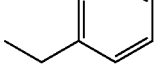 | ESI: 492 |
| 577 | 1 | 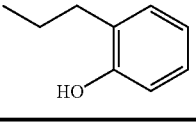 | ESI: 506 |
TABLE 59
| | | | |
|---|---|---|---|
| 578 | 1 | —(CH$_2$)$_4$—Ph | ESI: 518 |
| 579 | 1 | 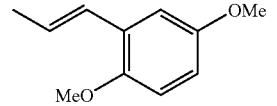 | ESI: 526 |
| 580 | 1 | 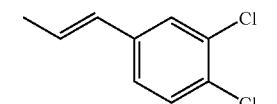 | ESI: 528 |
TABLE 59-continued
| | | | |
|---|---|---|---|
| 581 | 1 | 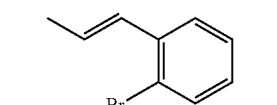 | ESI: 548 |
| 582 | 1 | 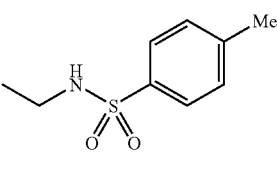 | ESI: 556 |
| 583 | 1 | 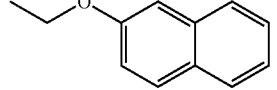 | ESI: 566 |
| 584 | 1 | 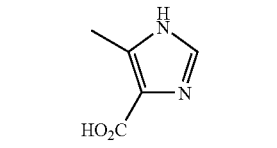 | ESI: 569 |
| 585 | 1 | 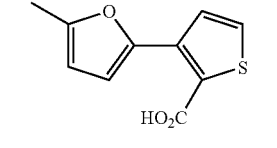 | ESI: 542 |
| 586 | 1,2 | 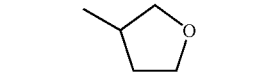 | ESI: 496 |
| 587 | 1,2 | 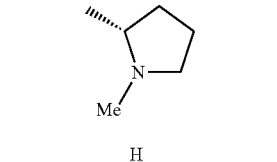 | ESI: 578 |
| 588 | 1 | 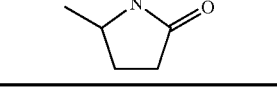 | ESI: 456 |
| 589 | 1 | 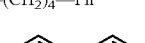 | ESI: 469 |
| 590 | 1 | 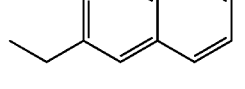 | ESI: 469 |
TABLE 60
| | | | |
|---|---|---|---|
| 591 | 1 | 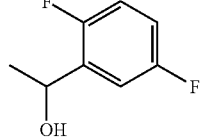 | ESI: 545 |
| 592 | 1 | 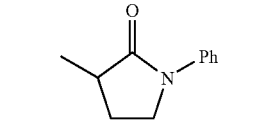 | ESI: 549 |

TABLE 60-continued
| 593 | 1 | 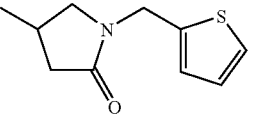 | ESI: 565 |
| 594 | 1 | 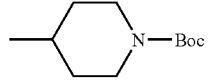 | ESI: 569 |
| 595 | 1 | 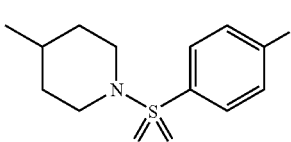 | ESI: 623 |
| 596 | 1 | 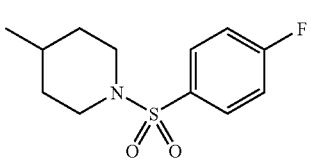 | ESI: 627 |
| 597 | 1 | 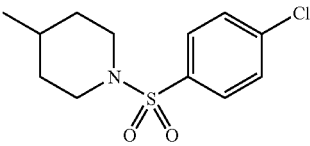 | ESI: 643 |
| 598 | 1 | 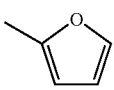 | ESI: 452 |
| 599 | 1 | 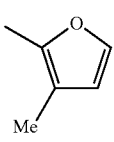 | ESI: 466 |
| 600 | 1 | 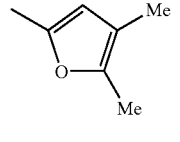 | ESI: 480 |
| 601 | 1 | 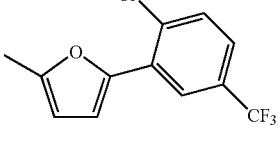 | ESI: 630 |
| 602 | 1 | 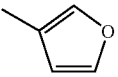 | ESI: 452 |
TABLE 61
| 603 | 1 | 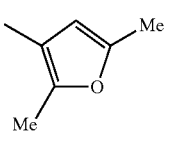 | ESI: 466 |
| 604 | 1 | 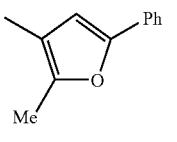 | ESI: 480 |
| 605 | 1 | 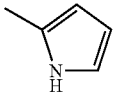 | ESI: 542 |
| 606 | 1 | 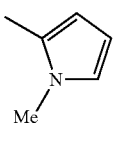 | ESI: 451 |
| 607 | 1 | 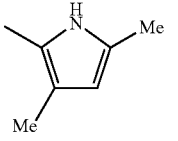 | ESI: 465 |
| 608 | 1 | 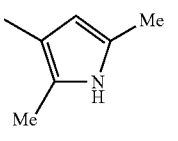 | ESI: 479 |
| 609 | 1 | 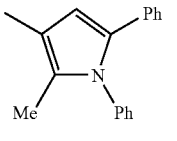 | ESI: 479 |
| 610 | 1 | 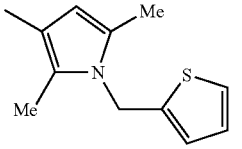 | ESI: 617 |
| 611 | 1 | 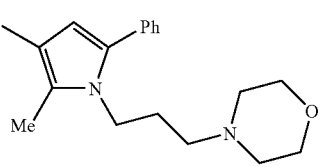 | ESI: 575 |
| 612 | 1 | 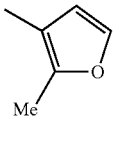 | ESI: 668 |
| 613 | 1,2 | 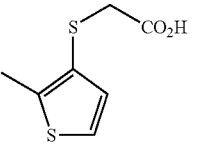 | ESI: 558 |

TABLE 62
| | | | |
|---|---|---|---|
| 614 | 1 | 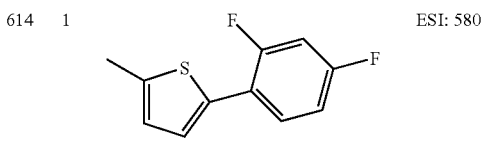 | ESI: 580 |
| 615 | 1 | 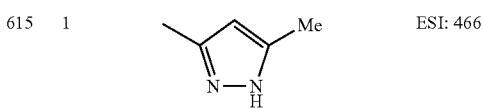 | ESI: 466 |
| 616 | 1 | 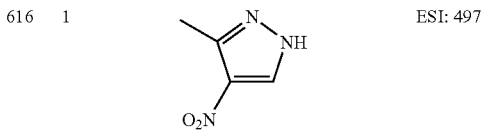 | ESI: 497 |
| 617 | 1 | 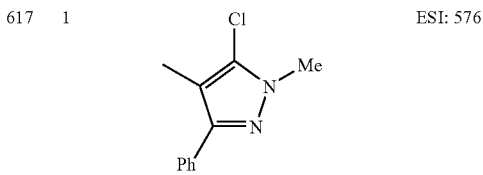 | ESI: 576 |
| 618 | 1 |  | ESI: 596 |
| 619 | 1 | 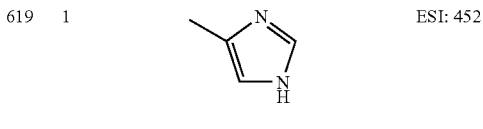 | ESI: 452 |
| 620 | 1 | 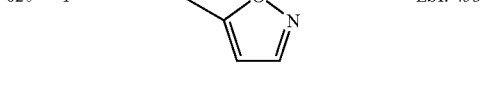 | ESI: 453 |
| 621 | 1 | 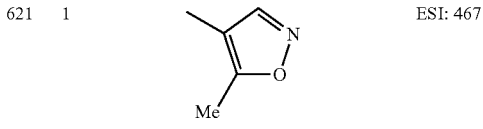 | ESI: 467 |
| 622 | 1 | 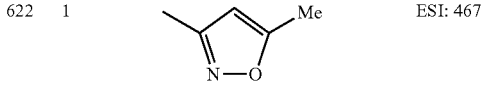 | ESI: 467 |
| 623 | 1 | 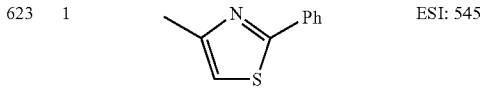 | ESI: 545 |
| 624 | 1 | 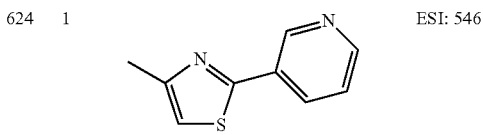 | ESI: 546 |
| 625 | 1 | 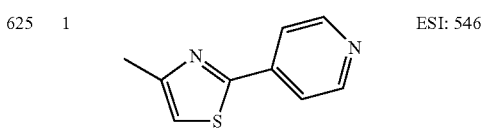 | ESI: 546 |
TABLE 63
| | | | |
|---|---|---|---|
| 626 | 1 | 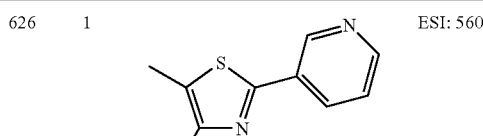 | ESI: 560 |
| 627 | 1 | 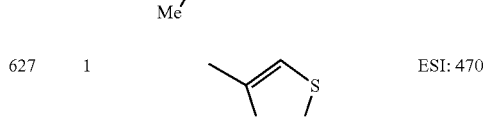 | ESI: 470 |
| 628 | 1 | 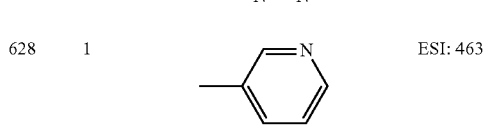 | ESI: 463 |
| 629 | 1 | 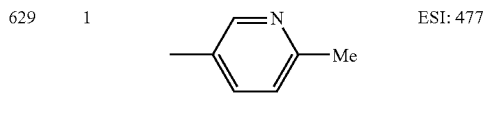 | ESI: 477 |
| 630 | 1 | 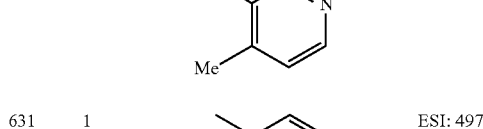 | ESI: 477 |
| 631 | 1 | 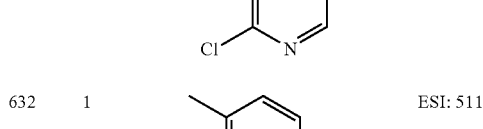 | ESI: 497 |
| 632 | 1 | 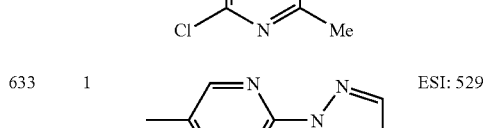 | ESI: 511 |
| 633 | 1 | 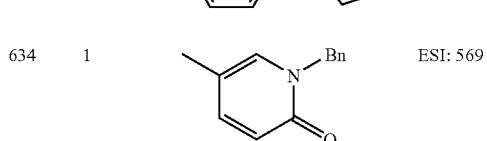 | ESI: 529 |
| 634 | 1 | 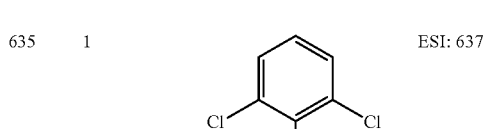 | ESI: 569 |
| 635 | 1 | 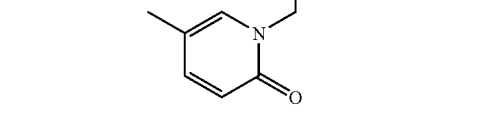 | ESI: 637 |
| 636 | 1 | 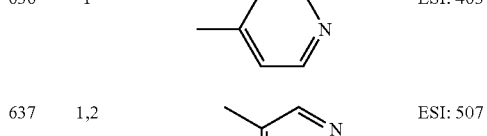 | ESI: 463 |
| 637 | 1,2 | 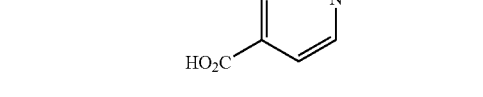 | ESI: 507 |

TABLE 63-continued
| 638 | 1 | 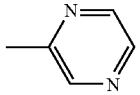 | ESI: 464 |
TABLE 64
| 639 | 1 | 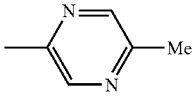 | ESI: 478 |
| 640 | 1 | 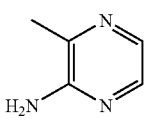 | ESI: 479 |
| 641 | 1 | 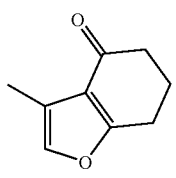 | ESI: 520 |
| 642 | 1 | 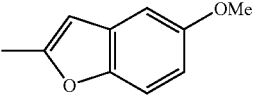 | ESI: 532 |
| 643 | 1 | 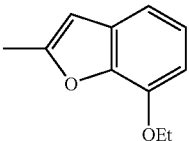 | ESI: 546 |
| 644 | 1 | 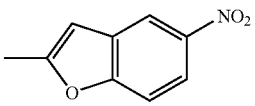 | ESI: 547 |
| 645 | 1 | 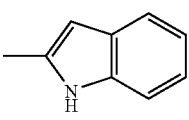 | ESI: 501 |
| 646 | 1 | 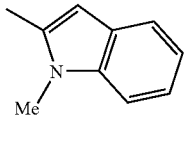 | ESI: 515 |
| 647 | 1 | 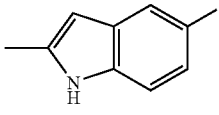 | ESI: 535 |
| 648 | 1 | 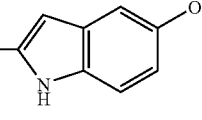 | ESI: 517 |
TABLE 64-continued
| 649 | 1 | 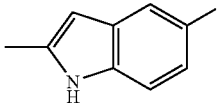 | ESI: 531 |
TABLE 65
| 650 | 1 | 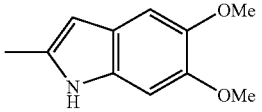 | ESI: 561 |
| 651 | 1 | 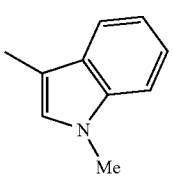 | ESI: 515 |
| 652 | 1 | 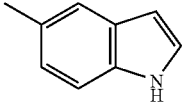 | ESI: 501 |
| 653 | 1 | 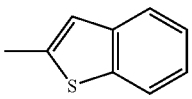 | ESI: 518 |
| 654 | 1 | 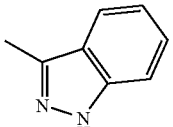 | ESI: 502 |
| 655 | 1 | 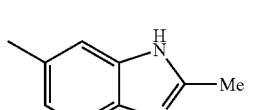 | ESI: 516 |
| 656 | 1 | 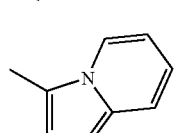 | ESI: 516 |
| 657 | 1 | 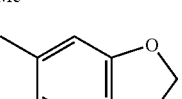 | ESI: 506 |
| 658 | 1 | 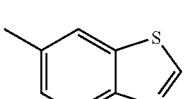 | ESI: 519 |
| 659 | 1 | 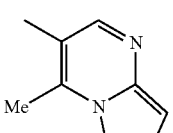 | ESI: 531 |

TABLE 65-continued
| 660 | 1 | 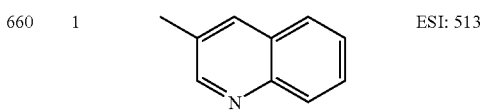 | ESI: 513 |
TABLE 66
| 661 | 1 | 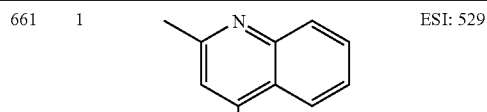 | ESI: 529 |
| 662 | 1 | 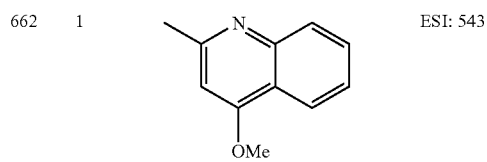 | ESI: 543 |
| 663 | 1 | 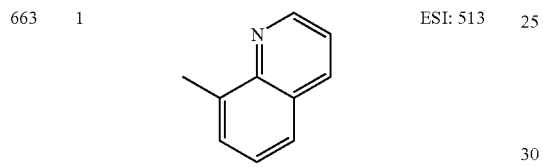 | ESI: 513 |
| 664 | 1 | 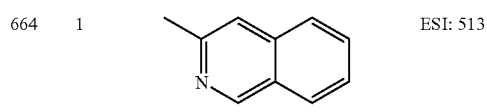 | ESI: 513 |
| 665 | 1 | 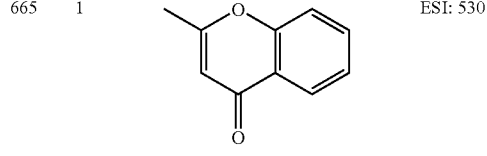 | ESI: 530 |
| 666 | 1 | 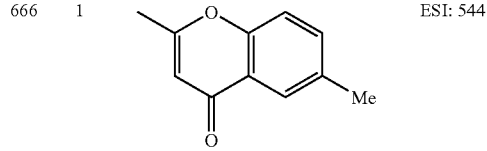 | ESI: 544 |
| 667 | 1 | 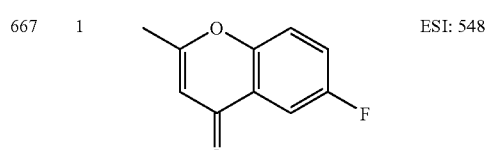 | ESI: 548 |
| 668 | 1 | 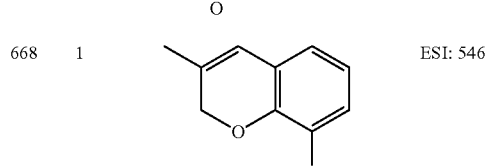 | ESI: 546 |
| 669 | 1 | 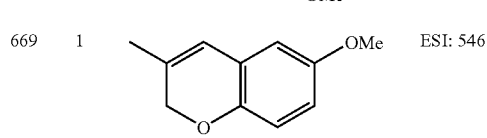 | ESI: 546 |
TABLE 66-continued
| 670 | 1 | 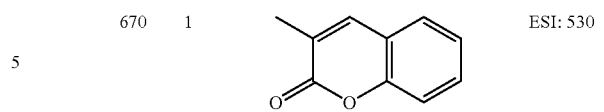 | ESI: 530 |
TABLE 67
| 671 | 1 | 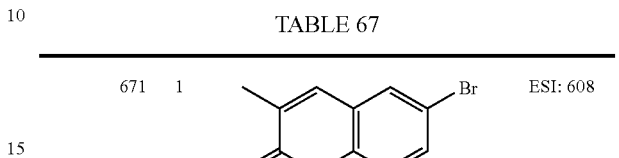 | ESI: 608 |
| 672 | 1 | 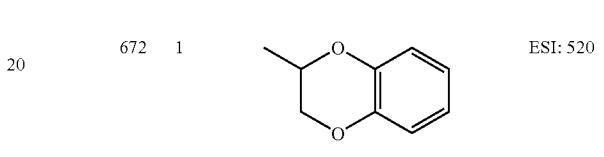 | ESI: 520 |
| 673 | 1 | 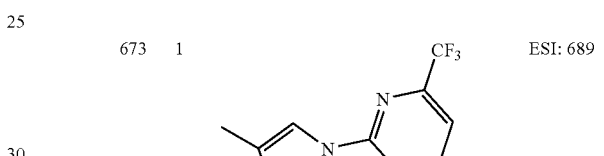 | ESI: 689 |
| 674 | 1 | 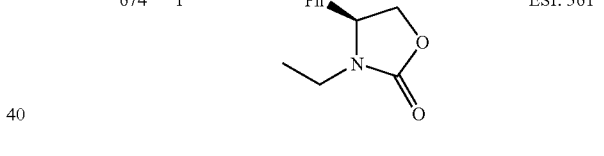 | ESI: 561 |
| 675 | 1 | 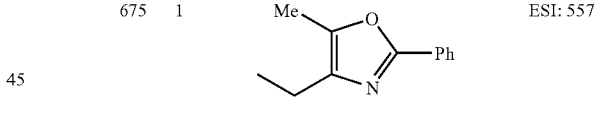 | ESI: 557 |
| 676 | 1 | 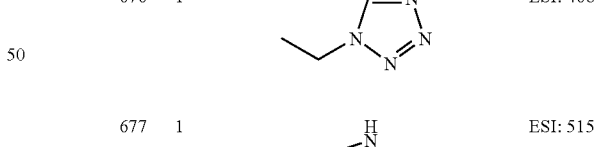 | ESI: 468 |
| 677 | 1 | 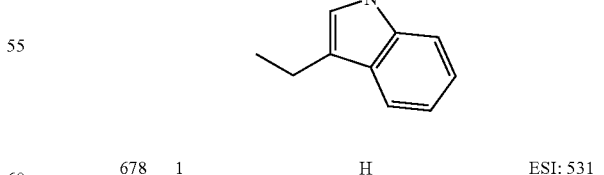 | ESI: 515 |
| 678 | 1 | 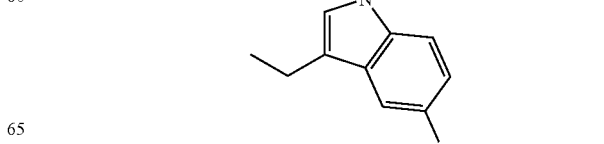 | ESI: 531 |

TABLE 67-continued
| | | | |
|---|---|---|---|
| 679 | 1 |  | ESI: 545 |
TABLE 68
| | | | |
|---|---|---|---|
| 680 | 1 | 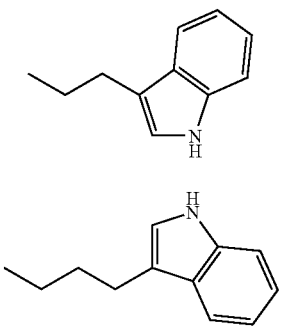 | ESI: 529 |
| 681 | 1 | | ESI: 543 |
| 682 | 1 | | ESI: 544 |
| 683 | 1,2 | | ESI: 535 |
| 684 | 1 | | ESI: 478 |
| 685 | 1 | | ESI: 532 |
| 686 | 1 | | ESI: 538 |
| 687 | 1 | | ESI: 579 |
TABLE 69
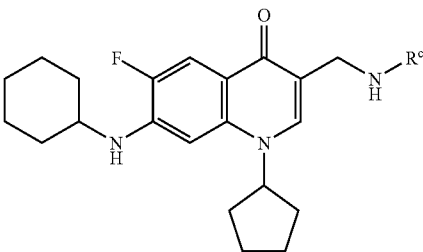
| Ex | Syn | R$^c$ | Data |
|---|---|---|---|
| 688 | 5 | 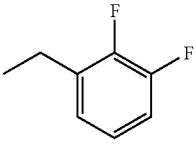 | ESI: 484 |
| 689 | 5 | 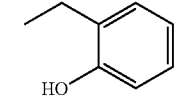 | ESI: 484 |
| 690 | 5 | 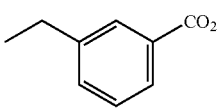 | ESI: 464 |
| 691 | 5 | 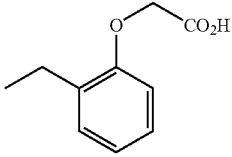 | ESI: 492 |
| 692 | 5 | 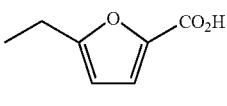 | ESI: 522 |
| 693 | 5 | 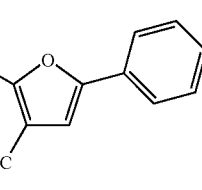 | ESI: 482 |
| 694 | 5,2 | 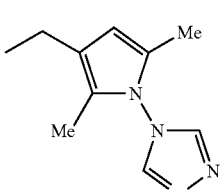 | ESI: 592 |
| 695 | 5 | 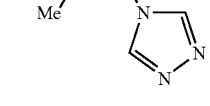 | ESI: 532 |

TABLE 70

| | | | |
|---|---|---|---|
| 696 | 5 | 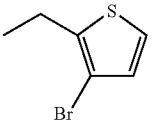 3-bromo-2-ethylthiophene | ESI: 532 |
| 697 | 5 | 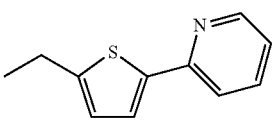 2-(5-ethylthiophen-2-yl)pyridine | ESI: 531 |
| 698 | 5 | 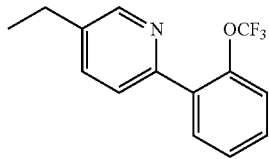 5-ethyl-2-(2-(trifluoromethoxy)phenyl)pyridine | ESI: 609 |
| 699 | 5,2 | 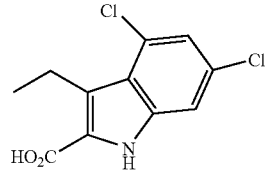 4,6-dichloro-3-ethyl-1H-indole-2-carboxylic acid | ESI: 599 |
| 700 | 5,2 | 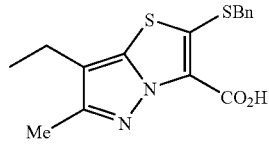 2-(benzylthio)-7-ethyl-6-methylpyrazolo[5,1-b]thiazole-3-carboxylic acid | ESI: 674 |

TABLE 71

| Ex | Syn | R⁵ | Data |
|---|---|---|---|
| 701 | 29 | —CH₂OH | FAB: 360 |
| 702 | 39 | —CHO | FAB: 358 |
| 703 | 24 | 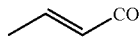 —CH=CH—CO₂Et | FAB: 428 |
| 704 | 2 | 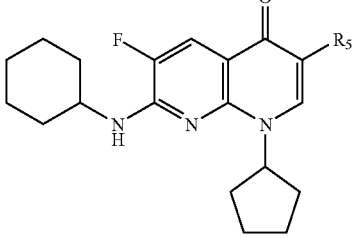 —CH=CH—CO₂H | FAB: 400 |

TABLE 72

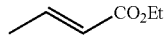

| Ex | Syn | R⁵ | Data |
|---|---|---|---|
| 705 | 29 | —CH₂OH | FAB: 360 |
| 706 | 39 | —CHO | FAB: 358 |
| 707 | 24 |  —CH=CH—CO₂Et | FAB: 428 |
| 708 | 2 | 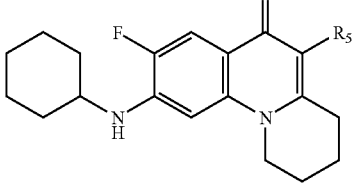 —CH=CH—CO₂H | FAB: 400 |

TABLE 73

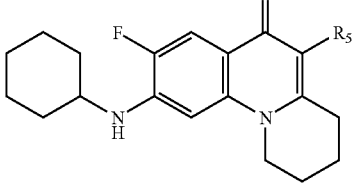

| Ex | Syn | R⁵ | Data |
|---|---|---|---|
| 709 | 40 | —OH | FAB: 331 |
| 710 | 27 | —OCH₂CO₂Et | FAB: 417 |
| 711 | 2 | —OCH₂CO₂H | FAB: 389 |
| 712 | 71 | —CH₂OH | FAB: 345 |
| 713 | 39 | —CHO | FAB: 343 |

TABLE 74

| Ex | Data |
|---|---|
| 32 | NMR(DMSO-d$_6$)δ; 1.11-1.48(m, 5H), 1.60-1.68(m, 1H), 1.70-1.84(m, 8H), 1.90-1.99(m, 2H), 2.08-2.19(m, 2H), 3.48-3.55(m, 1H), 4.98-5.07(m, 1H), 5.45(s, 2H), 6.03-6.09(m, 1H), 6.72(d, J = 7.4 Hz, 1H), 7.71(d, J = 12.4 Hz, 1H), 7.74(s, 1H) |
| 76 | NMR(DMSO-d$_6$)δ; 1.10-1.23(m, 1H), 1.24-1.48(m, 4H), 1.44(d, J = 6.6 Hz, 6H), 1.58-1.68(m, 1H), 1.70-1.79(m, 2H), 1.86(quintet, J = 6.9 Hz, 2H), 1.91-2.00(m, 2H), 2.41(t, J = 7.4 Hz, 2H), 3.47-3.58(m, 1H), 3.97(t, J = 6.4 Hz, 2H), 4.89-5.02(m, 1H), 5.92(dd, J = 2.2, 8.3 Hz, 1H), 6.71(d, J = 7.3 Hz, 1H), 7.67(d, J = 12.4 Hz, 1H), 7.74(s, 1H), 12.10(s, 1H) |
| 80 | NMR(DMSO-d$_6$)δ; 1.10-1.24(m, 1H), 1.26-1.51(m, 10H), 1.60-1.69(m, 1H), 1.71-1.80(m, 2H), 1.91-2.07(m, 3H), 2.09-2.20(m, 1H), 2.43-2.60(m, 2H), 3.53-3.65(m, 1H), 4.50(dd, J = 4.9, 7.3 Hz, 1H), 5.03-5.15(m, 1H), 6.23(dd, J = 2.2, 8.3 Hz, 1H), 6.81(d, J = 7.2 Hz, 1H), 7.74(d, J = 12.3 Hz, 1H), 8.11(s, 1H) |
| 82 | NMR(DMSO-d$_6$)δ; 1.11-1.23(m, 1H), 1.26-1.51(m, 4H), 1.44(d, J = 6.7 Hz, 3H), 1.47(d, J = 6.5 Hz, 3H), 1.48(d, J = 6.5 Hz, 3H), 1.60-1.69(m, 1H), 1.71-1.80(m, 2H), 1.91-2.00(m, 2H), 3.53-3.64(m, 1H), 4.56(q, J = 6.8 Hz, 1H), 5.02-5.14(m, 1H), 6.23(dd, J = 2.2, 8.3 Hz, 1H), 6.81(d, J = 7.3 Hz, 1H), 7.75(d, J = 12.3 Hz, 1H), 8.08(s, 1H), 15.23(brs, 1H) |
| 87 | NMR(DMSO-d$_6$)δ; 1.11-1.46(m, 12H), 1.58-1.67(m, 1H), 1.68-1.77(m, 2H), 1.85-1.95(m, 2H), 2.92-3.03(m, 1H), 3.46-3.57(m, 1H), 4.62(brs, 1H), 4.84-4.95(m, 1H), 6.16-6.28(m, 1H), 6.64-6.71(m, 1H), 6.75-6.96(m, 1H), 7.19-7.39(m, 5H), 7.71(d, J = 12.1 Hz, 1H) |
| 95 | NMR(DMSO-d$_6$)δ; 0.74(t, J = 7.2 Hz, 6H), 1.12-1.53(m, 5H), 1.58-2.00(m, 9H), 3.52-3.68(m, 1H), 4.58(s, 2H), 4.67-4.81(m, 1H), 6.08(d, J = 7.8 Hz, 1H), 6.85(d, J = 6.8 Hz, 1H), 7.72(dd, J = 1.1, 12.3 Hz, 1H), 7.97(s, 1H) |
| 106 | NMR(DMSO-d$_6$)δ; 1.11-1.23(m, 1H), 1.25-1.48(m, 4H), 1.60-1.68(m, 1H), 1.71-1.99(m, 12H), 2.09-2.20(m, 2H), 2.40(t, J = 7.3 Hz, 2H), 3.45-3.56(m, 1H), 3.96(t, J = 6.4 Hz, 2H), 4.96-5.05(m, 1H), 5.95(dd, J = 1.9, 8.2 Hz, 1H), 6.70(d, J = 7.3 Hz, 1H), 7.63(s, 1H), 7.66(d, J = 12.5 Hz, 1H), 12.09(s, 1H) |
| 114 | NMR(DMSO-d$_6$)δ; 1.11-1.56(m, 8H), 1.59-1.78(m, 7H), 1.88-1.96(m, 2H), 1.97-2.08(m, 2H), 3.00(dd, J = 10.4, 14.3 Hz, 1H), 3.49-3.58(m, 1H), 4.72(dd, J = 3.4, 10.4 Hz, 1H), 4.96(quintet, J = 7.2 Hz, 1H), 6.32(d, J = 7.3 Hz, 1H), 6.71(d, J = 7.3 Hz, 1H), 6.88(s, 1H), 7.26-7.41(m, 5H), 7.73(d, J = 12.2 Hz, 1H), 16.29(brs, 1H) |
| 125 | NMR(DMSO-d$_6$)δ; 1.12-1.24(m, 1H), 1.26-1.48(m, 4H), 1.43(d, J = 6.8 Hz, 3H), 1.61-1.69(m, 1H), 1.72-2.00(m, 10H), 2.13-2.25(m, 2H), 3.50-3.61(m, 1H), 4.58(q, J = 6.8 Hz, 1H), 5.12(quintet, J = 6.8 Hz, 1H), 6.22(dd, J = 2.1, 8.2 Hz, 1H), 6.78(d, J = 7.3 Hz, 1H), 7.73(d, J = 12.3 Hz, 1H), 7.92(s, 1H), 14.87(brs, 1H) |
| 146 | NMR(DMSO-d$_6$)δ; 1.12-1.24(m, 1H), 1.25-1.48(m, 4H), 1.60-2.02(m, 15H), 2.09-2.21(m, 2H), 2.25-2.33(m, 2H), 3.45-3.56(m, 1H), 3.95(s, 2H), 5.01(quintet, J = 6.9 Hz, 1H), 5.95(dd, J = 1.9, 8.2 Hz, 1H), 6.70(d, J = 7.3 Hz, 1H), 7.60(s, 1H), 7.67(d, J = 12.5 Hz, 1H), 11.60-12.40(br, 1H) |
| 196 | NMR(DMSO-d$_6$)δ; 0.74(t, J = 7.3 Hz, 6H), 1.10-1.23(m, 1H), 1.24-1.36(m, 2H), 1.37-1.50(m, 2H), 1.61-1.79(m, 5H), 1.81-1.97(m, 4H), 3.53-3.66(m, 1H), 4.69-4.80(m, 1H), 6.04(d, J = 7.0 Hz, 1H), 6.82(d, J = 7.0 Hz, 1H), 7.29(d, J = 4.0 Hz, 1H), 7.67(d, J = 12.2 Hz, 1H), 7.71(d, J = 4.2 Hz, 1H), 8.55(s, 1H), 8.62(s, 1H), 11.30-11.70(br, 1H) |

TABLE 75

| | |
|---|---|
| 202 | NMR(DMSO-d6)δ; 1.12-1.25(m, 1H), 1.26-1.49(m, 4H), 1.60-1.68(m, 1H), 1.71-1.89(m, 10H), 1.93-2.01(m, 2H), 2.13-2.26(m, 2H), 2.39(t, J = 6.5 Hz, 2H), 3.47-3.56(m, 1H), 5.05-5.13(m, 1H), 5.93(d, J = 6.2 Hz, 1H), 6.72(d, J = 7.3 Hz, 1H), 7.14(t, J = 5.7 Hz, 1H), 7.67(d, J = 12.4 Hz, 1H), 8.07(s, 1H), 8.92(s, 1H), 12.19(brs, 1H) |
| 233 | NMR(DMSO-d6)δ; 0.75(t, J = 7.3 Hz, 6H), 1.11-1.51(m, 5H), 1.61-1.79(m, 5H), 1.81-1.99(m, 4H), 2.68(t, J = 6.7 Hz, 2H), 3.53-3.64(m, 1H), 4.68-4.78(m, 1H), 5.98(d, J = 6.8 Hz, 1H), 6.82(d, J = 7.2 Hz, 1H), 7.70(d, J = 12.2 Hz, 1H), 8.91(s, 1H), 9.15(s, 1H), 12.09(brs, 1H) |
| 261 | NMR(CD3OD)δ; 0.84(t, J = 7.3 Hz, 6H), 1.26-1.41(m, 3H), 1.44-1.58(m, 2H), 1.66-1.76(m, 1H), 1.79-2.02(m, 8H), 2.04-2.13(m, 2H), 2.69-2.79(m, 2H), 3.46-3.58(m, 1H), 4.60-4.71(m, 1H), 6.80(d, J = 6.8 Hz, 1H), 7.85(d, J = 12.4 Hz, 1H), 9.05(s, 1H) |
| 271 | NMR(DMSO-d$_6$)δ; 1.11-1.24(m, 1H), 1.26-1.49(m, 4H), 1.61-1.68(m, 1H), 1.72-1.89(m, 10H), 1.93-2.00(m, 2H), 2.15-2.29(m, 4H), 2.45(t, J = 7.4 Hz, 2H), 3.48-3.59(m, 1H), 5.06-5.14(m, 1H), 6.05(dd, J = 2.2, 8.3 Hz, 1H), 6.75(d, J = 7.4 Hz, 1H), 7.69(d, J = 12.3 Hz, 1H), 9.03(s, 1H), 9.06(s, 1H), 12.05(brs, 1H) |
| 297 | NMR(DMSO-d$_6$)δ; 0.27-0.32(m, 2H), 0.47-0.54(m, 2H), 1.10-1.20(m, 1H), 1.68-1.80(m, 2H), 1.81-1.99(m, 4H), 2.13-2.25(m, 2H), 3.18(t, J = 6.2 Hz, 2H), 5.10(quintet, J = 7.0 Hz, 1H), 6.52-6.57(m, 1H), 6.85(d, J = 7.3 Hz, 1H), 7.19(d, J = 15.6 Hz, 1H), 7.55(d, J = 15.6 Hz, 1H), 7.73(d, J = 12.3 Hz, 1H), 8.24(s, 1H), 11.85(brs, 1H) |
| 321 | NMR(DMSO-d$_6$)δ; 1.11-1.47(m, 5H), 1.49(d, J = 6.6 Hz, 6H), 1.60-1.69(m, 1H), 1.71-1.79(m, 2H), 1.91-1.99(m, 2H), 3.52-3.63(m, 1H), 5.02(quintet, J = 6.6 Hz, 1H), 6.11(dd, J = 2.4, 8.4 Hz, 1H), 6.81(d, J = 7.3 Hz, 1H), 7.18(d, J = 15.4 Hz, 1H), 7.55(d, J = 15.6 Hz, 1H), 7.73(d, J = 12.4 Hz, 1H), 8.34(s, 1H), 11.84(s, 1H) |
| 324 | NMR(DMSO-d$_6$)δ; 1.09-1.23(m, 1H), 1.25-1.52(m, 4H), 1.45(d, J = 6.5 Hz, 6H), 1.59-1.68(m, 1H), 1.70-1.79(m, 2H), 1.89-2.00(m, 2H), 3.51-3.62(m, 1H), 5.01(quintet, J = 6.5 Hz, 1H), 6.15(dd, J = 2.1, 8.3 Hz, 1H), 6.80(d, J = 7.1 Hz, 1H), 7.45(s, 2H), 7.62(t, J = 7.5 Hz, 1H), 7.67-7.75(m, 2H), 7.95(d, J = 7.2 Hz, 1H), 8.30(s, 1H), 12.04(brs, 1H) |

TABLE 75-continued

| | |
|---|---|
| 354 | NMR(DMSO-d$_6$)δ; 0.75(t, J = 7.1 Hz, 6H), 1.11-1.51(m, 5H), 1.60-2.00(m, 9H), 3.56-3.66(m, 1H), 4.68-4.78(m, 1H), 6.08(d, J = 7.4 Hz, 1H), 6.87(d, J = 6.8 Hz, 1H), 7.22(d, J = 15.6 Hz, 1H), 7.56(d, J = 15.6 Hz, 1H), 7.73(d, J = 12.7 Hz, 1H), 8.28(s, 1H), 11.85(brs, 1H) |
| 378 | NMR(DMSO-d$_6$)δ; 1.11-1.24(m, 1H), 1.25-1.47(m, 4H), 1.60-1.68(m, 1H), 1.71-1.91(m, 8H), 1.92-2.00(m, 2H), 2.08-220(m, 2H), 2.46(t, J =7.2 Hz, 2H), 2.62(t, J =7.2 Hz, 2H), 3.44-3.56(m, 1H), 4.99(quintet, J = 6.6 Hz, 1H), 5.93(dd, J = 2.1, 8.2 Hz, 1H), 6.71(d, J = 7.3 Hz, 1H), 7.64(d, J = 12.5 Hz, 1H), 7.71(s, 1H), 12.11(s, 1H) |
| 380 | NMR(DMSO-d$_6$)δ; 1.11-1.24(m, 1H), 1.27-1.48(m, 4H), 1.61-1.69(m, 1H), 1.69-1.80(m, 4H), 1.81-1.91(m, 2H), 1.92-2.02(m, 4H), 2.13-2.23(m, 2H), 3.49-3.62(m, 1H), 5.07(quintet, J = 7.1 Hz, 1H), 6.15(dd, J = 2.3, 8.2 Hz, 1H), 6.80(d, J = 7.2 Hz, 1H), 7.18(d, J = 15.6 Hz, 1H), 7.55(d, J = 15.6 Hz, 1H), 7.72(d, J = 12.3 Hz, 1H), 8.22(s, 1H), 11.85(brs, 1H) |

TABLE 76

[Structure: 7-(cyclohexylamino)-6-fluoro-1-isopropyl-3-(OR$^b$)-quinolin-4(1H)-one]

| No | R$^b$ |
|---|---|
| 1 | —CH(Et)CO$_2$H |
| 2 | —CH(nPr)CO$_2$H |
| 3 | —CH(iPr)CO$_2$H |
| 4 | [CH(Me)CH$_2$-(2-pyridyl) with CO$_2$H] |
| 5 | [CH(Me)CH$_2$-(3-pyridyl) with CO$_2$H] |
| 6 | [CH(Me)CH$_2$-(4-pyridyl) with CO$_2$H] |
| 7 | —CH$_2$C(O)NH$_2$ |
| 8 | —CH$_2$CH(OH)CH$_2$CO$_2$H |
| 9 | —(CH$_2$)$_2$—CH(OH)CO$_2$H |
| 10 | —CH$_2$CH(Me)CH$_2$CO$_2$H |
| 11 | —(CH$_2$)$_2$—CH(Me)CO$_2$H |
| 12 | —(CH$_2$)$_2$—C(Me)$_2$CO$_2$H |
| 13 | —CH(CO$_2$H)—(CH$_2$)$_2$—CO$_2$Et |
| 14 | —CH(CO$_2$Et)—(CH$_2$)$_2$—CO$_2$H |
| 15 | —CH$_2$C(O)NH—S(O)$_2$Me |
| 16 | —CH$_2$C(O)NH—S(O)$_2$Ph |
| 17 | [5-isopropyl-1H-tetrazole] |
| 18 | [3-ethyl-1,2,4-oxadiazol-5(4H)-one] |
| 19 | —CH(Me)—(CH$_2$)$_2$—CO$_2$H |
| 20 | —(CH$_2$)$_3$—PO$_3$H$_2$ |

TABLE 76-continued

[Structure: 7-(cyclohexylamino)-6-fluoro-1-isopropyl-3-(OR$^b$)-quinolin-4(1H)-one]

| No | R$^b$ |
|---|---|
| 21 | [5-ethyl-1H-tetrazole] |

TABLE 77

[Structure: 7-(cyclohexylamino)-6-fluoro-1-(pentan-3-yl)-3-(OR$^b$)-quinolin-4(1H)-one]

| No | R$^b$ |
|---|---|
| 22 | —CH(Et)CO$_2$H |
| 23 | —CH(nPr)CO$_2$H |
| 24 | —CH(iPr)CO$_2$H |
| 25 | [CH(Me)CH$_2$-(2-pyridyl) with CO$_2$H] |
| 26 | [CH(Me)CH$_2$-(3-pyridyl) with CO$_2$H] |
| 27 | [CH(Me)CH$_2$-(4-pyridyl) with CO$_2$H] |
| 28 | —CH$_2$C(O)NH$_2$ |

TABLE 77-continued

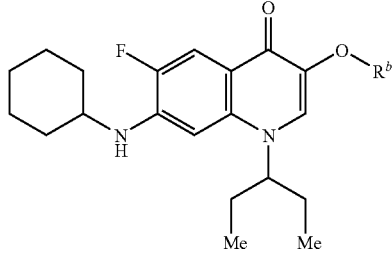

| No | R$^b$ |
|---|---|
| 29 | —CH(Me)C(O)NH$_2$ |
| 30 | —CH$_2$CH(OH)CH$_2$CO$_2$H |
| 31 | —(CH$_2$)$_2$—CH(OH)CO$_2$H |
| 32 | —CH$_2$CH(Me)CH$_2$CO$_2$H |
| 33 | —(CH$_2$)$_2$—CH(Me)CO$_2$H |
| 34 | —(CH$_2$)$_2$—C(Me)$_2$CO$_2$H |
| 35 | —CH(CO$_2$H)—(CH$_2$)$_2$—CO$_2$Et |
| 36 | —CH(CO$_2$Et)—(CH$_2$)$_2$—CO$_2$H |
| 37 | —CH$_2$C(O)NH—S(O)$_2$Me |
| 38 | —CH(Me)C(O)NH—S(O)$_2$Me |
| 39 | —CH$_2$C(O)NH—S(O)$_2$Ph |
| 40 | —CH(Me)C(O)NH—S(O)$_2$Ph |
| 41 | 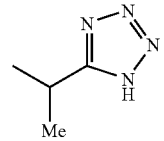 |
| 42 | 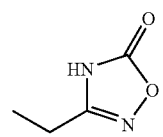 |
| 43 | —CH(Me)CO$_2$H |
| 44 | —CH(Bn)CO$_2$H |
| 45 | —(CH$_2$)$_3$—CO$_2$H |

TABLE 78

| No | R$^b$ |
|---|---|
| 46 | —CH(CO$_2$H)—(CH$_2$)$_2$—CO$_2$H |
| 47 | —CH(Me)—(CH$_2$)$_2$—CO$_2$H |
| 48 | —(CH$_2$)$_3$—PO$_3$H$_2$ |
| 49 | 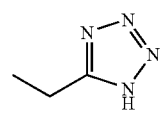 |

TABLE 79

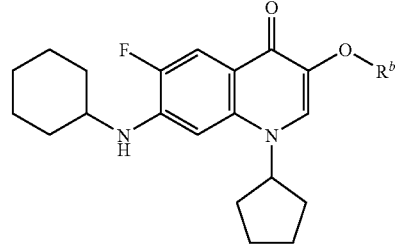

| No | R$^b$ |
|---|---|
| 50 | —CH(nPr)CO$_2$H |
| 51 | 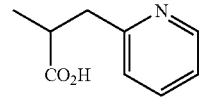 |
| 52 | 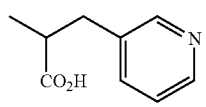 |
| 53 | 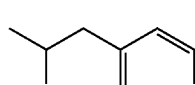 |
| 54 | —CH$_2$C(O)NH$_2$ |
| 55 | —CH(Me)C(O)NH$_2$ |
| 56 | —CH$_2$CH(OH)CH$_2$CO$_2$H |
| 57 | —(CH$_2$)$_2$—CH(OH)CO$_2$H |
| 58 | —(CH$_2$)$_2$—C(Me)$_2$CO$_2$H |
| 59 | —CH(CO$_2$H)—(CH$_2$)$_2$—CO$_2$Et |
| 60 | —CH(CO$_2$Et)—(CH$_2$)$_2$—CO$_2$H |
| 61 | —CH$_2$C(O)NH—S(O)$_2$Me |
| 62 | —CH(Me)C(O)NH—S(O)$_2$Me |
| 63 | —CH$_2$C(O)NH—S(O)$_2$Ph |
| 64 | —CH(Me)C(O)NH—S(O)$_2$Ph |
| 65 | 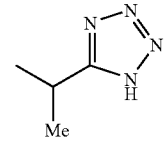 |

TABLE 80

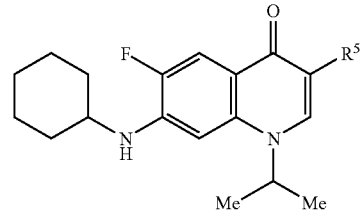

| No | R$^5$ |
|---|---|
| 66 | 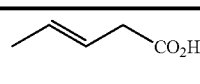 |
| 67 | —(CH$_2$)$_3$—CO$_2$H |
| 68 | —CH$_2$OCH$_2$CO$_2$H |
| 69 | 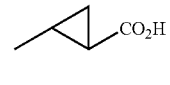 |

TABLE 80-continued
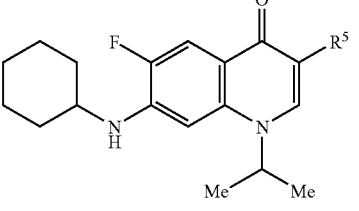
| No | R⁵ |
|---|---|
| 70 | —NHC(O)CH₂CH(Me)CO₂H |
| 71 | —NHC(O)—(CH₂)₂—CH(Me)CO₂H |
| 72 | —NHC(O)—(CH₂)₂—C(Me)₂CO₂H |
| 73 | 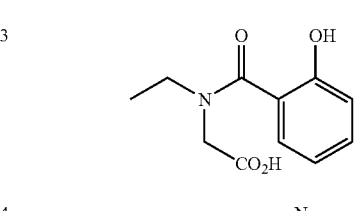 |
| 74 | 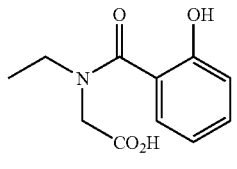 |
| 75 | 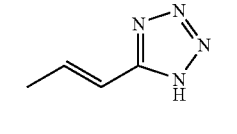 |
| 76 | 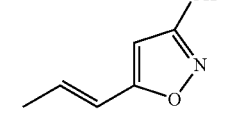 |
| 77 | —(CH₂)₂—CO₂H |
| 78 | —NHC(O)—(CH₂)₂—PO₃H₂ |
| 79 | —NHC(O)CH(Me)CO₂H |
TABLE 81
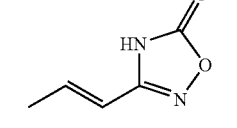
| No | R⁵ |
|---|---|
| 80 | 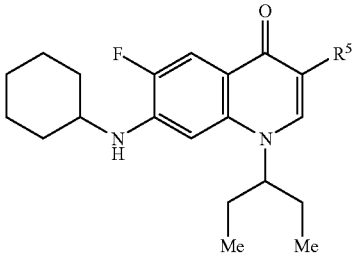 |
| 81 | —(CH₂)₃—CO₂H |
| 82 | —CH₂OCH₂CO₂H |
| 83 | 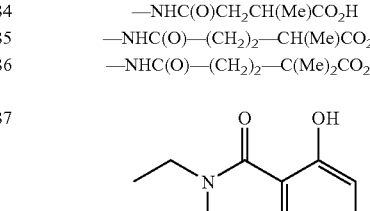 |
TABLE 81-continued
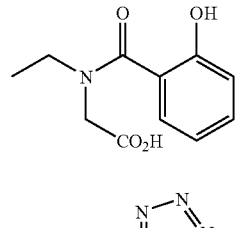
| No | R⁵ |
|---|---|
| 84 | —NHC(O)CH₂CH(Me)CO₂H |
| 85 | —NHC(O)—(CH₂)₂—CH(Me)CO₂H |
| 86 | —NHC(O)—(CH₂)₂—C(Me)₂CO₂H |
| 87 | 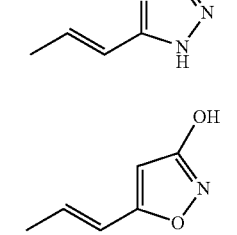 |
| 88 | 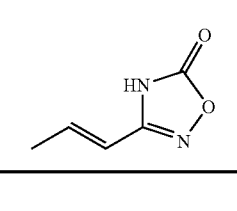 |
| 89 | 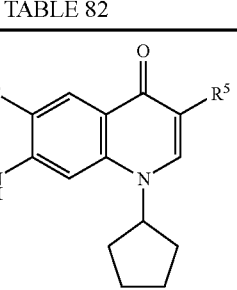 |
| 90 | 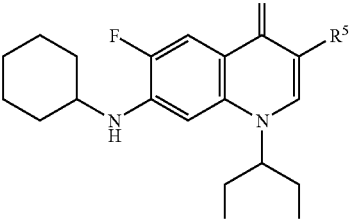 |
TABLE 82
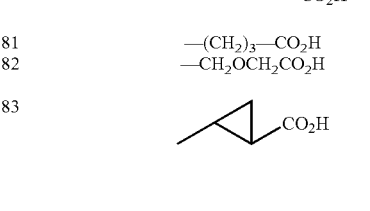
| No | R⁵ |
|---|---|
| 91 | 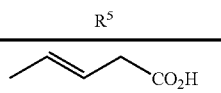 |
| 92 | —(CH₂)₃—CO₂H |
| 93 | —CH₂OCH₂CO₂H |
| 96 | —NHC(O)CH₂CH(Me)CO₂H |
| 97 | —NHC(O)—(CH₂)₂—CH(Me)CO₂H |
| 98 | —NHC(O)—(CH₂)₂—C(Me)₂CO₂H |

TABLE 82-continued

[Structure: 7-(cyclohexylamino)-6-fluoro-1-cyclopentyl-4-oxoquinoline with R5 at 3-position]

| No | R5 |
|---|---|
| 99 | [1H-tetrazol-5-yl propenyl] |
| 100 | [3-hydroxyisoxazol-5-yl propenyl] |
| 101 | [5-oxo-4,5-dihydro-1,2,4-oxadiazol-3-yl propenyl] |
| 102 | —NHC(O)CH(Me)CO$_2$H |

TABLE 83

[Structure: 7-(cyclohexylamino)-6-fluoro-4-oxoquinoline core with N-A substituent, R4 and R5; with N-methyl-N-R4 aminomethylene group A]

| No | N(Me)R4 (A substituent) | R5 |
|---|---|---|
| 103 | 1-methyl-2-methylenepiperidine | —OCH(CH$_3$)CO$_2$H |
| 104 | 1-methyl-2-methylenepiperidine | —OCH(CH$_2$Ph)CO$_2$H |
| 105 | 1-methyl-2-methylenepiperidine | ⎯⎯=⎯⎯CO$_2$H |
| 106 | 1-methyl-2-methylenepiperidine | —NHC(O)—(CH$_2$)$_3$CO$_2$H |
| 107 | 1-methyl-2-methylenepiperidine | —NHC(O)—(CH$_2$)$_2$CO$_2$H |
| 108 | 1,6-dimethyl-2-methylenepiperidine | —OCH$_2$CO$_2$H |
| 109 | 1,6-dimethyl-2-methylenepiperidine | —OCH(CH$_3$)CO$_2$H |
| 110 | 1,6-dimethyl-2-methylenepiperidine | —OCH(CH$_2$Ph)CO$_2$H |
| 111 | 1,6-dimethyl-2-methylenepiperidine | ⎯⎯=⎯⎯CO$_2$H |
| 112 | 1,6-dimethyl-2-methylenepiperidine | —NHC(O)—(CH$_2$)$_3$CO$_2$H |
| 113 | 1,6-dimethyl-2-methylenepiperidine | —NHC(O)—(CH$_2$)$_2$CO$_2$H |

TABLE 83-continued

[Same core structure]

| No | N(Me)R4 (A substituent) | R5 |
|---|---|---|
| 114 | 1,5-dimethyl-2-methylenepiperidine | —OCH$_2$CO$_2$H |
| 115 | 1,5-dimethyl-2-methylenepiperidine | —OCH(CH$_3$)CO$_2$H |
| 116 | 1,5-dimethyl-2-methylenepiperidine | —OCH(CH$_2$Ph)CO$_2$H |
| 117 | 1,5-dimethyl-2-methylenepiperidine | ⎯⎯=⎯⎯CO$_2$H |
| 118 | 1,5-dimethyl-2-methylenepiperidine | —NHC(O)—(CH$_2$)$_3$CO$_2$H |
| 119 | 1,5-dimethyl-2-methylenepiperidine | —NHC(O)—(CH$_2$)$_2$CO$_2$H |
| 120 | 1-methyl-2-methylenepyrrolidine | —OCH$_2$CO$_2$H |
| 121 | 1-methyl-2-methylenepyrrolidine | —OCH(CH$_3$)CO$_2$H |
| 122 | 1-methyl-2-methylenepyrrolidine | —OCH(CH$_2$Ph)CO$_2$H |
| 123 | 1-methyl-2-methylenepyrrolidine | ⎯⎯=⎯⎯CO$_2$H |
| 124 | 1-methyl-2-methylenepyrrolidine | —NHC(O)—(CH$_2$)$_3$CO$_2$H |
| 125 | 1-methyl-2-methylenepyrrolidine | —NHC(O)—(CH$_2$)$_2$CO$_2$H |
| 126 | 1,5-dimethyl-2-methylenepyrrolidine | —OCH$_2$CO$_2$H |
| 127 | 1,5-dimethyl-2-methylenepyrrolidine | —OCH(CH$_3$)CO$_2$H |
| 128 | 1,5-dimethyl-2-methylenepyrrolidine | —OCH(CH$_2$Ph)CO$_2$H |
| 129 | 1,5-dimethyl-2-methylenepyrrolidine | ⎯⎯=⎯⎯CO$_2$H |
| 130 | 1,5-dimethyl-2-methylenepyrrolidine | —NHC(O)—(CH$_2$)$_3$CO$_2$H |
| 131 | 1,5-dimethyl-2-methylenepyrrolidine | —NHC(O)—(CH$_2$)$_2$CO$_2$H |

INDUSTRIAL APPLICABILITY

Since the quinolone derivatives of the present invention or salts thereof have excellent platelet aggregation inhibitory activity or P2Y12 inhibitory activity, they are useful as a pharmaceutical, particularly a platelet aggregation inhibitor or a P2Y12 inhibitor. Accordingly, the compounds of the present invention are useful as a preventive and/or therapeutic agent for a circulatory organ system disease closely related to the thrombus formation by platelet aggregation, such as unstable angina, acute myocardial infarction and its secondary prevention, re-obstruction and re-stricture after coronary artery bypass surgery, PTCA operation or stent indwelling operation, coronary artery thrombolysis acceleration and re-obstruction prevention and the like ischemic diseases; transient cerebral ischemic attack (TIA) cerebral infarction, subarachnoid hemorrhage (vasospasm) and the like cerebrovascular accidents; chronic arterial occlusive disease and the like peripheral arterial diseases; and the like, and as an auxiliary agent at the time of cardiac surgical operation or vascular surgical operation.

The invention claimed is:

1. A quinolone derivative represented by a formula (I) or a pharmaceutically acceptable salt thereof

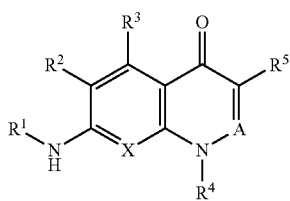

(I)

wherein
- R¹: a cycloalkyl or lower alkylene-cycloalkyl, wherein the cycloalkyl in R¹ may be substituted;
- R²: —H or a halogen;
- R³: —H, a halogen, —OR⁰ or —O-lower alkylene-aryl;
- R⁰: the same or different from each other and each represents —H or a lower alkyl
- R⁴: a lower alkyl, halogeno-lower alkyl, lower alkylene-cycloalkyl, cycloalkyl or heterocyclic group, wherein the cycloalkyl and heterocyclic group in R⁴ may respectively be substituted;
- R⁵: —NO₂, —CN, a lower alkyl, lower alkenyl, halogeno lower alkenyl, -L-Rᵃ, —C(O)R⁰, —O—Rᵇ, —N(R⁶)₂, lower alkylene-N(R⁶)(Rᶜ), —N(R⁶)C(O)—Rᵈ, lower alkylene-N(R⁶)C(O)—Rᵈ, lower) alkylene-N(R⁰)C(O)O-lower alkyl, —N(R⁰)C(O)N(R⁰)—Rᵉ, lower alkylene-N(R⁰)C(O)N(R⁰)—Rᵉ, —N(R⁰)S(O)₂N(R⁰)C(O)—Rᵈ, —CH=NOH, cycloalkyl, heterocyclic group, (2,4-dioxo-1,3-thiazolidin-5-ylidene)methyl or (4-oxo-2-thioxo-1,3-thiazolidin-5-ylidene)methyl, wherein the cycloalkyl and heterocyclic group in R⁵ may respectively be substituted;
- R⁶: H, a lower alkyl, lower alkylene-CO₂R⁰ or lower alkylene-P(O)(ORᵖ)₂, wherein the lower alkylene in R⁶ may be substituted;
- L: a lower alkylene or lower alkenylene which may respectively be substituted;
- Rᵃ: —OR⁰, —CN, —O-lower alkylene-aryl, —O-lower alkylene-CO₂R⁰, —C(O)R⁰, —CO₂R⁰, —C(O)NHOH, —C(O)N(R⁶)₂, —C(O)N(R⁰)-aryl, —C(O)N(R⁰)—S(O)₂-lower alkyl, —C(O)N(R⁰)—S(O)₂-aryl, —C(O)N(R⁰)—S(O)₂-heterocyclic group, —NH₂OH, —OC(O)R⁰, —OC(O)-halogeno-lower alkyl, —P(O)(ORᵖ)₂, an aryl or heterocyclic group, wherein the aryl and heterocyclic group in Rᵃ may be substituted;
- Rᵖ: R⁰, a lower alkylene-OC(O)-lower alkyl, lower alkylene-OC(O)-cycloalkyl, lower alkylene-OC(O)O-lower alkyl, lower alkylene-OC(O)O-cycloalkyl, or lower alkylene-heterocyclic group, wherein the heterocyclic group in Rᵖ may be substituted;
- Rᵇ: H, a cycloalkyl, aryl, heterocyclic group, lower alkylene-Rᵇᵃ or lower alkenylene-Rᵇᵃ, wherein the lower alkylene, lower alkenylene, cycloalkyl, aryl and heterocyclic group in Rᵇ may be substituted;
- Rᵇᵃ: —OR⁰, —O—Si(lower alkyl)₃, —CO₂R⁰, —C(O)NHOH, —C(O)N(R⁰)₂, —C(O)N(R⁰)—S(O)₂-lower alkyl, —C(O)N(R⁰)—S(O)₂-aryl, =C(NH₂)=NOH, —C(NH₂)=NO—C(O)R⁰, —C(NH₂)=NO—C(O)-lower alkylene-C(O)R⁰, —CO₂-lower alkylene-aryl, —P(O)(ORᵖ)₂, —C(O)R⁰, —C(O)-aryl, a cycloalkyl, aryl or heterocyclic group, wherein the aryl and heterocyclic group in Rᵇᵃ may be substituted;
- Rᶜ: H, a lower alkyl, lower alkylene-OR⁰, lower alkylene-CO₂R⁰, lower alkylene-C(O)NHOH, lower)alkylene-C(O)N(R⁰)₂, lower alkylene-P(O)(ORᵖ)₂, lower alkylene-aryl, lower alkylene-heterocyclic group, aryl or heterocyclic group, wherein the lower alkylene, aryl and heterocyclic group in Rᶜ may be substituted;
- Rᵈ: a C₁₋₇ alkyl, lower alkenyl, halogeno-lower alkyl, lower alkylene-Rᵈᵃ, lower alkenylene-Rᵈᵃ, cycloalkyl, aryl or heterocyclic group, wherein the lower alkylene, lower alkenylene, cycloalkyl, aryl and heterocyclic group in Rᵈ may be substituted;
- Rᵈᵃ: —CN, —OR⁰, —OC(O)R⁰, —O-lower alkylene-CO₂R⁰, —O-aryl, —CO₂R⁰, —C(O)NHOH, —C(O)N(R⁰)₂, —CO₂-lower alkylene-N(R⁰)₂, —P(O)(ORᵖ)₂, —N(R⁶)₂, —N(R⁰)C(O)R⁰, —C(O)N(R⁰)-aryl, —C(O)N(R⁰)-(lower alkylene which may be substituted with —CO₂R⁰)-aryl, —N(R⁰)C(O)-aryl, —N(R⁰)C(O)—OR⁰, —N(R⁰)C(O)—O-lower alkylene-aryl, —N(R⁰)S(O)₂-aryl, —S-heterocyclic group, —C(O)N(R⁰)-heterocyclic group, —N(R⁰)C(O)-heterocyclic group, a cycloalkyl, aryl or heterocyclic group, wherein the cycloalkyl, aryl and heterocyclic group in Rᵈᵃ may be substituted;
- Rᵉ: lower alkylene-CO₂R⁰, lower alkylene-C(O)NHOH, lower)alkylene-C(O)N(R⁰)₂, a lower alkylene-heterocyclic group, aryl, heterocyclic group, —S(O)₂-aryl or —S(O)₂-heterocyclic group, wherein the aryl and heterocyclic group in Rᵉ may be substituted;
- X: CH;
- A: C(R⁷);
- R⁷: —H or a lower alkyl, or R⁴ and R⁷ may together form a lower alkylene which may be substituted;
- with the proviso that 7-(cyclohexylamino)-1-ethyl-6-fluoro-4-oxo-1,4-dihydroquinoline-3-carbonitrile is excluded.

2. The compound according to claim 1, wherein R³ is —H, —OH or —F.

3. The compound according to claim 2, wherein A is CH.

4. The compound according to claim 3, wherein R¹ is cyclohexyl or cyclopropylmethyl.

5. The compound according to claim 4, wherein R² is —F.

6. The compound according to claim 5, wherein R⁴ is a lower alkyl or cycloalkyl.

7. The compound according to claim 6, wherein R⁵ is —N(R⁰)C(O)-lower alkylene-CO₂R⁰, lower alkylene-CO₂R⁰, lower alkenylene-CO₂R⁰, —O-lower alkylene-CO₂R⁰, —O-(lower alkylene which may be substituted with —CO₂R⁰)-aryl or —O-lower alkenylene-CO₂R⁰.

8. The compound according to claim 1, which is selected from the group consisting of
- 4-{[7-(cyclohexylamino)-1-cyclopentyl-6-fluoro-4-oxo-1,4-dihydroquinolin-3-yl]amino}-4-oxobutanoic acid,
- 5-{[7-(cyclohexylamino)-1-cyclopentyl-6-fluoro-4-oxo-1,4-dihydroquinolin-3-yl]amino}-5-oxopentanoic acid,
- (2E)-3-[7-(cyclohexylamino)-1-cyclopentyl-6-fluoro-4-oxo-1,4-dihydroquinolin-3-yl]acrylic acid,
- (2S)-2-{[7-(cyclohexylamino)-1-cyclopentyl-6-fluoro-4-oxo-1,4-dihydroquinolin-3-yl]oxy}-3-phenylpropanoic acid, (2E)-3-[7-(cyclohexylamino)-6-fluoro-1-isopropyl-4-oxo-1,4-dihydroquinolin-3-yl]acrylic acid, (2S)-2-{[7-(cyclohexylamino)-6-fluoro-1-isopropyl-4-oxo-1,4-dihydroquinolin-3-yl]oxy}-3-phenylpropanoic acid, (2S)-2-{[7-(cyclohexylamino)-1-cyclopentyl-6-fluoro-4-oxo-1,4-dihydroquinolin-3-yl]oxy}propanoic acid, and (2S)-2-{([7-(cyclohexylamino)-6-fluoro-1-isopropyl-4-oxo-1,4-dihydroquinolin-3-yl]oxy}propanoic acid, or a pharmaceutically acceptable salt thereof.

9. A pharmaceutical composition which comprises the compound or a pharmaceutically acceptable salt thereof according to claim 1, and a pharmaceutically acceptable carrier.

10. The compound according to claim 1, wherein A is CH.

11. The compound according to claim 1, wherein $R^1$ is cyclohexyl or cyclopropylmethyl.

12. The compound according to claim 11, wherein $R^2$ is —F.

13. The compound according to claim 12, wherein $R^4$ is a lower alkyl or cycloalkyl.

14. The compound according to claim 13, wherein $R^5$ is —N($R^0$)C(O)-lower alkylene-$CO_2R^0$, lower alkylene-$CO_2R^0$, lower alkenylene-$CO_2R^0$, —O-lower alkylene-$CO_2R^0$, —O-(lower alkylene which may be substituted with —$CO_2R^0$)-aryl or —O-lower alkenylene-$CO_2R^0$.

15. A compound of the formula:

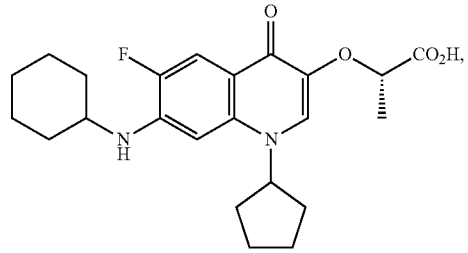

or a pharmaceutically acceptable salt thereof.

16. The compound according to claim 15, which is in a purified form.

17. A pharmaceutical composition comprising the compound or a pharmaceutically acceptable salt thereof according to claim 15, and a pharmaceutically acceptable carrier.

18. A pharmaceutical composition comprising the compound or a pharmaceutically acceptable salt thereof according to claim 16, and a pharmaceutically acceptable carrier.

* * * * *